US012760088B2

(12) United States Patent
Mallapragada et al.

(10) Patent No.: US 12,760,088 B2
(45) Date of Patent: Oct. 13, 2026

(54) NANOSCALE POLYMERIC MICELLAR SCAFFOLDS FOR RAPID AND EFFICIENT ANTIBODY PRODUCTION

(71) Applicant: Iowa State University Research Foundation, Inc., Ames, IA (US)

(72) Inventors: Surya Mallapragada, Ames, IA (US); Michael Wannemuehler, Ames, IA (US); Balaji Narasimhan, Ames, IA (US); Sujata Senapati, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 805 days.

(21) Appl. No.: 18/001,137

(22) PCT Filed: Jun. 8, 2021

(86) PCT No.: PCT/US2021/036436

§ 371 (c)(1),
(2) Date: Dec. 8, 2022

(87) PCT Pub. No.: WO2021/257329

PCT Pub. Date: Dec. 23, 2021

(65) Prior Publication Data

US 2023/0257703 A1 Aug. 17, 2023

Related U.S. Application Data

(60) Provisional application No. 63/041,345, filed on Jun. 19, 2020.

(51) Int. Cl.

| | |
|---|---|
| ***C07K 16/10*** | (2026.01) |
| ***C12N 5/00*** | (2006.01) |
| ***C12N 5/0781*** | (2010.01) |
| ***C12P 21/02*** | (2006.01) |

(52) U.S. Cl.

CPC ............ *C07K 16/10* (2013.01); *C12N 5/0068* (2013.01); *C12N 5/0635* (2013.01); *C12P 21/02* (2013.01); *C12N 2533/40* (2013.01)

(58) Field of Classification Search

CPC . C12N 5/0635; C12N 2533/40; C12N 5/0068

See application file for complete search history.

(56) References Cited

U.S. PATENT DOCUMENTS

| | | | |
|---|---|---|---|
| 2009/0082486 | A1 | 3/2009 | Bates et al. |
| 2010/0279932 | A1 | 11/2010 | Ledbetter et al. |
| 2013/0136714 | A1 | 5/2013 | Wang et al. |
| 2018/0185463 | A1 | 7/2018 | Borriello |

OTHER PUBLICATIONS

Agarwal et al Synthetic Sustained Gene Delivery Systems, Current Topics in Medicinal Chemistry, 2008, 8, 311-330, published on Jun. 2008.*

Senapati et al Pentablock Copolymer Micelle Nanoadjuvants Enhance Cytosolic Delivery of Antigen and Improve Vaccine Efficacy while Inducing Low Inflammation, ACS Biomater. Sci. Eng. 2019, 5, 1332-1342, Published: Feb. 5, 2019.*

Agarwal et al Novel cationic pentablock copolymers as non-viral vectors for gene therapy, Journal of Controlled Release 103 (2005) 245-258, published on Dec. 19, 2004.*

International Search Report and Written Opinion in PCT/US21/36436, mailed Oct. 20, 2021, 13 pages.

Begum et al., "Analyses of spike protein from the first deposited sequences of SARS-CoV2 from West Bengal, India", F1000Research, May 18, 2020, vol. 9, No. 371, 13 pages.

Yang et al., "Nano-Star-Shaped Polymers for Drug Delivery Applications", Macromolecular Rapid Communications, Nov. 2017, vol. 38, No. 21, 26 pages.

* cited by examiner

*Primary Examiner* — Gregory Listvoyb

(74) *Attorney, Agent, or Firm* — McKee, Voorhees & Sease, PLC

(57) ABSTRACT

Compositions and methods are provided for rapid and efficient production of antibodies invitro as well as in vivo, which may be used to neutralize antigens. More specifically, the present invention relates to scaffolds comprised of amphiphilic multiblock copolymers that can form micelles based on nonionic or amphiphilic core blocks as well as ionic blocks, and with an antigen and methods of crosslinking B cell receptors to specifically produce antibodies against the antigen in vitro as well as in vivo in a more efficient method than other available monoclonal antibody production method.

25 Claims, 25 Drawing Sheets

PBC Micelle-anti-IgM F(ab)

NANOSCALE POLYMERIC MICELLAR SCAFFOLDS FOR RAPID AND EFFICIENT ANTIBODY PRODUCTION

CROSS REFERENCE TO RELATED APPLICATIONS

This application claims priority to provisional application U.S. Ser. No. 63/041,345, filed Jun. 19, 2020 which is incorporated herein by reference in its entirety.

GRANT REFERENCE

This invention was made with government support under Grant No. RO1AI141196, awarded by the National Institute of Health and Grant No. RO1AI127565, awarded by the National Institute of Health. The Government has certain rights in the invention.

FIELD OF THE INVENTION

The present invention relates to compositions and methods for rapid and efficient production of antibodies, preferably monoclonal antibodies, to neutralize antigens. More specifically, the present invention relates to polymeric micellar nanoscale scaffolds which, when combined with antigen, increase production of antigen-specific antibodies in vitro as well as in vivo through crosslinking of B cell receptors (BCR) and potentially other mechanisms.

BACKGROUND

Monoclonal antibodies (mAb) have garnered attention as therapeutics for treating different diseases including autoimmune diseases, cancer, and infectious diseases due to their higher specificity to an antigen (Ag) than a polyclonal antibody (pAb). Several methods for mAb production, both at bench-scale and large scale, in vitro or in vivo, have been utilized over the years. The most common method of generating monoclonal antibodies involves immunization of an animal multiple times with specific antigens, isolation of B cells from spleens of the immunized animals, fusion of the B cells with a myeloma cell, hybridoma production, screening for mAb with desired specificity, cloning, and expansion. However, these processes suffer from several limitations, including time required, high cost, reliance on animal use, and the possibility of contamination with murine pathogens if in vivo methods are used.

Adjuvants, such as polymers, water-in-oil micelles, squalene-based, alum, and CpG-ODN (i.e., TLR ligands), have been used in vivo to increase antibody production, generally though the amplifying the innate immune effects on the adaptive or antibody immune responses. In vivo, these adjuvants function through a variety of molecular mechanisms to increase the processing of an antigen and increase magnitude of the immune response in an organism. However, these mechanisms all work either through recruitment and activation of innate immune cells, such as dendritic cells or macrophages, or by the additional release of cytokines and chemokines to recruit and activate T cell mediated adaptive immunity. As the ability of adjuvants appear to work either through innate immunity or T cell mediated adaptive immunity, the use of adjuvants in vitro on populations of isolated B cells is unlikely to result in increased antibody production. Therefore, the amplifying antibody production property of traditional adjuvants cannot be relied upon for increased in vitro production of antibodies.

Antibodies may also be generated from expression vectors transfected into the appropriate cell line. However, the sequence of the Ab must be known first, the gene then needs to be cloned into an expression vector and, therefore, this method cannot be used to create de novo Abs to emerging infectious diseases which may have unknown antigenic regions.

Thus, there is a need to develop compositions and methods for rapid and more efficient production of antibodies, particularly in vitro, as well as in vivo and especially for emergent infectious diseases, such as COVID-19.

BRIEF SUMMARY

The present invention provides compositions and methods for rapid and efficient production of antibodies, in vitro as well as in vivo to identify and/or neutralize antigens. Nanoscale scaffolds combined with antigen may be used to activate and induce proliferation of B cells by crosslinking one or more B cell receptors (BCRs), allowing for the desired populations of B cells to expand and to produce large amounts of highly specific antibodies based upon the antigen.

Applicants have developed nanoscale block copolymer scaffolds. In a preferred embodiment, the block copolymer scaffolds preferably utilize an amphiphilic block copolymer based on a triblock of a nonionic or amphiphilic polymer core block flanked by two hydrophilic polymer blocks, the linking blocks. This triblock is then connected to two ionic blocks, resulting in the five individual blocks to form a pentablock copolymer (PBC). The PBC may undergo self-assembly in aqueous solutions at appropriate concentrations to form nanoscale micellar scaffolds in a temperature- and pH-responsive manner. Without being bound by any particular theory, these engineered nanoscale scaffolds may then interact with antigens in an electrostatic way through the ionic block. Once the antigen interacts with the PBC scaffold, it may be used to crosslink at least two B cell receptors (BCR) on B cells in vitro, leading to their activation, proliferation, and differentiation into antibody secreting cells.

In some embodiments, the polymer core block is nonionic. In other embodiments, the core block is amphiphilic. In some embodiments, the polymer core block is hydrophobic. In a preferred embodiment, the core block is polypropylene oxide (PPO) or polybutylene oxide (PBO). In a more preferred embodiment, the core block is PPO. In some embodiments, the core block will collapse in a pH- and temperature-dependent manner to form the scaffold units.

The linking blocks in some embodiments are nonionic. In other embodiments, the linking blocks are amphiphilic. In some embodiments, the two linking blocks are comprised of the same repeating unit. In other embodiments, the linking blocks are different repeating units. In a preferred embodiment, the linking blocks are polyethylene oxide (PEO).

In a preferred embodiment, the center triblock of the combined core block and the two linking blocks comprise a poloxamer. In an even more preferred embodiment, the combined core block and the linking blocks is poloxamer 407.

The ionic blocks may be cationic or anionic. One skilled in the art will appreciate that the ionic block should have the opposite charge as the antigen to facilitate the electrostatic interaction between the PBC based scaffolds and the antigen.

In a preferred embodiment, the ionic block units are substituted methacrylates. In a more preferred embodiment for polypeptide-based antigens, the ionic block units are cationic and include a tertiary amine methacrylate. In a preferred embodiment, the tertiary amine methacrylate is 2-(N, N-diethylaminoethyl methacrylate). In a preferred embodiment for anionic units, the methacrylate is substituted with acrylic acid, a sulfur, silicone, or phosphorus group.

B cells to be used with the PBC and antigen may be derived from spleens of an animal. In other embodiments, the B cells may be derived from the peripheral blood of humans or animals. In some embodiments, the animal is a mammal (e.g., cow). In preferred embodiments, the B cells are human derived. In some embodiments, the animal may be of an avian species.

B cells activated by the nanoscale scaffolds-antigen complexes may be used to produce antigen-specific antibodies quickly and efficiently by administering the scaffold-antigen complexes to a population of B cells in vitro. In further embodiments, the B cells may be treated with one or more additional compounds (e.g., BAFF) to increase proliferation, differentiation, and/or production of an antibody. In some embodiments the compound may be an anti-cluster of differentiation 40 (CD40) antibody or CD40L.

Once produced, the Abs or fragments may be used in any methodology for detection, diagnostics, purification, and treatment.

To enhance their use, the antibodies or fragments may be conjugated with a variety of compounds. To be used in a detection system, in some embodiments, the Abs or fragments are conjugated with a fluorophore or enzyme that may be detected in a system. In other embodiments, a secondary antibody, which is bonded to a fluorophore or enzyme, may bind to the antibody or fragment in a detection system.

In other embodiments, the Abs or fragments may be loaded onto adjuvants or nanoparticles to enhance their effectiveness when used as a therapy in vivo. The adjuvants or nanoparticles may allow the Abs or fragments to avoid degradation or be removed from circulation too quickly.

In yet another embodiment, the Abs or fragments may be provided in a kit for a detection system. The kit would include at least the antibodies or fragments for binding to the antigen in a sample and instructions for their use.

In an additional embodiment, the Abs or fragments may be used in a system to detect antigen in a sample.

While multiple embodiments are disclosed, still other embodiments of the present invention will become apparent to those skilled in the art from the following detailed descriptions, which show and describe illustrative embodiments of the invention. Accordingly, the figures and detailed description are to be regarded as illustrative in nature and not restrictive.

BRIEF DESCRIPTION OF THE DRAWINGS

FIG. 1F shows antibody titers in sera collected from saphenous vein bleeds from mice 2-weeks post-immunization for anti-HEL IgG (left) and anti-OVA IgG (right) showing rapid induction of a higher antibody titer in animals immunized with the PBC. Data are represented as mean±SEM. Data were analyzed using Kruskal-Wallis test for statistical significance followed by Mann-Whitney test for multiple comparisons, n=8 for FIGS. 1B and 1C and n=5 for FIGS. 1D, 1E and 1F, 1*s*=not statistically significant. Comparisons with p values shown only for groups of interest.

8C shows representative CFSE intensity for cells stimulated with various concentrations of PBC micelle-anti-IgM F(ab).

DETAILED DESCRIPTION

Figure 1A:
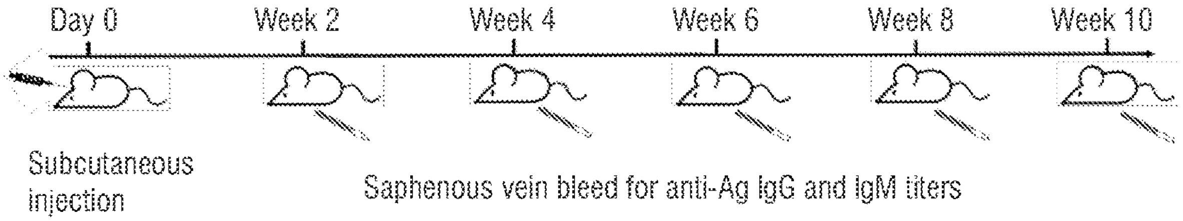
FIG. 1A shows an exemplary schematic of the in vivo experiment for subcutaneous immunization (e.g., nape of neck) of mice with PBC micelle (5 mg/100 μL dose), or monophosphoryl lipid A (MPLA, 10 μg/100 μL dose), or a combination of PBC micelle and MPLA, with either HEL or OVA (50 μg/dose).

Under normal usage, antibodies (Ab), i.e., immunoglobins (Ig), are proteins that are produced by B cells and secreted by plasma cells in response to the detection of a foreign substance in the body, an antigen (Ag). Antibodies in turn bind to the antigen to allow removal from the body.

B cells may produce various Ig isotypes. Initially, the Igs are inserted into the cellular membrane to serve as antigen receptors (B cell receptors, BCR) and belong to the IgM and IgD immunoglobin types. Each B cell clone produces a single form of the BCR, so each B cell may only recognize a limited number of cross-reacting antigens and some B cells may only be able to recognize a single antigen. Once an antigen binds to the BCR, the B cell may proliferate and differentiate into an effector cell. The binding of the BCR causes a change to the Igα/Igβ invariant chains to activate Src-like kinase, which relays the signal downstream and aids in the proliferation and differentiation. Typically, a B cell will need additional signaling in addition to the binding of the BCR for antibody production. This additional signaling is typically provided by the CD40 ligand, found on the surface of T cells or lymphocytes, binding to the CD40 receptor on the surface of the B cell. The effector B cell may then differentiate into a plasma cell that will secrete large amounts of soluble Ig, which is the antibody, and generally belong to the IgM, IgG, IgE, or IgA immunoglobin isotypes.

When used in vivo, an adjuvant along with an antigen confer immunity to a subject which may result in an increase in antigen-specific antibody production by the adaptive immune system. However, evidence suggests that the way in which adjuvants achieve this increase in antibody production is through the initial activation of the innate immune system or T cells. For example, it is thought that polymer-based adjuvants increase the response of the innate immune system by allowing a slow release of antigen. This slow release allows for a longer exposure of the innate immune system, which allows a higher number of cells to interact with the antigen. The innate immune system then activates B cells downstream of the initial actions of the adjuvant. Therefore, adjuvants, while providing a beneficial effect in an in vivo model where all cell types are available for the complex pathways of activating B cells to produce antibodies, they are not expected to provide the same benefit in an in vitro cell culture comprised solely of naive B cells, with some not even expected to enhance antibody production even with a mix of B cells and T cells in vitro.

The embodiments of this invention are not limited to particular methods of selection, methods of production, and compositions, which can vary and may be understood by skilled artisans.

In order to provide a clear and consistent understanding of the specification and the claims, including the scope given to such terms, the following definitions are provided. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

As used herein, the term "antigen" or "Ag" is any molecule, either organic or inorganic, biologic, or chemical, may bind to an antibody, B cell receptor, or other molecule induced by an adaptive immune response. As disclosed herein, the block copolymers allow antigens that are not immunogenic to effectively cross-link the BCR.

As "immunogen" is any molecule, either organic or inorganic, biologic, or chemical, that is capable of inducing an adaptive immune response.

As used herein, the term "B cell receptor" or "BCR" refers to the transmembrane immunoglobulin protein on the surface of a B cell that serves as its antigen-specific receptor.

As used herein, the term "antigenic determinant" refers to the specific region of an antigen that binds to an antibody or a complementary receptor on the surface of a B cell, the BCR, or T cell, the T cell receptor or TCR. As used herein antigenic determinant and "epitope" are used interchangeably.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology but is not necessarily translated from a designated nucleic acid sequence. It may be generated in any manner, including by chemical synthesis.

Also included as polypeptides of the present invention are fragments, derivatives, analogs, or variants of the foregoing polypeptides, and any combination thereof.

The terms "fragment," "variant," "derivative" and "analog" when referring to antibodies or antibody polypeptides of the present invention include any polypeptides which retain at least some of the antigen-binding properties of the corresponding native binding molecule, antibody, or polypeptide.

Fragments of polypeptides include proteolytic fragments, as well as deletion fragments, in addition to specific antibody fragments discussed elsewhere herein. Variants of antigens and antigenic polypeptides and antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions, or additions. Examples include fusion proteins.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Variant polypeptides may also be referred to herein as "polypeptide analogs". As used herein a "derivative" of a binding molecule or fragment thereof, an antibody, or an antibody polypeptide refers to a subject polypeptide having a residue chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide is RNA, for example, in the form of messenger RNA (mRNA).

As used herein, a "binding molecule" relates primarily to antigens or antibodies, and fragments thereof, but may also refer to other non-antigen or non-antibody molecules including but not limited to hormones, receptors, ligands, major histocompatibility complex (MHC) molecules, chaperones such as heat shock proteins (HSPs) as well as cell-cell adhesion molecules such as members of the cadherin, integrin, C-type lectin and immunoglobulin (Ig) superfamilies. Thus, for the sake of clarity only and without restricting the scope of the present invention most of the following embodiments are discussed with respect to antigens or antibodies and antibody-like molecules which represent the preferred binding molecules for the development of therapeutic and diagnostic agents.

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\varepsilon$) with some subclasses among them (e.g., $\gamma1$-$\gamma4$). It is the nature of this chain that determines the "class" of the antibody as IgG, IgM, IgA, IgD, or IgE, respectively. The immunoglobulin subclasses (isotypes) e.g., IgG1, IgG2, IgG3, IgG4, IgAQ1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, Antibodies or antigen-binding fragments, immunospecific fragments, variants, fusion proteins, or derivatives thereof of the invention include, but are not limited to, polyclonal, monoclonal, multispecific, human, humanized, primatized, murinized or chimeric antibodies, single chain antibodies, epitope-binding fragments, e.g., Fab, Fab' and $F(ab')_2$, Fd, Fvs, single-chain Fvs (scFvs), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgAQ1 and IgA2) or subclass of immunoglobulin molecule.

In a preferred embodiment, the antibody of the present invention is not a polyclonal antibody, i.e., it substantially consists of one particular antibody species rather than being a mixture obtained froth a plasma immunoglobulin sample. In a particularly preferred embodiment, the antibody is a monoclonal antibody.

Antibody fragments, including single-chain antibodies, may comprise the variable region(s) alone or in combination with the entirety or a portion of the following: hinge region, CH1, CH2, and CH3 domains. Antibodies or immunospecific fragments thereof of the present invention may be from any animal origin including birds and mammals. Preferably, the origin of the antibodies may be from human, murine, donkey, rabbit, goat, guinea pig, camel, llama, horse, or chicken. In another embodiment, the variable region may be condricthoid in origin (e.g., from sharks).

In one aspect, the antibody of the present invention is a human monoclonal antibody isolated from a human. Optionally, the framework region of the human antibody is aligned and adopted in accordance with the pertinent human germ line variable region sequences in the database; see, e.g., Vbase (http://vbase.mrc-cpe.cam.ac.uk/) hosted by the MRC Centre for Protein Engineering (Cambridge, UK). For example, amino acids considered to potentially deviate from the true germ line sequence could be due to the PCR primer sequences incorporated during the cloning process. Compared to artificially generated human-like antibodies such as single chain antibody fragments (scFvs) from a phage displayed antibody library or xenogeneic mice the human monoclonal antibody of the present invention is characterized by (i) being obtained using the human immune response rather than that of animal surrogates, i.e. the antibody has been generated in response to natural antigen in its relevant conformation in the human body, (ii) having protected the individual or is at least significant for the presence of antigen, and (iii) since the antibody is of human origin the risks of cross-reactivity against self-antigens is minimized. Thus, in accordance with the present invention the terms "human monoclonal antibody", "human monoclonal autoantibody", "human antibody" and the like are used to denote an antigen binding molecule which is of human origin, i.e. which has been isolated from or secreted by a human cell such as a B cell or hybridoma thereof or the cDNA of which has been directly cloned from mRNA of a human cell, for example a human memory B cell. A human antibody is still "human" even if amino acid substitutions are made in the antibody, e.g., to improve binding characteristics.

Antibodies derived from human immunoglobulin libraries or from animals transgenic for one or more human immunoglobulins and that do not express endogenous immunoglobulins, as described infra and, for example in, U.S. Pat. No. 5,939,598 by Kucherlapati et al., are denoted human-like antibodies in order distinguish them from truly human antibodies of the present invention.

Preferred embodiments of the invention are to create the antibodies or fragments in the organism in which the antibody is meant to be used as a diagnostic or treatment. For example, human antibodies or fragments made from human subjects.

In other aspects of the invention, an antibody may be raised in a first organism and then modified to be more similar to a different organism, such as a murinized or humanized antibody.

By "specifically binding", or "specifically recognizing", used interchangeably herein, it is generally meant that a binding molecule, e.g., an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D".

Where present, the term "immunological binding characteristics," or other binding characteristics of an antibody with an antigen, in all its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

A binding molecule, e.g., an antibody or antigen-binding fragment, variant, or derivative disclosed herein may be said to an antigen or a fragment, such as an isolate antigenic determinant region, or variant thereof with an off rate (k(off)) of less than or equal to $5\times10^{-2}$ $sec^{-1}$, $10^{-2}$ $sec^{-1}$, $5\times10^{-3}$ $sec^{-1}$, or $10^{-3}$ $sec^{-1}$. More preferably, an antibody of the invention may be said to bind an antigen or a fragment or variant thereof with an off rate (k(off)) less than or equal to $5\times10^{-4}$ $sec^{-1}$, $10^{-4}$ $sec^{-1}$, $5\times10^{-5}$ $sec^{-1}$, or $10^{-5}$ $sec^{-1}$, $5\times10^{-6}$ $sec^{-1}$, $10^{-6}$ $sec^{-1}$, $5\times10^{-7}$ $sec^{-1}$ or $10^{-7}$ $sec^{-1}$.

A binding molecule, e.g., an antibody or antigen-binding fragment, variant, or derivative disclosed herein may be said to bind an antigen or a fragment or variant thereof with an on rate (k(on)) of greater than or equal to $10^3$ $M^{-1}$ $sec^{-1}$, $5\times10^3$ $M^{-1}$ $sec^{-1}$, $10^4$ $M^{-1}$ $sec^{-1}$ or $5\times10^4$ $M^{-1}$ $sec^{-1}$. More preferably, an antibody of the invention may be said to bind an antigen or a fragment or variant thereof with an on rate (k(on)) greater than or equal to $10^5$ $sec^{-1}$, $5\times10^5$ $M^{-1}$ $sec^{-1}$, $10^6$ $M^{-1}$ $sec^{-1}$, or $5\times10^6$ $M^{-1}$ $sec^{-1}$ or $10^7$ $M^{-1}$ $sec^{-1}$.

A binding molecule, e.g., an antibody or antigen-binding fragments, variants, or derivatives thereof, is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of a binding molecule, e.g., an immunoglobulin molecule; see, e.g., Harlow et al., Antibodies: A Laboratory Manual, Cold Spring Harbor Laboratory Press, 2nd ed. (1988) at pages 27-28.

Binding molecules, e.g., antibodies or antigen-binding fragments, variants, or derivatives thereof, of the invention may also be described or specified in terms of their cross-reactivity. As used herein, the term "cross-reactivity" refers to the ability of an antibody, specific for one antigen, to react with a second antigen: a measure of relatedness between two different antigenic substances. Thus, an antibody is cross reactive if it binds to an epitope other than the one that induced its formation. The cross-reactive epitope generally contains many of the same complementary structural features as the inducing epitope, and in some cases, may fit better than the original.

As used herein, the terms "linked," "fused" or "fusion" are used interchangeably. These terms refer to the joining of two more elements or components; by whatever means including chemical conjugation or recombinant means. Art "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

As used herein, the term "sample" refers to any biological material obtained from a subject or patient. In one aspect, a sample can comprise blood or serum, cerebrospinal fluid ("CSF"), or urine. In other aspects, a sample can comprise whole blood, plasma, B cells enriched from blood samples, and cultured cells (e.g., B cells from a subject). A sample can also include a biopsy or tissue sample including neural tissue. In still other aspects, a sample can comprise whole cells and/or a lysate of the cells. Blood samples can be collected by methods known in the art.

As used herein, the terms "treat" or "treatment" refer to both therapeutic treatment and prophylactic or preventative measures, wherein the object is to prevent or slow down (lessen) an undesired infection. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

By "subject" or "individual" or "animal" or "patient" or "mammal," is meant any subject, particularly a mammalian subject, e.g., a human patient, for whom diagnosis, prognosis, prevention, or therapy is desired.

The term "sufficient amount of time," as used herein, refers to the time it takes for a compound, material, composition comprising a compound of the present invention, or an organism which is effective for producing some desired effect in at least a sub-population of cells.

As used herein, "substantially free" may refer to any component that the composition of the invention lacks or mostly lacks. When referring to "substantially free" it is intended that the component is not intentionally added to compositions of the invention. Use of the term "substantially free" of a component allows for trace amounts of that component to be included in compositions of the invention because they are present in another component. However, it is recognized that only trace or de minimus amounts of a component will be allowed when the compositions is said to be "substantially free" of that component. Moreover, the term if a composition is said to be "substantially free" of a component, if the component is present in trace or de minimus amounts it is understood that it will not affect the effectiveness of the compositions. It is understood that if an ingredient is not expressly included herein or its possible inclusion is not stated herein, the invention composition may be substantially free of that ingredient. Likewise, the express inclusion of an ingredient allows for its express exclusion thereby allowing a composition to be substantially free of that expressly stated ingredient.

Antigen

The present invention generally relates to any human or animal antigen which may be recognized by a BCR. This can include proteins found on the surfaces of cells, viruses, fungi, or bacteria. It may also include compounds such as toxins, chemicals, drugs, and foreign particles. Antigens may also include improperly folded proteins or tumor antigens found within a subject.

An antigen may be an exogenous, endogenous, autoantigen, or neoantigen (e.g., tumor associated antigen). In preferred embodiments the antigen is an exogenous, exogenous antigens which have become endogenous, or neoantigen. More preferably, the antigen is a viral, bacterial, fungal, or parasitic antigen, but not limited to those and can include other antigens such as tumor antigens or allergens. The antigen may be used as a whole, for example an intact viral coat, or a fragment thereof, such as the antigenic determinant or epitope, may be used.

The antigen may be labeled with a fluorescent dye for later detection using methods known in the art.

PBC Scaffolds of the Invention

The scaffolds of the invention are engineered to be an amphiphilic linear multiblock copolymer. In some preferred embodiments, the multiblock copolymer is a triblock, a pentablock copolymer, nonablock copolymer, or a trideca-block. In an even more preferred embodiment, the multi-block copolymer is a pentablock copolymer (PBC). For example, a PBC may comprise two outer ionic blocks, two hydrophilic nonionic or amphiphilic linker blocks, and a single nonionic or amphiphilic core block. Other multiblock copolymers may be intermediates of the preferred blocks, for example a tetrablock may comprise of an outer ionic block, two hydrophilic nonionic or amphiphilic linkers, and a single nonionic or amphiphilic core block. The ionic block may be the same or different and the linker block may also be the same or different. The block copolymers need to have low cytotoxicity, have sufficient length and/or flexibility to allow bound antigens to crosslink at least two BCRs, and will self-assemble at tolerable pH and temperatures. Tolerable pH range may be between about 6.8 to about 7.6, but more preferably between about 7.2 and about 7.4. Tolerable temperature may range from about 35° C. to about 40° C., more preferably from about 36° C. to about 37° C.

Core Block

The core block of the block copolymer is preferably a hydrophobic non-ionic or amphiphilic polymer and contributes to the self-assembly of the PBC and the overall length of the PBC. The core block is also preferably non-cytotoxic. The core block may comprise from about 1 to about 20,000 repeat units, from about 10 to about 1,000 repeat units, or from about 20 to about 100 repeat units, wherein the units may include, but are not limited to, propylene oxide (PO), butylene oxide (BO), dimethylsiloxane (DMS), 8-caprolactone (CL), L-lactide, lactide-co-glycolic acid (LGA), L-aspartic acid (Asp), L-histidine (His), 3-amino ester (bAE), and/or disteroyl phosphatidyl ethanolamine (DSPE). Preferably the unit is PO or BO. Most preferably, the unit is PO.

Linker Block

The linker blocks, flanking either side of the core block and connecting the core block to the ionic blocks, is preferably a hydrophilic non-ionic or amphiphilic polymer and contributes to the length, flexibility, and water solvency of the scaffolds. The linker blocks are preferably non-cytotoxic. The linker blocks may comprise from about 10 to about 20,000 repeat units, from about 40 to about 1,000 repeat units, or from about 40 to about 500 repeat units, wherein the units may include, but are not limited to, ethylene oxide (EO), N-vinyl pyrrolidone (VP), and/or N-isopropyl acrylamide (NIPAAm). Preferably the unit is EO.

In some embodiments the two linker blocks are comprised of the same units. In other embodiments, the linker blocks are comprised of different units. Preferably the two linker blocks are the same length and the same unit.

In some embodiments the linker is attached linearly to the core block. In other embodiments the linker is attached as a pendent to the core block. Preferably, the attachment is linear.

If the core block comprises PPO and linker blocks comprise PEO, they may be purchased commercially already combined as poloxamers. In a preferred embodiment, the poloxamer is poloxamer 407, sold commercially as Pluronic® F-127 from BASF or Synperonic PE/F 127 from Croda. Poloxamer 407 comprises 56 units of PO flanked on each side by 101 units of EO, being about 70% EO, and has a molecular weight of about 3,600 to about 4,000 Daltons. Poloxamer 407 has the general formula:

(I)

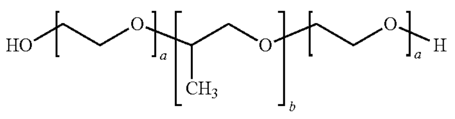

where A is 101 and B is 56.

Ionic Block

Without being bound by a particular theory, it is believed that the ionic block provides the electrostatic interaction with the antigen. As such, one skilled in the art will appreciate that the ionic block should have the opposite charge as the antigen. In some embodiments, the ionic blocks are cationic. In other embodiments, the ionic blocks are anionic. In a preferred embodiment, the ionic block is a substituted methacrylate. If the ionic block is a substituted methacrylate, it may be represented by the following formula:

(II)

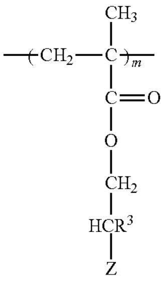

where $R^3$ is either a hydrogen or a $C_{1-6}$ alkyl group;

where Z are selected from the group of $NR^6R^7$, $P(OR^8)_3$, $SR^9$, SH,

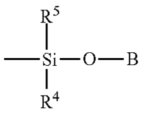

and

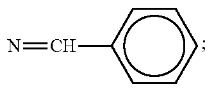

;

in which $R^4$, $R^5$, $R^6$, $R^7$, and $R^8$, are either the same or different hydrogen or a $C_{1-6}$ alkyl group and $R^9$ is a tri($C_{1-6}$ alkyl) silyl group, and B is a $C_{1-6}$ alkyl group; and where m is a number in the range of about 1 to about 5,000.

In a more preferred embodiment for polypeptide-based antigens, the ionic block is cationic and a tertiary amine methacrylate. In a preferred embodiment, the tertiary amine methacrylate is 2-(N,N-diethylaminoethyl methacrylate, DEAEM). In a preferred embodiment for anionic blocks, the methacrylate is substituted with a sulfur, silicone, or phosphorus group.

When combined with a preferred linker blocks and core block, a preferred embodiment may be represented by the following formula:

(III)

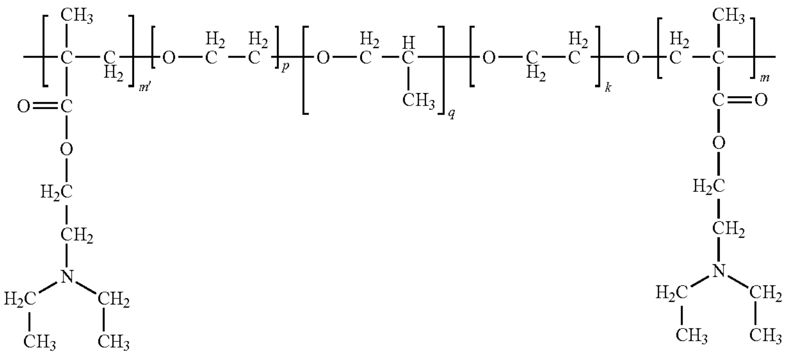

where m and m' is a number in the range of about 1 to about 5,000;

p and k is a number in the range of about 10 to about 20,000; and q is a number in the range of about 1 to about 20,000.

Alternatively, a preferred embodiment may be represented by the following formula:

(IV)

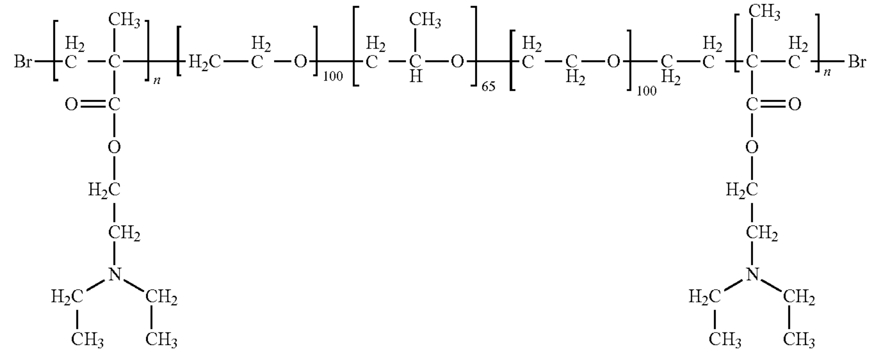

In a more preferred embodiment p and k are 101 and q is 56, representing poloxamer 407. In another preferred embodiment, p and k are 20 and q is 70, representing Pluronic P123.

Optional Side Functionalization

The ionic block may be further substituted to add additional functions. By way of nonlimiting example, the final carbon of the block may be halogenated during the process of combining the ionic block to the linker block. This halogen may then be reacted to further functionalize the ionic block. For example, the halogen may be substituted with an azide linker added by reacting the PBC with sodium azide as described in Adams et al. (Adams J R, Goswami M, Pohl N L B, Mallapragada, SK, Synthesis and functionalization of virus-mimicking cationic block copolymers with pathogen-associated carbohydrates as potential vaccine adjuvants. *RSC Adv.,* 2014; 4(30):15655; doi:10.1039/c3ra47687a, herein incorporated by reference in its entirety). Different groups, such as sugars like D-mannose or fluorescent dyes with an alkyne linker, may then be linked to the PBC by an azide-alkyne Huisgen cycloaddition, also known as "click chemistry".

The additional functionalization may also be used to add antigens that may not interact through electrostatics with the ionic block to the PBC. For example, a nonionic drug may have an alkyl linker added and then reacted with the azide linker to form the PCB-antigen combination. This further extends the possible antigens that may be used in conjunction with the PBC for B cell activation.

Cytotoxicity

Cytotoxicity may be assessed by any means known in the art, such as those identified in ISO 10993-5. For example, extract tests, such as methyl thiazolyl tetrazolium (MTT), direct contact tests, cell growth inhibition tests, ultraviolet spectrophotometer assays, cell rehabilitation methods, degree of cell proliferation assays, cell morphology observations, may all be used to assay cytotoxicity.

Additionally, the measurements of various molecular markers may be used. Assaying such molecular markers, such as proto-oncogenes and tumor-suppressor gene inactivation, apoptosis related genes, such as NF-κB, may all be used. Measuring levels of these markers are known to those skilled in the art and may include polymerase chain reaction to measure changes in RNA expression, or Western Blotting, ELISA, or immunohistochemistry to measure protein expression changes.

Cultured B cell viability after the administration of the PBC based scaffolds may be about 30% or greater, about 40% or greater, about 50% or greater, or about 60% or greater.

Methods of Making Exemplary PBCs

The PBCs may be made by any method known to the art. By way of nonlimiting example, a preferred pentablock copolymer (PDEAEM-PEO-PPO-PEO-PDEAEM) may be synthesized by atom transfer radical polymerization (ATRP) as taught in U.S. Pat. No. 7,217,776 (herein incorporated in its entirety) or Determan et al. (Determan M D, Cox J P, Seifert S, Thiyagarajan P, Mallapragada S K, Synthesis and characterization of temperature and pH-responsive pentablock copolymers, *Polymer,* 2005; 46:6933-6946; doi: 10.1016/j.polymer.2005.05.138, herein incorporated in its entirety).

By way of nonlimiting example, some PBCs may be made by dissolving the linker block and core block, such as a poloxamer, in tetrahydrofuran and then reacted with triethylamine and 2-bromoisobutyryl from about 4 to about 20 hours, from about 6 to about 16 hours, or from about 8 to about 16 hours. The product may then be precipitated out in an organic solvent, such as n-hexane. Atomic transfer radical polymerization (ATRP) may then be used to react the 2-bromo propionate poloxamer product with monomers of the ionic block, for example DEAEM, to synthesize the pentablock copolymer using copper (I) oxide nanoparticles as a catalyst and N-propylpyrilidinemethanamine (NPPM) as the complexing ligand. This process may also result in the final ionic block being brominated. The cuprous oxide nanoparticles may be synthesized as described in Adams et al. (Adams J R, Mallapragada S K, Novel Atom Transfer Radical Polymerization Method to Yield Copper-Free Block Copolymeric Biomaterials, Macromol Chem Phys, 2013; 214(12)1321-1325, doi:10.1002/macp.201300034, herein incorporated by reference in its entirety). To further functionalize the PBC, the brominated PBC may be reacted with sodium azide at 50° C. for about 4 hours, for about 12 hours, or for about 24 hours. The product may then be extracted in an organic solvent, such as n-hexane, and then dried in an oven.

To form the scaffolds, the PBC may be added to an aqueous solution, preferably phosphate buffered solution (PBS) for use in in vitro B cell activation. The final concentration of PBC is typically from about 0.5 to about 10 wt % to achieve the critical micelle concentration (CMC). Higher concentrations of the PBC in the aqueous solution may result in the formation of a hydrogel instead of scaffolds, depending on the temperature. If a hydrogel does form, additional aqueous solvent may be added in a sufficient amount to dilute the solution to just above the CMC and allowed to form the micellar scaffolds form instead.

The PBC may be labeled prior to integration into the scaffolds by first functionalizing the end groups with azide and then attaching an alkyne functionalized dye according to methods known in the art.

Cells

Any population of B cells may be used in the methods of the invention. In some embodiments, the population of B cells are immature primary B cells extracted from spleen. In other embodiments the B cells may be extracted from peripheral blood. Any methods of extraction and culture are known in the art may be used. The B cells may be of any human or animal origin. Preferably, but not limited to, the B cells may originate from human, murine, donkey, rabbit, goat, guinea pig, camel, llama, horse, or chicken spleens or from peripheral blood. If the origin of the B cells is from a different organism than the subject to treat, the resulting antibodies may be altered to conform to the subject's species. For example, if the spleen is derived from a mouse, the resulting antibodies may be humanized to be used to treat human subjects. Preferably, the B cells are derived from human peripheral blood to avoid the need to humanize antibodies, and to allow for direct induction of human antibodies in vitro using the approach described here.

In still other embodiments, the cells are immortalized. Primary B cells are traditionally immortalized by infection of Epstein Bar Virus (EBV) into lymphoblastoid cells (LC) lines. This suggest that activate Ras oncogene may immortalize B cells, as such, the overexpression of Ras oncogenes, such as using an expression vector, within the B cells may also immortalize them to continue producing desired antibodies. The antigen-specific B cells could also be fused with a myeloma cell to generate a hybridoma secreting the antibody of interest sing methods known in the art.

In the well-known hybridoma process (Kohler et al., Nature 256 (1975), 495) the relatively short-lived, or mortal, lymphocytes from a mammal, e.g., spleen cells derived from a mouse, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic clones by selection, dilution, and re-growth with each individual clone comprising specific genes for the formation of an antibody with a single specificity. They produce antibodies, which are homogeneous against a desired antigen and, in reference to their pure genetic parentage, are termed "monoclonal".

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection, and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods; see, e.g., Goding, Monoclonal Antibodies: Principles and Practice, Academic Press, pp 59-103 (1986). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Antibodies

The present invention also relates to antibodies produced by the B cells. In one embodiment, the present invention is directed to an antibody produced by B cells crosslinked by the scaffold-antibody complex, or antigen-binding fragment, variant, or derivatives thereof, where the antibody specifically binds to the same epitope as the reference antibodies.

Due to its specificity of the antibodies of the present invention, the antibodies will recognize epitopes which are of particular physiological relevance, such as an infectious disease or cancer state. As such, the binding of the antibodies of the present invention may be used in competition with other antibodies, such as commercial antibodies. Competition between antibodies may be determined, for examples, by an assay in which the immunoglobulin under test inhibits specific binding of a reference antibody to a common antigen, such as virus. Numerous types of competitive binding assays are known, for example: solid phase direct or indirect radioimmunoassay (RIA), solid phase direct or indirect enzyme immunoassay (ETA), sandwich competition assay, enzyme immuno assay (EIA); see Stahli et al., Methods in Enzymology 9 (1983), 242-253; solid phase direct biotin-avidin EIA; see Kirkland et al., J. Immunol. 137 (1986), 3614-3619 and Cheung et al., Virology 176 (1990), 546-552; solid phase direct labeled assay, solid phase direct labeled sandwich assay; see Harlow and Lane, Antibodies, A Laboratory Manual, Cold Spring Harbor Press (1988); solid phase direct label RIA using $I^{125}$ label; see Morel et al, Molec. Immunol. 25 (1988), 7-15 and Moldenhauer et al., Scand. J. Immunol. 32 (1990), 77-82, all incorporated herein in their entirety. Typically, such an assay involves the use of purified antigen bound to a solid surface or cells or virions bearing the antigen, an unlabeled test immunoglobulin and a labeled reference immunoglobulin, i.e., a monoclonal antibody of the present invention. Competitive inhibition is measured by determining the amount of label bound to the solid surface or cells in the presence of the test immunoglobulin. Usually, the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% or 75%. Hence, the present invention is further drawn to an antibody, or antigen-binding fragment, variant, or derivatives thereof, where the antibody competitively inhibits a reference antibody selected from the antibodies illustrated in the Examples from binding to αSyn.

In another embodiment, the present invention provides an isolated polypeptide comprising, consisting essentially of or consisting of an immunoglobulin heavy chain variable region ($V_H$) or light chain variable region ($V_L$, together V), where at least one of V-CDRs of the heavy or light chain variable region or at least two of the V-CDRs of the heavy or light chain variable region are at least 80%, 85%, 90% or 95% identical to reference heavy or light chain V-CDR1, V-CDR2 or V-CDR3 amino acid sequences from the antibodies created from the activated B cells. Alternatively, the V-CDR1, V-CDR2 and V-CDR3 regions of the V are at least 80%, 85%, 90% or 95% identical to reference heavy chain V-CDR1, V-CDR2 and V-CDR3 amino acid sequences from the antibodies created by the activated B cells.

In another embodiment, the present invention provides an isolated polypeptide comprising, consisting essentially of, or consisting of an immunoglobulin variable region (V) of the light and/or heavy chain in which the V-CDR1, V-CDR2 and V-CDR3 regions have polypeptide sequences which are identical to the V-CDR1, V-CDR2 and V-CDR3 groups of the antibodies created by the activated B cells.

In another embodiment, the present invention provides an isolated polypeptide comprising, consisting essentially of, or consisting of an immunoglobulin variable region (V) of the heavy or light chain in which the V-CDR1, V-CDR2 and V-CDR3 regions have polypeptide sequences which are identical to the V-CDR1, V-CDR2 and V-CDR3 groups of the antibodies created herein, except for one, two, three, four, five, or six amino acid substitutions in any one V-CDR. In certain embodiments the amino acid substitutions are conservative.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO00/30680 for corresponding technical details.

Additionally, the present invention encompasses peptides including those containing a binding molecule as described above, for example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides may easily be synthesized or produced by recombinant means to produce a binding agent useful according to the invention. Such methods are well known to those of ordinary skill in the art. Peptides can be synthesized for example, using automated peptide synthesizers which are commercially available. The peptides can also be produced by recombinant techniques by incorporating the DNA expressing the peptide into an expression vector and transforming cells with the expression vector to produce the peptide.

The present invention further relates to any binding molecule, e.g., an antibody or binding fragment thereof which is oriented towards antibodies of the present invention and display the mentioned properties, i.e., created from B cells activated by PMC scaffold-antigen complexes. Such antibodies and binding molecules can be tested for their binding specificity and affinity by methods known in the art such as, but not limited to, ELISA and Western Blot and immunohistochemistry.

As an alternative to obtaining immunoglobulins directly from the culture of activated B cells derived from peripheral blood or spleen, the immunoglobulins or antibodies may be obtained from the culture of immortalized B cells, B memory cells, or hybridomas. The immortalized cells may also be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward.

Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells may be used for efficient processing, for example mammalian or bacterial cells. Typical mammalian cell lines useful for this purpose include, but are not limited to, CHO cells, HEK 293 cells, or NSO cells.

The production of the antibody or analog is then undertaken by culturing the modified recombinant host under culture conditions appropriate for the growth of the host cells and the expression of the coding sequences. The antibodies are then recovered by isolating them from the culture. The expression systems are preferably designed to include signal peptides so that the resulting antibodies are secreted into the medium; however, intracellular production is also possible.

Antibodies, or antigen-binding fragments, variants, or derivatives thereof also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In particular preferred embodiments, antibodies, or antigen-binding fragments, variants, or derivatives thereof of the invention will not elicit a deleterious immune response in the animal to be treated, e.g., in a human.

De-immunization can also be used to decrease the immunogenicity of an antibody. As used herein, the term "de-immunization" includes alteration of an antibody to modify T cell epitopes; see, e.g., international applications WO98/52976 and WO00/34317. For example, $V_H$ and $V_L$ sequences from the starting antibody are analyzed and a human T cell epitope "map" from each V region showing the location of epitopes in relation to complementarity determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

In another embodiment, the activated B lymphocytes can be selected by micromanipulation and the variable genes isolated. The cultures of the activated B cells can be screened for specific immunoglobins, such as IgGs or IgMs, that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines created by the in vitro methods described herein may be selected and cultured using techniques well known to the skilled artisan. Such techniques are described in a variety of laboratory manuals and primary publications. In this respect, techniques suitable for use in the invention as described below are described in Current Protocols in Immunology, Coligan et al., Eds., Green Publishing Associates and Wiley-Interscience, John Wiley and Sons, New York (1991) which is herein incorporated by reference in its entirety, including supplements.

Antibody fragments that recognize specific epitopes may be generated by known techniques. For example, Fab and $F(ab')_2$ fragments may be produced recombinantly or by proteolytic cleavage of immunoglobulin molecules, using enzymes such as papain (to produce Fab fragments) or pepsin (to produce $F(ab')_2$ fragments). $F(ab')_2$ fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes.

In one embodiment, an antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments, a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody. Domain deleted constructs can be derived using a vector encoding an $IgG_1$ human constant domain, see, e.g., international applications WO02/060955 and WO02/096948A2. This vector is engineered to delete the CH2 domain and provide a synthetic vector expressing a domain deleted $IgG_1$ constant region.

In certain embodiments, antibodies, or antigen-binding fragments, variants, or derivatives thereof of the present invention are minibodies. Minibodies can be made using methods described in the art, see, e.g., U.S. Pat. No. 5,837,821 or international application WO 94/09817.

In one embodiment, an antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the CH2 domain may be enough to substantially reduce Fc binding and thereby increase antigen localization. Similarly, it may be desirable to simply delete that part of one or more constant region domains that control the effector function (e.g., complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

The present invention also provides antibodies that comprise, consist essentially of, or consist of, variants (including derivatives) of antibody molecules (e.g., the $V_H$ regions and/or $V_L$ regions) described herein, which antibodies or fragments thereof immunospecifically bind to aggregate αSyn. Standard techniques known to those of skill in the art can be used to introduce mutations in the nucleotide sequence encoding an antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$-CDR1, $V_H$-CDR2, $V_H$-CDR3, $V_L$ region, $V_L$-CDR1, $V_L$-CDR2, or $V_L$-CDR3. Introduced mutation may be conservative mutations. Alternatively, mutations can be introduced randomly along all or part of the coding sequence, such as by saturation mutagenesis, and the resultant mutants can be screened for biological activity to identify mutants that retain activity.

Fusion Proteins and Conjugates

In certain embodiments, the antibody polypeptide comprises an amino acid sequence or one or more moieties not normally associated with an antibody. Exemplary modifications are described in more detail below. For example, a single-chain Fv antibody fragment of the invention may comprise a flexible linker sequence, or may be modified to add a functional moiety (e.g., PEG, a drug, a toxin, or a label such as a fluorescent, radioactive, enzyme, nuclear magnetic, heavy metal, and the like)

An antibody polypeptide of the invention may comprise, consist essentially of, or consist of a fusion protein. Fusion proteins are chimeric molecules which comprise, for example, an immunoglobulin antigen-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

As discussed in more detail elsewhere herein, antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, antibodies may be recombinantly fused or conjugated to molecules useful as labels in detection assays and effector molecules such as heterologous polypeptides, drugs, radionuclides, or toxins; see, e.g., international applications WO92/08495; WO91/14438; WO89/12624; U.S. Pat. No. 5,314,995; and European patent application EP 0 396 387.

Antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. Antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification may be present in the same or varying degrees at several sites in a given antibody. Also, a given antibody may contain many types of modifications. Antibodies may be branched, for example, as a result of ubiquitination, and they may be cyclic, with or without branching. Cyclic, branched, and branched cyclic antibodies may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., Proteins—Structure And Molecular Properties, T. E. Creighton, W. H. Freeman and Company, New York 2nd Ed., (1993); Posttranslational Covalent Modification Of Proteins, B. C. Johnson, Ed., Academic Press, New York, pgs. 1-12

(1983); Seifter et al., Meth. Enzymol. 182 (1990), 626-646; Rattan et al., Ann. NY Acad. Sci. 663 (1992), 48-62).

The present invention also provides for fusion proteins comprising an antibody, or antigen-binding fragment, variant, or derivative thereof, and a heterologous polypeptide. In one embodiment, a fusion protein of the invention comprises, consists essentially of, or consists of, a polypeptide having the amino acid sequence of any one or more of the $V_H$ regions of an antibody of the invention or the amino acid sequence of any one or more of the $V_L$ regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the $V_H$-CDRs of an antibody, or fragments, variants, or derivatives thereof, or the amino acid sequence of any one, two, three of the $V_L$-CDRs of an antibody, or fragments, variants, or derivatives thereof, and a heterologous polypeptide sequence. In one embodiment, the fusion protein comprises a polypeptide having the amino acid sequence of a $V_H$-CDR3 of an antibody of the present invention, or fragment, derivative, or variant thereof, and a heterologous polypeptide sequence, which fusion protein specifically binds to an antigen. In another embodiment, a fusion protein comprises a polypeptide having the amino acid sequence of at least one $V_H$ region of an antibody of the invention and the amino acid sequence of at least one $V_L$ region of an antibody of the invention or fragments, derivatives, or variants thereof, and a heterologous polypeptide sequence. Preferably, the $V_H$ and $V_L$ regions of the fusion protein correspond to a single source antibody (or scFv or Fab fragment) which specifically binds an antibody. In yet another embodiment, a fusion protein for use in the diagnostic and treatment methods disclosed herein comprises a polypeptide having the amino acid sequence of any one, two, three or more of the $V_H$ CDRs of an antibody and the amino acid sequence of any one, two, three or more of the $V_L$ CDRs of an antibody, or fragments or variants thereof, and a heterologous polypeptide sequence. Preferably, two, three, four, five, six, or more of the $V_H$-CDR(s) or $V_L$—CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor [(Gascoigne et al., Proc. Natl. Acad. Sci. USA 84 (1987), 2936-2940; CD4 (Capon et al., Nature 337 (1989), 525-531; Traunecker et al., Nature 339 (1989), 68-70; Zettmeissl et al., DNA Cell Biol. USA 9 (1990), 347-353; and Byrn et al., Nature 344 (1990), 667-670); L-selectin (homing receptor) (Watson et al., J. Cell. Biol. 110 (1990), 2221-2229; and Watson et al., Nature 349 (1991), 164-167); CD44 (Aruffo et al., Cell 61 (1990), 1303-1313); CD28 and B7 (Linsley et al., J. Exp. Med. 173 (1991), 721-730); CTLA-4 (Lisley et al., J. Exp. Med. 174 (1991), 561-569); CD22 (Stamenkovic et al., Cell 66 (1991), 1133-1144); TNF receptor (Ashkenazi et al., Proc. Natl. Acad. Sci. USA 88 (1991), 10535-10539; Lesslauer et al., Eur. J. Immunol. 27 (1991), 2883-2886; and Peppel et al., J. Exp. Med. 174 (1991), 1483-1489 (1991); and IgE receptor a (Ridgway and Gorman, J. Cell. Biol. 115 (1991), Abstract No. 1448)].

As discussed elsewhere herein, antibodies, or antigen-binding fragments, variants, or derivatives thereof of the invention may be fused to heterologous polypeptides to increase the in vivo half-life of the polypeptides or for use in immunoassays using methods known in the art. For example, in one embodiment, PEG can be conjugated to the antibodies of the invention to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512.

Moreover, antibodies, or antigen-binding fragments, variants, or derivatives thereof of the invention can be fused to marker sequences, such as a peptide to facilitate their purification or detection. In preferred embodiments, the marker amino acid sequence is a hexa-histidine peptide (HIS), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86 (1989), 821-824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37 (1984), 767) and the "flag" tag.

Fusion proteins can be prepared using methods that are well known in the art; see for example U.S. Pat. Nos. 5,116,964 and 5,225,538. The precise site at which the fusion is made may be selected empirically to optimize the secretion or binding characteristics of the fusion protein. DNA encoding the fusion protein is then transfected into a host cell for expression.

Antibodies of the present invention may be used in non-conjugated form or may be conjugated to at least one of a variety of molecules, e.g., to improve the therapeutic properties of the molecule, to facilitate target detection, or for imaging or therapy of the patient. Antibodies, or antigen-binding fragments, variants, or derivatives thereof of the invention can be labeled or conjugated either before or after purification, when purification is performed. In particular, antibodies, or antigen-binding fragments, variants, or derivatives thereof of the invention may be conjugated to biotin, fluorophores, toxins, therapeutic agents, prodrugs, peptides, proteins, enzymes, viruses, lipids, biological response modifiers, pharmaceutical agents, or PEG as described in the following paragraph.

Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

Those skilled in the art will appreciate that conjugates may also be assembled using a variety of techniques depending on the selected agent to be conjugated. For example, conjugates with biotin are prepared e.g., by reacting an αSyn binding polypeptide with an activated ester of biotin such as the biotin N-hydroxysuccinimide ester. Similarly, conjugates with a fluorescent marker may be prepared in the presence of a coupling agent, e.g., those listed herein, or by reaction with an isothiocyanate, preferably fluorescein-isothiocyanate. Conjugates of the antibodies, or antigen-binding fragments, variants, or derivatives thereof of the invention are prepared in an analogous manner.

The present invention further encompasses antibodies, or antigen-binding fragments, variants, or derivatives thereof of the invention conjugated to a diagnostic or therapeutic agent. The antibodies can be used diagnostically to, for example, demonstrate presence of a neurological disease, to indicate the risk of developing a neurological disease, to monitor the development or progression of a neurological disease, i.e., synucleinopathic disease as part of a clinical testing procedure to, e.g., determine the efficacy of a given treatment and/or prevention regimen. Detection can be facilitated by coupling the antibody, or antigen-binding fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions; see, e.g., U.S. Pat. No. 4,741,900 for metal ions which can be conjugated to antibodies for use as diagnostics according to the present invention. Examples of suitable enzymes include horseradish peroxidase, alkaline phosphatase, 0-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include. $^{125}I$, $^{131}I$, $^{111}In$ or $^{99}Tc$.

An antibody, or antigen-binding fragment, variant, or derivative thereof also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an antibody, or antigen-binding fragment, variant, or derivative thereof can be detectably labeled is by linking the same to an enzyme and using the linked product in an enzyme immuno assay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, Meth. Enzymol. 73 (1981), 482-523; Maggio, E. (ed.), Enzyme Immunoassay, CRC Press, Boca Raton, Fla., (1980); Ishikawa, E. et al., (eds.), Enzyme Immunoassay, Kgaku Shoin, Tokyo (1981). The enzyme, which is bound to the antibody will react with an appropriate substrate, preferably a chromogenic substrate, in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibody, or antigen-binding fragment, variant, or derivative thereof, it is possible to detect the antibody through the use of a radioimmunoassay (RIA) (see, for example, Weintraub, B., Principles of Radioimmunoassays, Seventh Training Course on Radioligand Assay Techniques, The Endocrine Society, (March, 1986)), which is incorporated by reference herein). The radioactive isotope can be detected by means including, but not limited to, a gamma counter, a scintillation counter, or autoradiography.

An antibody, or antigen-binding fragment, variant, or derivative thereof can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an antibody, or antigen-binding fragment, variant, or derivative thereof are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al. (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", Immunol. Rev. 62 (1982), 119-158.

As mentioned, in certain embodiments, a moiety that enhances the stability or efficacy of a binding molecule, e.g., a binding polypeptide, e.g., an antibody or immunospecific fragment thereof can be conjugated. For example, in one embodiment, PEG can be conjugated to the binding molecules of the invention to increase their half-life in vivo. Leong et al., Cytokine 16 (2001), 106; Adv. in Drug Deliv. Rev. 54 (2002), 531; or Weir et al., Biochem. Soc. Transactions 30 (2002), 512.

Compositions and Methods of Use

The present invention relates to compositions comprising the aforementioned antigens, scaffolds, and cells and methods to produce antibodies more efficiently than current methods. In an embodiment, the scaffolds and antigens are co-administered to the cells. In a preferred embodiment, the polymer scaffolds and antigens are mixed prior to administering to the cells so that the antigens may be incorporated into the scaffolds.

In some embodiments, the polymer micellar scaffolds such as PBC and antigens may be mixed in a ratio from about 1:5 to about 10:1, from about 1:2 to about 6:1, and preferably from about 1:1 to about 4:1. In some embodiments, the final concentration of the scaffolds used to treat the cells is from about 0.3 to about 100 μg/mL, from about 1 to about 50 μg/mL, or from about 5 to about 20 μg/mL. In some embodiments, the final concentration of the antigen, or fragment thereof, is from about 0.1 to about 100 μg/mL, from about 1 to about 50 μg/mL, or from about 5 to about 10 μg/mL. In some embodiments, nucleic acids such as mRNA can be used with the PBCs.

In some embodiments, the antigen or antigenic determinant is viral, preferably a human virus. In a preferred embodiment, the antigen or antigenic determinant is from a virus listed on the Human viruses and associated pathologies list (available at viralzone.expasy.org/678, herein incorporated by reference in its entirety). In other embodiments, the antigen or antigenic determinant is bacterial. In a more preferred embodiment, the antigen or antigenic determinant is from a bacteria species listed on the Pathogenic Bacteria Database (available at globalrph.com/bacteria, herein incorporated by reference in its entirety). In yet other embodiments the antigen or antigenic determinant is fungal. In more preferred embodiments, the antigen or antigenic determinant is from a fungus listed on the Fungal Disease list (available from cdc.gov/fungal/diseases/index.html, herein incorporated by reference in its entirety). In still other embodiments, the antigen or antigenic determinant is from a parasite. In more preferred embodiments, the antigen or antigenic determinant is listed on the Parasites database (available from cdc.gov/parasites/az/index.html, herein incorporated by reference in its entirety).

In another embodiment, the cells are stimulated for about 4 days, for about 8 days, for about 10 days, or for about 12 days before collection of antibodies. The level of the resulting antibody may be assessed by any suitable method known in the art comprising, e.g., analyzing antibody level by one or more techniques chosen from enzyme immuno assay (EIA), Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry. Preferably, said in vivo imaging of antibodies comprises positron emission tomography (PET), single photon emission tomography (SPECT), near infrared (NIR) optical imaging or magnetic resonance imaging (MRI).

The present invention also relates to compositions comprising the aforementioned antibody or antigen-binding fragment thereof of the present invention or derivative or variant thereof, or the polynucleotide, vector, or cell of the invention for the use in an early diagnostic or therapeutic. A composition of the present invention may further comprise a pharmaceutically acceptable carrier. Furthermore, the pharmaceutical composition of the present invention may comprise further agents such as interleukins or interferons depending on the intended use of the pharmaceutical composition. For example, for use in the treatment of infectious disease the additional agent may be selected from the group consisting of small organic molecules, adjuvants, antibodies, and combinations thereof. Hence, in a particular preferred embodiment the present invention relates to the use of the antibody or antigen-binding fragment thereof of the present invention, the polynucleotide, the vector or the cell of the present invention for the preparation of a pharmaceutical or diagnostic composition for prophylactic and therapeutic treatment of, by way of nonlimiting example, an infectious disease or cancer, monitoring the progression of a disease or a response to a disease treatment in a subject or for determining a subject's risk for developing a disease.

The present invention also provides a pharmaceutical and diagnostic, respectively, pack or kit comprising one or more containers filled with one or more of the above-described ingredients, e.g., antibody, binding fragment, derivative, or variant thereof, polynucleotide, vector, or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition, or alternatively, the kit comprises reagents and/or instructions for use in appropriate diagnostic assays. The composition, e.g., kit of the present invention is of course particularly suitable for the risk assessment, diagnosis, prevention, and treatment of a disease.

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be affected by different ways, e.g., by intravenous, intraperitoneal, subcutaneous, intramuscular, intranasal, topical, or intradermal administration or spinal or brain delivery. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

In further embodiment, the composition further includes loading the one or more of the above-described ingredients, e.g., antibody, binding fragment, derivative, or variant thereof, polynucleotide, vector, or cell of the present invention, into a nanoparticle carrier. The nanoparticle may be any known in the art, for example polyanhydride nanoparticles. The nanoparticles may help to increase the half-life of the compositions from preventing them leaking out of the vasculature or being taken up into off site targets. The nanoparticles may also aid in the transition through the blood brain barrier and help target the ingredients to their intended sites. Using nanoparticles may allow a lower dosage of the ingredients due to these benefits provided by an increased half-life and better targeting. The nanoparticles may further be functionalized by conjugating with various materials, such as PEG.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 μg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example, dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions, or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition of the invention may comprise further agents such as dopamine or psychopharmacologic drugs, depending on the intended use of the pharmaceutical composition.

Furthermore, in a preferred embodiment of the present invention the pharmaceutical composition may be formulated as a vaccine, for example, if the pharmaceutical composition of the invention comprises an antibody or binding fragment, derivative, or variant thereof for passive immunization.

In one embodiment, it may be beneficial to use recombinant Fab (rFab) and single chain fragments (scFvs) of the antibody of the present invention, which might more readily penetrate a cell membrane. For example, Robert et al., Protein Eng. Des. Sel. (2008) October 16; S1741-0134, published online ahead, describe the use of chimeric recombinant Fab (rFab) and single chain fragments (scFvs) of monoclonal antibody WO-2 which recognizes an epitope in the N-terminal region of Ap. The engineered fragments were able to (i) prevent amyloid fibrillization, (ii) disaggregate preformed Aβ1-42 fibrils and (iii) inhibit Aβ1-42 oligomer-mediated neurotoxicity in vitro as efficiently as the whole IgG molecule. The perceived advantages of using small Fab and scFv engineered antibody formats which lack the effector function include more efficient passage across the blood-brain barrier and minimizing the risk of triggering inflammatory side reactions. Furthermore, besides scFv and single-domain antibodies retain the binding specificity of full-length antibodies, they can be expressed as single genes and intracellularly in mammalian cells as intrabodies, with the potential for alteration of the folding, interactions, modifications, or subcellular localization of their targets; see for review, e.g., Miller and Messer, Molecular Therapy 12 (2005), 394-401.

In a different approach Muller et al., Expert Opin. Biol. Ther. (2005), 237-241, describe a technology platform, so-called "SuperAntibody Technology", which is said to enable antibodies to be shuttled into living cells without harming them. Such cell-penetrating antibodies open new diagnostic and therapeutic windows. The term "TransMabs" has been coined for these antibodies.

A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Preferably, the therapeutic agent in the composition is present in an amount sufficient to restore or preserve normal behavior and/or cognitive properties in case of PD, DLB or other synucleinopathic diseases.

From the foregoing, it is evident that the present invention encompasses any use of a binding molecule comprising at least one CDR created by the in vitro methods and compositions used in the method, in particular for diagnosing and/or treatment of a disease as mentioned above, particularly infectious disease. Preferably, said binding molecule is an antibody of the present invention or an immunoglobulin chain thereof. In addition, the present invention relates to anti-idiotypic antibodies of any one of the mentioned antibodies described hereinbefore. These are antibodies or other binding molecules which bind to the unique antigenic peptide sequence located on an antibody's variable region near the antigen-binding site and are useful, e.g., for the detection of other antibodies in sample of a subject.

In another embodiment the present invention relates to a diagnostic composition comprising any one of the above described binding molecules, antibodies, antigen-binding fragments, polynucleotides, vectors or cells of the invention and optionally suitable means for detection such as reagents conventionally used in immuno or nucleic acid based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), such as enzyme immuno assay (EIA), flow cytometry, or the Western blot assay. The antigens and antibodies of the invention can be bound to many different carriers and used to isolate cells specifically bound thereto. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. Nanoparticles may also be used as a carrier. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the binding molecules, in particular antibodies of the present invention may also be used in a method for the diagnosis of a disease in an individual by obtaining a body fluid sample from the tested individual which may be a blood sample, a lymph sample or any other body fluid sample and contacting the body fluid sample with an antibody of the instant invention under conditions enabling the formation of antibody-antigen complexes. The level of such complexes is then determined by methods known in the art; a level significantly higher than that formed in a control sample indicating the disease in the tested individual. In the same manner, the specific antigen bound by the antibodies of the invention may also be used. Thus, the present invention relates to an in vitro immunoassay comprising the binding molecule, e.g., antibody or antigen-binding fragment thereof of the invention as illustrated in the Examples.

In this context, the present invention also relates to means specifically designed for this purpose. For example, an antibody-based array may be used, which is for example loaded with antibodies or equivalent antigen-binding molecules of the present invention which specifically recognize an antibody. Design of microarray immunoassays is summarized in Kusnezow et al., Mol. Cell Protcomics 5 (2006), 1681-1696. Accordingly, the present invention also relates to microarrays loaded with desired binding molecules identified in accordance with the present invention.

In one embodiment, the present invention relates to a method of diagnosing a disease in a subject, the method comprising: (a) assessing a level of antigen in a sample from the subject to be diagnosed with a binding molecule of the present invention; and (b) comparing the level of the antigen to a reference standard that indicates the level of the antigen in one or more control subjects, wherein a difference or similarity between the level of the antigen and the reference standard indicates that the subject has a disease.

The subject to be diagnosed may be asymptomatic or preclinical for the disease. Preferably, the control subject has a disease, wherein a similarity between the level of antigen and the reference standard indicates that the subject to be diagnosed has a disease. Alternatively, or in addition as a second control the control subject does not have a disease, wherein a difference between the level of antigen and the reference standard indicates that the subject to be diagnosed has a disease. In some embodiments, it may be preferable to age-match the subject to be diagnosed and the control subject(s). The sample to be analyzed may be any body fluid suspected to contain the antigen, for example a blood, or a fraction of blood, CSF, or urine sample.

The level of antigen may be assessed by any suitable method known in the art comprising, e.g., analyzing the antigen by one or more techniques chosen from enzyme immuno assay (EIA), Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), or laser densitometry. Preferably, said in vivo imaging of antigen comprises positron emission tomography (PET), single photon emission tomography (SPECT), near infrared (NIR) optical imaging or magnetic resonance imaging (MRI).

Methods of diagnosing a disease, monitoring a disease progression, and monitoring a disease treatment using antibodies and related means which may be adapted in accordance with the present invention are also described in international application WO2007/011907.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example, the public database "Medline" may be utilized, which is hosted by the National Center for Biotechnology Information (NCBI) and/or the National Library of Medicine (NLM) at the National Institutes of Health (NIH). Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

One skilled in the art will also appreciate that the antigens may be replaced with any receptor binding molecule to allow the scaffold to crosslink various receptors on a cells surface.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. Full bibliographic citations may be found at the end of the specification immediately preceding the claims. The contents of all cited references (including literature references, issued patents, published patent applications as cited throughout this application and manufacturer's specifications, instructions, etc.) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

Example 1

The diversity in population demographics (as a function of age, genetics, and other factors) leads to significant variability in the induction of host immune responses to vaccines, requiring the development of novel adjuvants. A case in point is the COVID-19 pandemic, which has for example, disproportionately impacted older adults (A. L. Mueller, M. S. McNamara, D. A. Sinclair, Why does COVID-19 disproportionately affect older people? *Aging (Albany. NY)*, 12, 9959-9981 (2020)). Efficient preventive measures for such threats require the design of vaccine adjuvants that can balance competing requirements. In this context, for rational design of COVID-19 vaccines for older adults, it is important to generate vaccine formulations that account for immunosenescence and that can balance the competition between the exacerbated inflammation in aging with the induction of effective immune responses. Traditional adjuvants (e.g., Toll-like receptor (TLR) agonists) typically induce strong immune responses, but also create a pro-inflammatory environment, which are known to diminish aged immune responses (M. T. Ventura, M. Casciaro, S.

Gangemi, R. Buquicchio, Immunosenescence in aging: between immune cells depletion and cytokines up-regulation. *Clin. Mol. Allergy.* 15, 21 (2017)). Since a robust B cell response is critical for providing antibody-based protection against many infectious diseases (including COVID-19)[1-4], mechanistic studies exploring the interaction of adjuvants with B cells have important implications for the development of new vaccines.

Self-assembling micellar systems of different sizes and chemistries have been extensively used for vaccine delivery[5]. Their small size (<100 nm), flexibility for functionalization, and ability to deliver antigens to antigen presenting cells (APCs) make them promising platforms for vaccine adjuvants. There are multiple reports focusing on the use of micelle-based adjuvants[15-19]. The immune-enhancing characteristics of these micellar adjuvants are similar to that of the aforementioned traditional adjuvants and in that they activate APCs, induce pro-inflammatory cytokine secretion and lead to antibody responses with similar kinetics as that of the traditional adjuvants[20-23]. However, little is known about their mechanism of action in the context of B cell activation.

We have recently reported on the synthesis of a new class of amphiphilic pentablock copolymers (PBC) based on the FDA-approved temperature-responsive[6] the block copolymer poloxamer 407, sold commercially as Pluronic® F127, and cationic end-group blocks of poly(diethylaminoethylmethacrylate) (PDEAEM), which undergo both temperature and pH-responsive self-assembly to form micelles[7]. The PBC micelles have been shown to associate with antigens (Ag) to form PBC micelle-Ag complexes and enhance Ag delivery to APCs[8]. They have also been demonstrated to induce rapid and short-term enhancement in antibody responses in both young and aged mice[24]. However, the underlying mechanism of action of these PBC micelles in the context of B cell activation is unknown. In addition, observations indicate that the PBC micelles neither activate APCs nor do they lead to the induction of innate effector molecules, nitric oxide, reactive oxygen species and pro-inflammatory cytokines (Senapati, R. J. Darling, D. Loh, I. C. Schneider, M. J. Wannemuehler, B. Narasimhan, S. K. Mallapragada, Pentablock copolymer micelle nanoadjuvants enhance cytosolic delivery of antigen and improve vaccine efficacy while inducing low inflammation. *ACS Biomater. Sci. Eng.* 5, 1332-1342 (2019)). This enhanced humoral immune response induced by the PBC micelles while inducing less inflammation is especially beneficial for development of vaccine formulations for older adults[9,10]. This is because traditional adjuvants such as TLR agonists, alum, and MF59 induce deleterious inflammation concomitantly with enhanced antibody responses, leading to diminished immune responses in aged immune systems[11-14].

We hypothesize that the dissimilarity in characteristics of the immune response generated between the PBC micelles and traditional adjuvants may be attributed to the material properties of the PBC micelles and the mechanisms involved in their interactions with B cells. To this end, in this work, we delineate the mechanism underlying the B cell responses induced by PBC micelles and identify key attributes contributing to this behavior. We demonstrate that crosslinking of B cell receptors (BCRs) by PBC micelles leads to B cell activation by utilizing Nur77 antibody which is expressed on B cells only upon antigen-receptor engagement[25]. After confirming the engagement of BCRs with the PBC micelle-Ag complexes, we show that the crosslinking induces B cell proliferation in vitro by PBC micelle-Ag complexes, leading to the production of antigen-specific antibodies. Finally, we demonstrate that BCR crosslinking by PBC micelles can be exploited for in vitro production of therapeutic antibodies to a diverse array of antigens associated with *Yersinia pestis* (F1-V) and SARS-CoV-2 (Spike protein).

I. Methods

Materials

N,N-(diethylamino)ethyl methacrylate (DEAEM), Pluronic® F127, hen egg white lysozyme (HEL), IgG from rat serum, and Triton X-100 were purchased from Sigma-Aldrich (St. Louis, MO). Goat anti-mouse IgM $F(ab')_2$ fragment, goat anti-mouse IgM Fab fragment and alkaline-phosphatase-conjugated anti-mouse IgM were purchased from Jackson ImmunoResearch Laboratories, Inc. (West Grove, PA). Endotoxin-free ovalbumin (OVA) was purchased from InVivogen (San Diego, CA). *Y. pestis* fusion protein F1-V (NR-4526) was obtained from the Biodefense and Emerging Infections Repository (Manassas). SARS-CoV-2 spike protein was purchased from GenScript (Piscataway, NJ). Antibodies for flow cytometry (PE anti-mouse CD19, APC/Cy7 anti-mouse B220, Zombie Aqua viability kit, PE-Cy7 anti-mouse Nur77, and PerCp-Cy5.5 anti-mouse CD3, anti-CD16/32) and purified anti-mouse CD40 antibody were purchased from BioLegend (San Diego, CA). BD stabilizing fixative was purchased from BD Bioscience (Franklin Lakes, NJ). All other chemicals and materials were purchased from Fisher Scientific (Pittsburgh, PA).

PBC Scaffold Synthesis

The pentablock copolymer (PBC) was synthesized by atom transfer radical polymerization (ATRP) as previously reported[26]. This involves the formation of a difunctional macroinitiator from Pluronic® F127 (a commercial version of poloxamer 407) as the first step. Alternatively, other Pluronics, such as Pluronic P123 can also be used in this step as other examples. Next, the macroinitiator and the monomer, DEAEM are reacted utilizing copper (I) oxide nanoparticles as the catalyst and N-propylpyrilidinemethanamine (NPPM) as the complexing ligand. The molecular weight of the resulting PBC was determined using $^1H$ NMR.

For the micelle formulation, a stock solution of 50 mg/mL total polymer concentration (either PBC or Pluronic® F127) was prepared in phosphate-buffered saline. The stock solution was diluted to the required concentrations and mixed with the antigens prior to stimulation of cells. For characterizing the size, zeta potential and CMC of PBC and Pluronic® F127 micelles, dynamic light scattering measurements with a Zetasizer Nano S (Malvern PANalytical, Westborough, MA) were carried out.

Animals

Female BALB/c or C57BL/6 mice (6-8-weeks old or 20-22 months old) and C57BL/6-Tg(IghelMD4)4Ccg//J mice (6 weeks old) were purchased from Jackson Laboratory (Bar Harbor, ME). The Institutional Animal Care and Use Committee (IACUC) at Iowa State University approved all the protocols involving animals.

Immunization and Serum Collection

To evaluate antibody responses, C57BL/6 mice were subcutaneously immunized with 100 μL of the PBC micelle (5 mg per dose) formulation or MPLA (10 μg per dose) formulation, or MPLA and PBC micelle formulation with 50 μg of either HEL or OVA antigen. Control animals were immunized with soluble HEL or OVA in PBS (50 μg in 100 μL) (i.e., no adjuvant). Serum samples were collected via the saphenous vein at 2-, 4-, 6-, 8- and 10-weeks post-immunization.

Tissue Isolation and Cell Culture

A cell suspension of splenocytes from mice (BALB/c and C57BL/6) collected after euthanasia was prepared using a hand-held tissue homogenizer. The tissue culture medium used consisted of RPMI 1640, 1% (1 μg/mL) pen/strep and 10% fetal bovine serum. Lysis was performed to remove erythrocytes from the cell suspension and the resulting splenocytes were washed with media before counting the cells.

One set of splenocytes was labeled with carboxyfluorescein succinimidyl ester (CFSE) for analyzing cell proliferation post-stimulation. The cells were stained with CFSE on day 0 after isolation from spleens using standard procedure and stimulated with different treatment groups for 4-5 days. After stimulation, cells were stained with antibodies for flow cytometry.

The other set of splenocytes was directly used for stimulation and collection of supernatants 10 days post-stimulation. For the plating, the splenocytes (with or without CFSE stains) were plated in 96-well U-bottom tissue culture plates at the density of $5\times10^5$ cells/well with 200 μL of media in each well. The cells were stimulated with different combinations of treatment groups and concentrations found in Table 1.

Figure 2A:
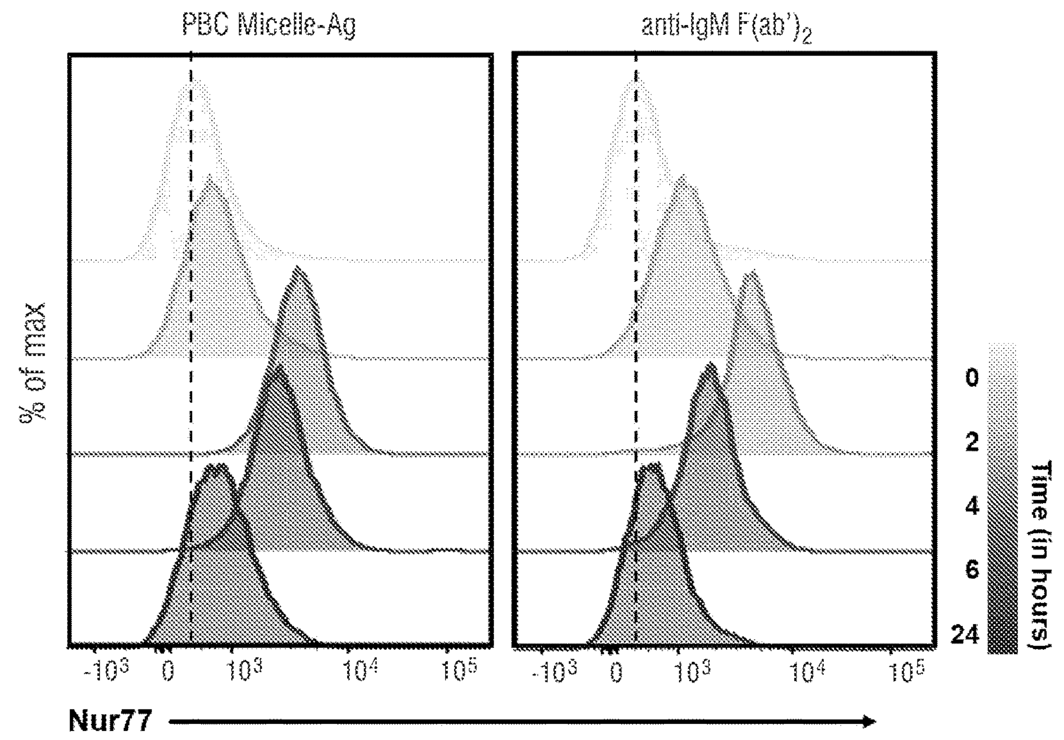
FIG. 2A shows representative histograms for Nur77 expression in B cells. Total splenic cell population from C57BL/6 mice were stimulated with either PBC micelle-Ag or Pluronic® F127 micelle-Ag (at 10 μg/mL each component). LPS at 0.5 μg/mL and anti-IgM Fa(ab')2 at 10 μg/mL were also used. Cells were stained for cell surface marker (CD19) for B cell gating and intracellularly stained for Nur77 expression using a Nur77-specific mAb at 2-, 4-, 6-, or 24-hours post-stimulation. Cells analyzed at 0-hour post-stimulation shown to indicate the background Nur77 expression levels (also represented by dashed line).
Figure 2B:
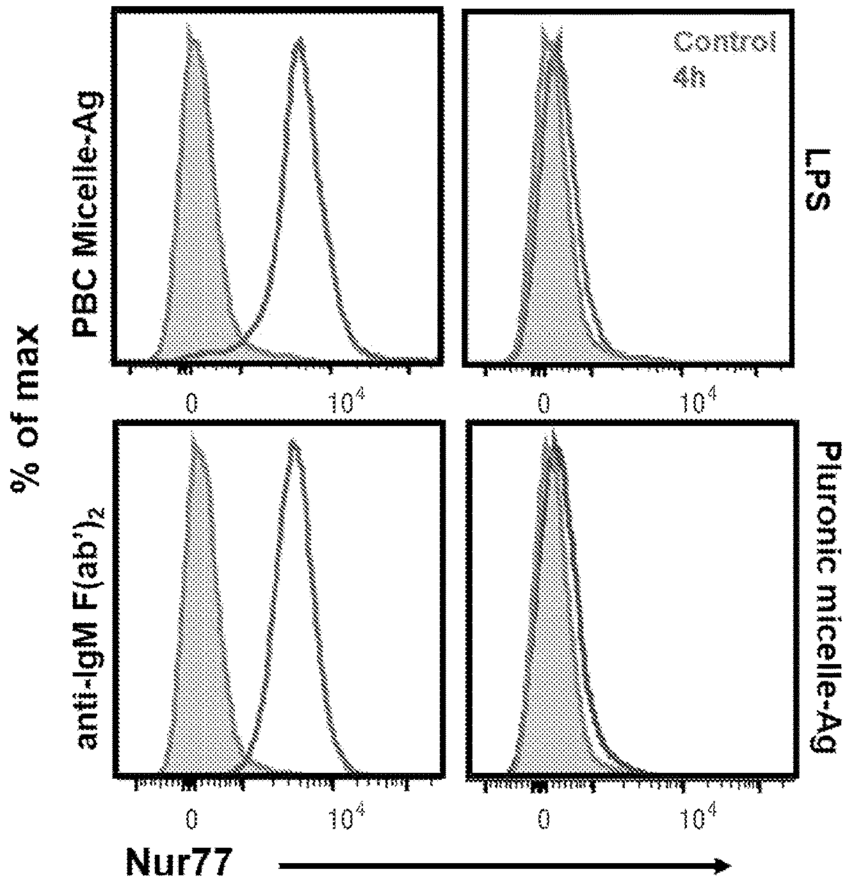
FIG. 2B shows representative histograms for Nur77 induction following 4-hour (the peak) of stimulation for four treatment groups (solid lines) and unstimulated control (light grey, filled). Data representative of three independent experiments.

Similar cell density and stimulant concentrations were utilized for the Nur77 expression studies in 96-well U-bottom tissue culture plates for various time periods of stimulation as indicated in FIGS. 2A-2B.

TABLE 1

Concentrations of various treatments for stimulation

| Treatment groups | Concentrations (μg/mL) |
|---|---|
| anti-IgM F $(ab')_2$ fragments | 10 μg/mL |
| anti-IgM F(ab) fragments | 10 μg/mL |
| Scaffolds | 5-20 μg/mL |
| Antigens (Ag) (HEL, OVA, F1-V) | 5-10 μg/mL |
| Scaffold-Ag complexes | 5-20 μg/mL and 5-10 μg/mL |
| anti-mouse CD40 | 2 μg/mL |

Flow Cytometry

B cell proliferation was detected using in vitro labeling of cells with CFSE and analysis by flow cytometry. Distinct generations of proliferating cells can be monitored by dilutions of CFSE stain on the cells as viewed on the flow cytometry plots. For the flow cytometry procedure, the cells were transferred into polystyrene FACS tubes and labelled with Zombie Aqua dye for tracking viable cells post-stimulation using manufacturer's instructions. Next, Fc receptors on the cells were blocked using 100 μg/mL of rat IgG and 10 μg/mL of anti-CD16/32 and stained with specific antibodies for surface markers (CD19, CD3 and B220) to detect the B cells in the splenocyte preparation. For intracellular staining of Nur77 antibody, following surface staining, cells were washed with PBS and then fixed with 4% p-formaldehyde. After washing the cells again with PBS, 0.1% Triton X-100 was used for permeabilization, and following that, Nur77 Ab at a 1:50 dilution was used to stain the cells. After the staining, cells were washed in FACS buffer to remove excess dye and samples were fixed prior to analysis. The flow cytometry data was collected on FACSCanto II (BD Bioscience, NJ) and analyzed using FlowJo (FlowJo LLC, Ashland, CA).

Cytokine Analysis

The cell-free supernatants were collected after 10 days of stimulation by centrifuging the culture plates to let the cells form a pellet at the bottom of the wells. These supernatants were used to measure the level of cytokine, TNFα. BioRad BioPlex 200 system (Hercules, CA) was used to run the assay and analyze supernatants for the presence of cytokines.

Antibody Responses

The antibody (Ab) levels in the sera collected from immunized animals at various time-points (2-,4-,6-,8- and 10-weeks post-immunization) and in the cell-free supernatants after 10 days of in vitro stimulation with various treatment groups were measured using enzyme-linked immunosorbent assay (ELISA). Briefly, high-binding 96-well plates were coated with antigens (HEL or OVA or F1-V or Spike protein), blocked with 2% w/v of gelatin in 0.05% Tween-PBS solution. Sera samples were added to the plates starting at 1:200 dilution and then diluted 1:2 across the plate. Supernatant samples were added to the plates at a starting dilution of 1:3 and then diluted 1:3 across the plate. Alkaline-phosphatase-conjugated anti-mouse IgM or anti-mouse Ig(G+M) were used as the secondary Ab. The plates were read at 405 nm using a SpectraMax M3 plate reader (Molecular Devices, San Jose, CA) after adding the substrate and the titer was recorded as the last dilution that exhibited an optical density value that was two-fold or more higher than the background optical density.

Statistical Analysis

All the data was analyzed using GraphPad Prism 8 software for statistical significance. For FIG. 1, Kruskal Wallis and Mann Whitney tests were used to determine statistical significance. For FIGS. 3-6, one-way analysis of variance (ANOVA) was used followed by Tukey's post-hoc test for multiple comparisons.

II Results

Material Characterization

Figure 7A:
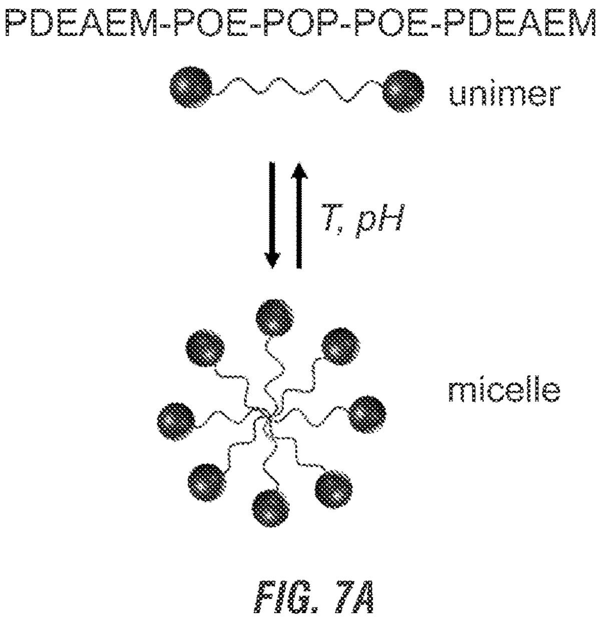
FIG. 7A shows a representative chemical structure of PBC micelle, PDEAEM: Poly-(diethylamino)ethyl methacrylate, POE: Polyoxyethylene, POP: Polyoxypropylene. Reversible temperature and pH dependent self-assembly leading to micellization.
Figure 7B:
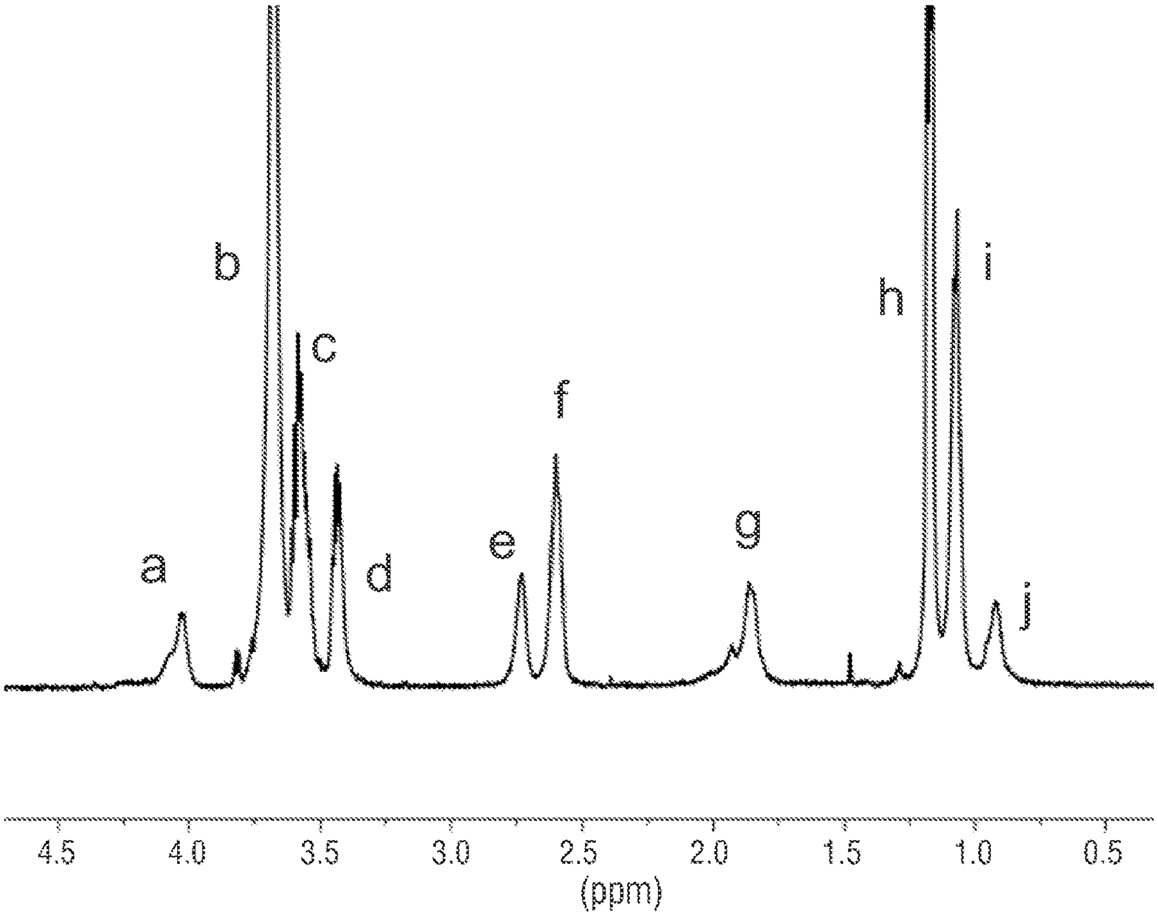
FIG. 7B shows $H^1$ NMR spectra of the PBC with corresponding peaks for bonds denoted with letters.
Figure 7C:
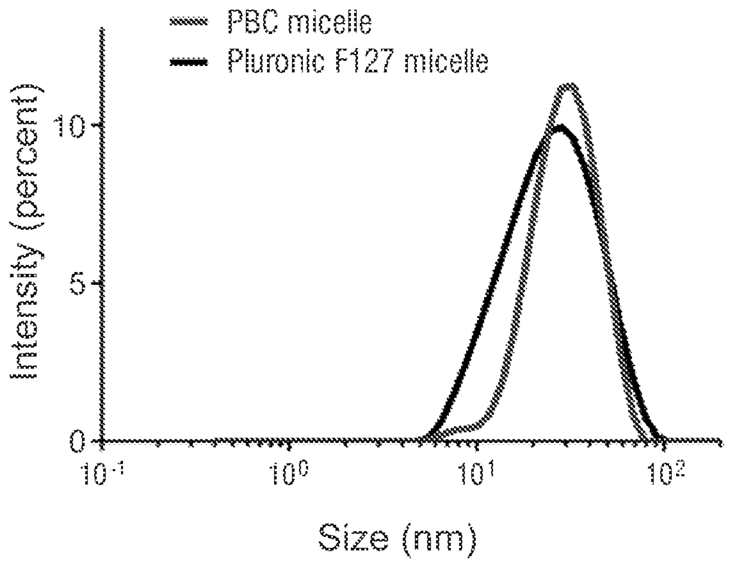
FIG. 7C shows the size of PBC micelle and Pluronic® F127 micelle determined using dynamic light scattering.

The purity and molecular mass of the synthesized PBC was determined using $^1$H NMR. The spectrum showed multiple characteristics peaks (FIGS. 7A and 7B) consistent with our previous work[26] and the average molecular weight was calculated to be 14,600 g/mol. The mean diameter of the PBC micelles (FIG. 7C) determined using dynamic light scattering was 30.4 nm (±2.7 nm), the zeta potential was +5.82 mV (±0.89 mV) with a CMC of about 0.3 μg/mL. In contrast, the mean diameter of Pluronic® F127 micelles was 27.1 (±3.2 nm) and the zeta potential was −0.30 mV (±0.17 mV) consistent with literature values[27,28].

Ab Responses Induced by PBC Micelles and Synergy with Traditional Adjuvants

Figure 1B:
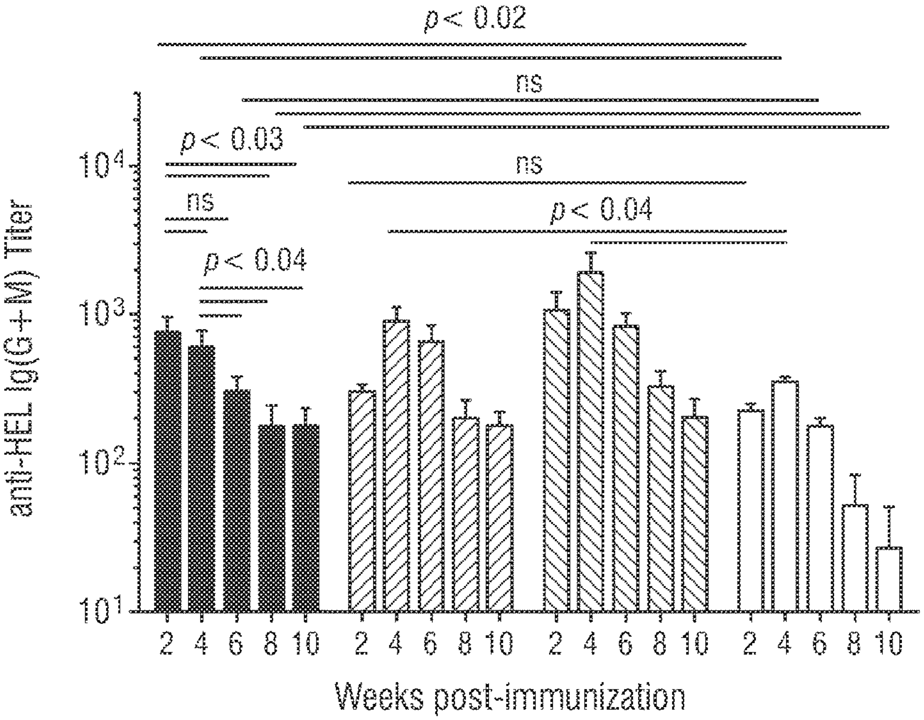
FIG. 1B shows a graphical representation of the antibody titers in sera collected from saphenous vein bleeds from mice 2-, 4-, 6-, 8- and 10-weeks post-immunization for anti-HEL Ig(G+M).
Figure 1C:
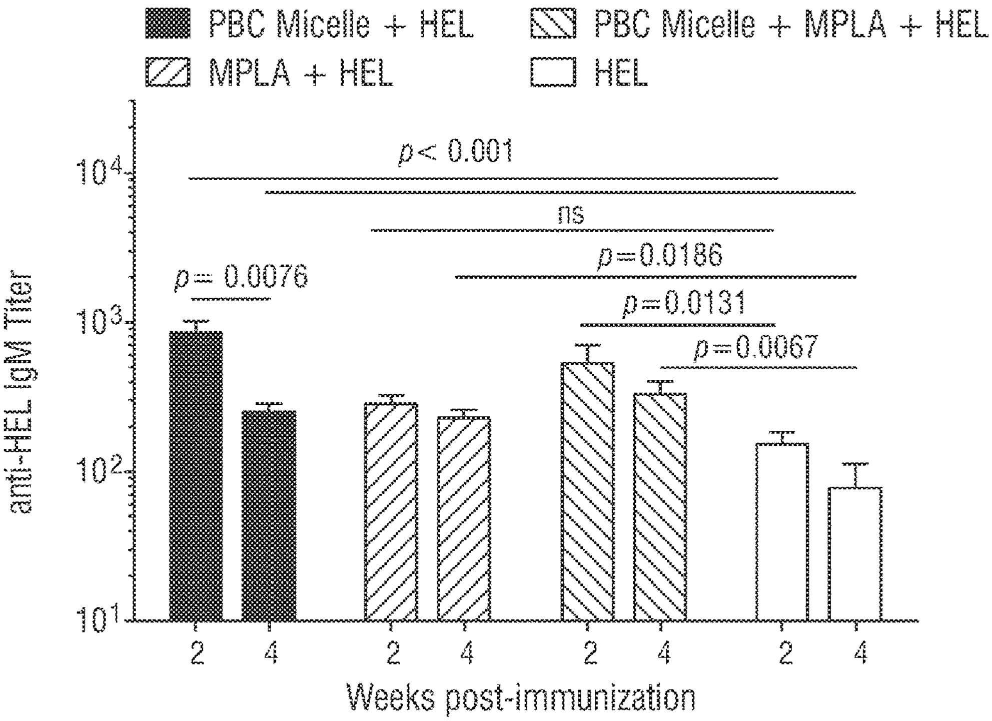
FIG. 1C shows a graphical representation of the antibody titers in sera collected from saphenous vein bleeds from mice 2-, 4-, 6-, 8- and 10-weeks post-immunization for anti-HEL IgM.
Figure 1D:
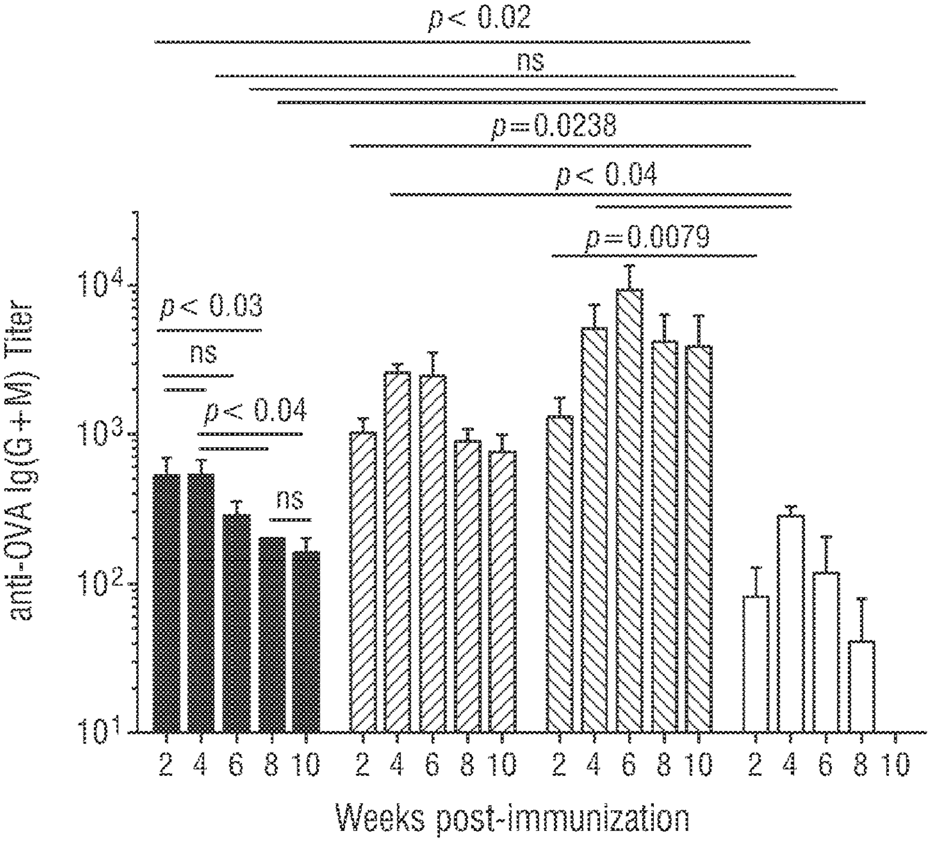
FIG. 1D shows a graphical representation of the antibody titers in sera collected from saphenous vein bleeds from mice 2-, 4-, 6-, 8- and 10-weeks post-immunization for anti-OVA Ig(G+M).
Figure 1E:
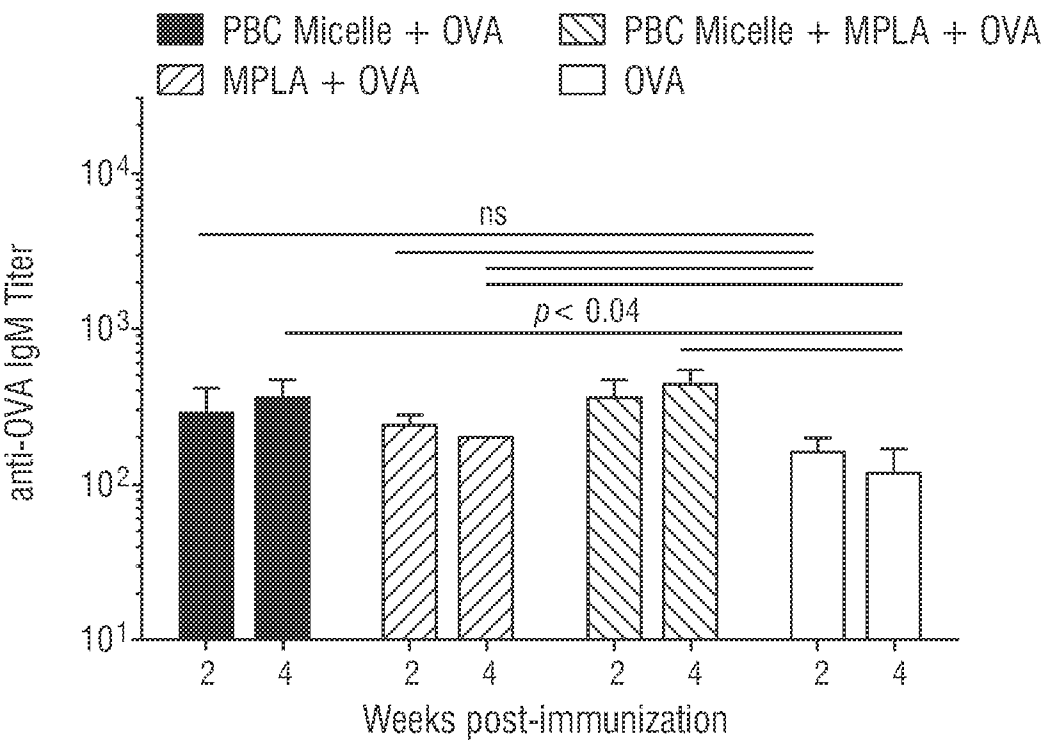
FIG. 1E shows a graphical representation of the antibody titers in sera collected from saphenous vein bleeds from mice 2-, 4-, 6-, 8- and 10-weeks post-immunization for anti-OVA IgM.

Our previous work showed that enhanced antibody responses in mice immunized with PBC micelles and a model Ag, ovalbumin (Ova) up to 4 weeks post-immunization were induced rapidly, but lasted for only a short duration of time[8]. Since we did not observe APC activation with PBC micelles, we hypothesized that the response consisted of predominantly IgM antibodies due to the lack of T cell help. In this work, we studied the nature and kinetics of in vivo antibody responses for 10 weeks post-immunization using two model antigens-Ova and hen-egg white lysozyme (HEL) (FIG. 1A). We compared the response of PBC micelles to that of a traditional adjuvant, MPLA. Mice immunized with PBC Micelle-HEL exhibited significantly higher anti-HEL serum Ab titers 2- and 4-weeks post-immunization (p.i.), compared to mice immunized with soluble HEL (FIG. 1). However, upon characterizing the Ab isotype, we observed that the Ab response consisted of predominantly anti-IgM antibodies (FIG. 1C). The anti-HEL Ig(G+M) titer induced by PBC micelle-HEL was not significant from that induced by soluble HEL at 8- and 10-weeks p.i. Hence, the kinetics of the Ab response to PBC micelle-HEL showed the onset of rapid and high titers at early time-points but waned without providing long-term (week 6 and week 8) enhancement in Ab responses, compared to soluble HEL. In contrast, mice immunized with a traditional adjuvant, monophosphoryl lipid A (MPLA)+HEL, did not exhibit rapid enhancement in Ab titers compared to mice immunized with soluble HEL at the 2-week time-point, but exhibited predominantly anti-HEL IgG antibody response peaking at week 4 p.i. with low levels of IgM responses (FIGS. 1B and 1C). Interestingly, immunization of animals using a combination of PBC micelles and MPLA with HEL led to a synergistic enhancement in the Ab responses compared to soluble HEL alone at all the time-points p.i. with the response being predominantly IgM at early time-points and class-switching to IgG at later time-points (after week 4). The Ab isotype and kinetics of the response was found to be similar for OVA as well, although immunization with OVA had more robust antibody responses overall, especially, for mice immunized with a combination of PBC micelles and MPLA (FIGS. 1D and 1E).

PBC Micelle-Ag Engagement with BCRs

We investigated the underlying mechanism of B cell activation that leads to the observed in vivo responses in mice immunized with PBC micelle-Ag formulations. Our previous studies showed that the PBC micelles associated with antigens (Senapati, R. J. Darling, D. Loh, I. C. Schneider, M. J. Wannemuehler, B. Narasimhan, S. K. Mallapragada, Pentablock copolymer micelle nanoadjuvants enhance cytosolic delivery of antigen and improve vaccine efficacy while inducing low inflammation. *ACS Biomater. Sci. Eng.* 5, 1332-1342 (2019)). Hence to gauge the engagement of PBC micelle-Ag complexes with BCRs, analysis of endogenous Nur77 protein expression in B cells stimulated with PBC micelle-Ag was performed and compared with that induced by two controls: lipopolysaccharide (LPS, a TLR4 agonist) and Pluronic® F127 block copolymer micelles. Nur77 is a well-studied specific marker for Ag-receptor signaling for both B and T cells in mice and humans and reflects the strength of receptor signaling[2529]. We found that Nur77 was induced in murine splenic B cells ($CD19^+$) upon stimulation with PBC micelle-Ag complexes at levels similar to anti-IgM $F(ab')_2$ (control) stimulation (FIG. 2A). We also studied Nur77 induction at different time-points of stimulation. Although after two hours post-stimulation Nur77 induction for the PBC micelle-Ag treatment was not as pronounced as the anti-IgM $F(ab')_2$ control, we observed robust induction at four hours post-stimulation for both treatments, which declined to basal levels by 24 hours post-stimulation. Similar kinetics have been previously reported for Nur77 induction[30]. In contrast, LPS did not trigger Nur77 induction, consistent with the literature[30] (FIG. 2B). Cells stimulated with Pluronic® F127 micelle-Ag were also evaluated and failed to effectively induce Nur77, indicating the non-engagement of BCRs with these micelles. These studies show that the PBC micelles specifically engaged B cells via interactions with the BCR.

B Cell Activation Via BCR Crosslinking by PBC Micelles

Figure 3A:
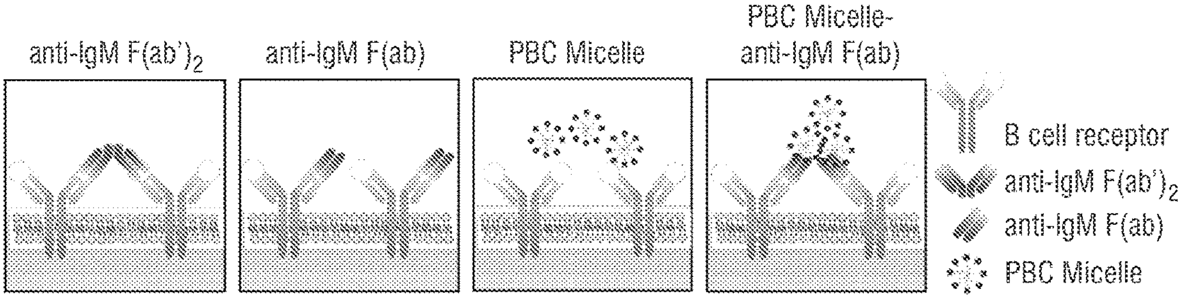
FIG. 3A shows an exemplary schematic of the experiment showing stimulation of wild-type (WT) murine spleen cells with anti-IgM F(ab')2 (10 μg/mL), or anti-IgM F(ab) (10 g/mL), or PBC micelle (10 μg/mL), or PBC micelle-anti-IgM F(ab) (10 μg/mL each). For results shown in FIGS. 3 B-E, anti-CD40 (5 μg/mL) was added to the culture medium for all the treatment groups except unstimulated controls.
Figure 8A:
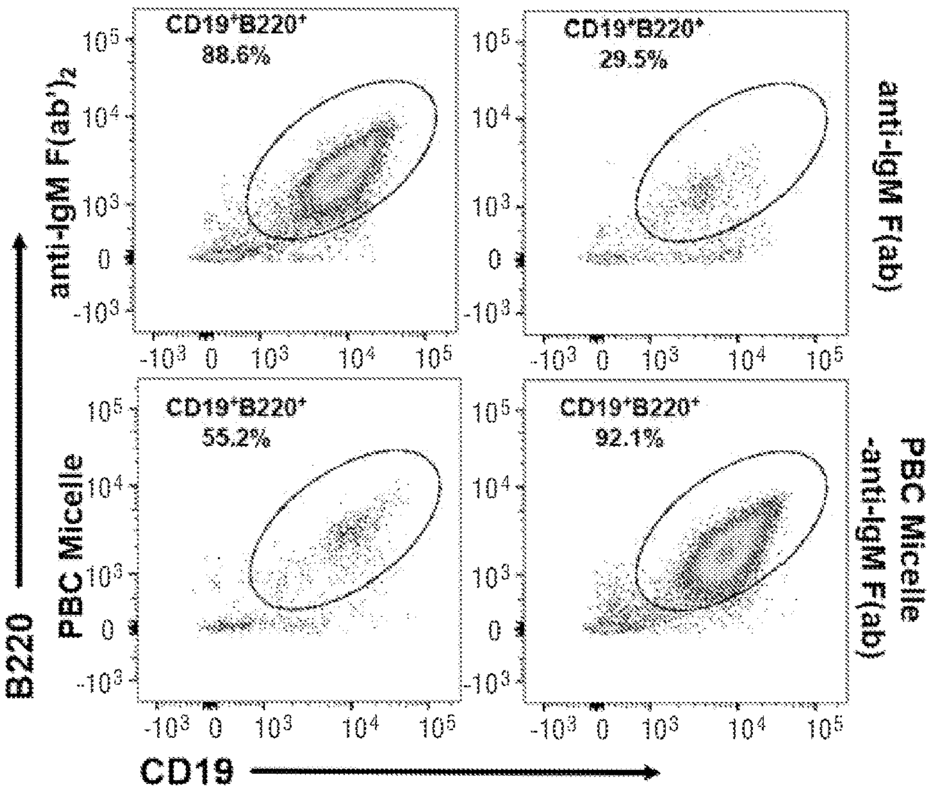
FIG. 8A shows representative B cell gating strategy and percentage of B cell populations for different stimulation groups as indicated. Anti-CD40 (5 μg/mL) was added to all the treatment groups shown.

Together, the observations of predominantly IgM antibody responses generated by PBC micelles, non-activation of APCs, and engagement of PBC micelle-Ag with BCRs all led us to investigate the mechanism of B cell activation by crosslinking of BCRs. To test our hypothesis, B cell proliferation from splenic cells isolated from C57BL/6 wild-type (WT) mice was investigated by using a carboxyfluorescein diacetate succinimidyl ester (CFSE) proliferation assay[31]. The schematic of this study is shown in FIG. 3A. To demonstrate BCR crosslinking, anti-IgM F(ab) fragments were used with or without PBC micelles to stimulate the splenic cells. Anti-IgM $F(ab')_2$ (10 μg/mL) was used as a positive control. Anti-CD40 (5 μg/mL) was added to all treatment groups except unstimulated medium only control, to provide a costimulatory signal. After five days in culture, the viability of B cells (Zombie $Aqua^-CD3^-CD19^+B220^+$) was observed to be lower for the cells stimulated with F(ab) fragments alone (10 μg/mL), PBC micelle alone (10 μg/mL) and unstimulated controls (medium only) compared to that of cells stimulated with either $F(ab')_2$ (positive control) or PBC micelle-F(ab), indicating that only these two treatments provided the required survival signal to B cells through the engagement of the BCR and the subsequence cellular signaling (FIG. 8A).

Figure 3B:
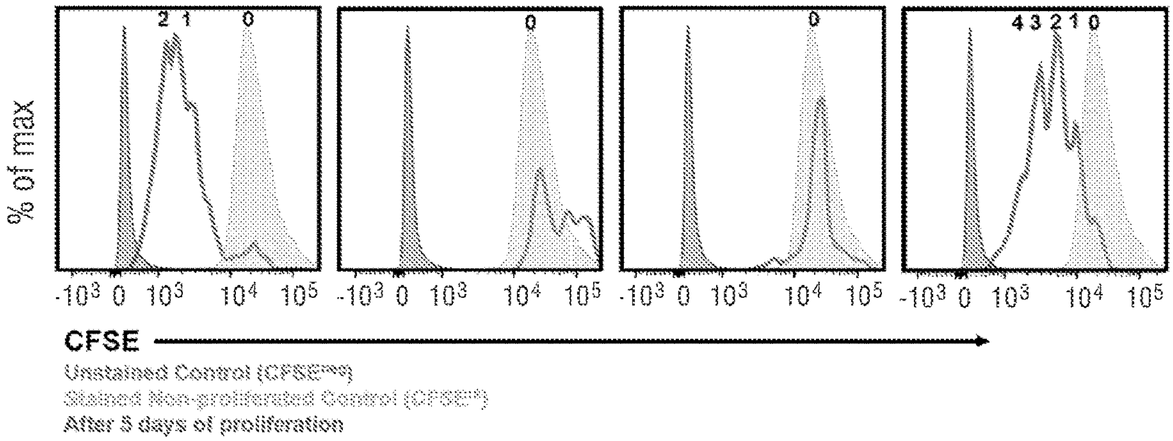
FIG. 3B shows the corresponding representative histograms for the stimulation groups with carboxyfluorescein diacetate succinimidyl ester (CFSE) expression for viable B cells (Zombie−CD3−CD19+B220+) from flow cytometry. The histograms (lines) were generated 5 days after treatment was initiated. Peaks for CFSE-unstained cells (dark grey, filled, far left) and CFSE-stained non-proliferated cells (light grey, filled, far right) are also shown.
Figure 3C:
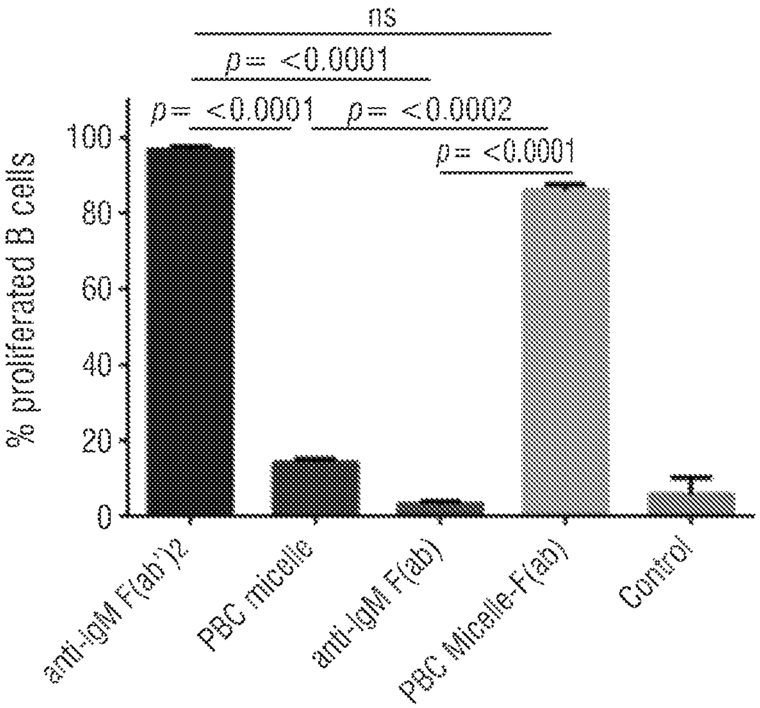
FIG. 3C shows the percent proliferated viable B cells from spleens as determined by CFSElo gating for young mice.
Figure 3D:
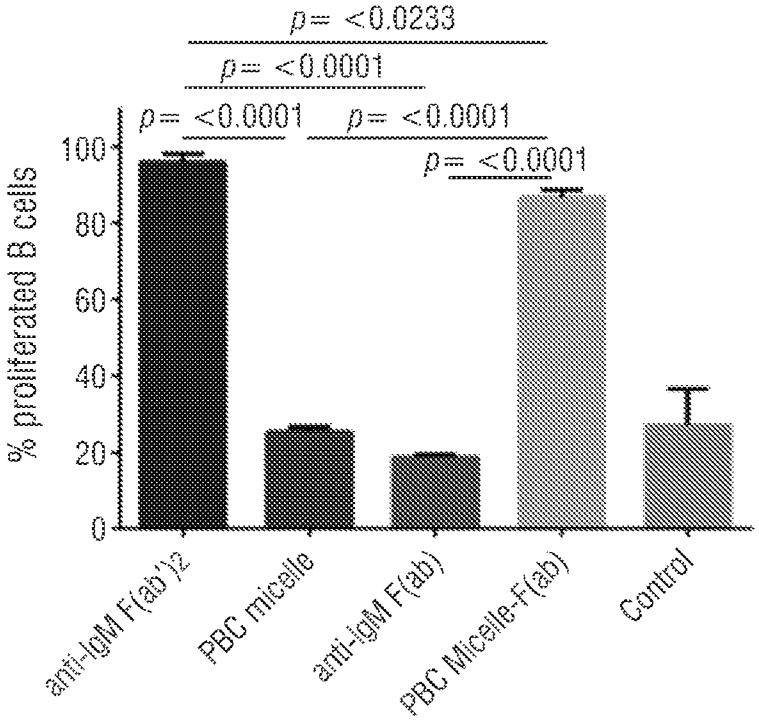
FIG. 3D shows the percent proliferated viable B cells from spleens as determined by CFSElo gating for aged mice.
Figure 8B:
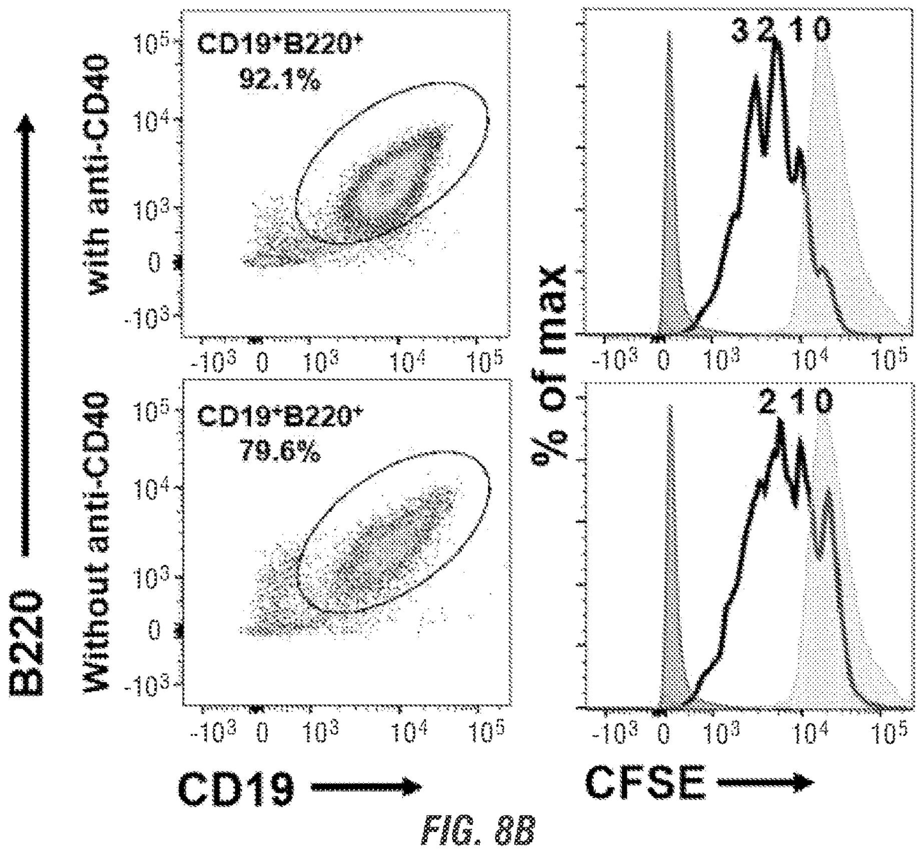
FIG. 8B shows the comparison of B cell population and CFSE intensity with or without anti-CD40 for the PBC micelle-anti-IgM F(ab) group. FIG.

Investigating the proliferation in the B cells, multiple proliferation peaks (i.e., CFSEL®) were detected corresponding to daughter populations for the cells stimulated with either $F(ab')_2$ or with PBC micelle-F(ab) (FIG. 3B), in contrast to the cells stimulated with F(ab) fragments alone or PBC micelle alone (which only show the $CFSE^{hi}$ parent peak). It was also noteworthy that for the PBC micelle-F(ab) stimulation, provision of anti-CD40 signal was not required for B cell activation and proliferation. However, we observed a relatively higher number of viable B cells when anti-CD40 was present (92.1% vs. 79.8%; FIG. 8B). The percentage of B cells that proliferated was found to be similar for $F(ab')_2$ and PBC micelle-F(ab) at 80-90% (FIG. 3B). We also tested and observed the same effect with B cells isolated from spleens of aged (18-month-old) WT mice (FIG. 3C). As an additional measure of B cell activation and proliferation, we measured the concentration of the cytokine, TNFα in the supernatant of the cells stimulated with various groups for 10 days, since TNFα has been reported to be produced by B cells after T-independent BCR crosslinking[32]. Cells stimulated with $F(ab')_2$ or PBC micelle-F(ab) showed significantly higher levels of TNFα secretion than those stimulated with either F(ab), PBC micelle or unstimulated controls (FIG. 3D).

Figure 8C:
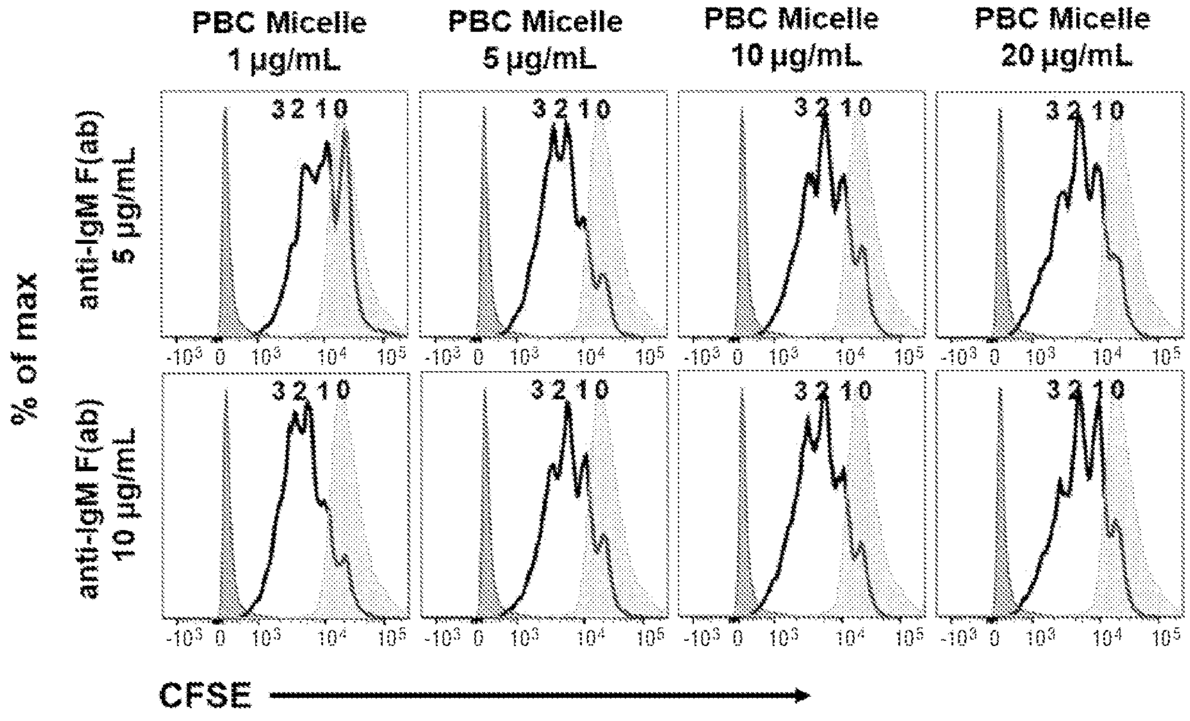
FIG. 8D shows the B cell population and CFSE intensity for cells stimulated with Pluronic® F127-anti-IgM F(ab) and PBC unimer-anti-IgM F(ab). The CFSE histograms denoted by solid black lines with cell generations indicated with numbers, unstained control demoted with dark grey shaded histogram and CFSE stained non-proliferated peak denoted by solid light gray histogram. Data indicates the requirement for the presence of the ionic block and ability to form a micelle in order to induce B cell proliferation.
Figure 8D:
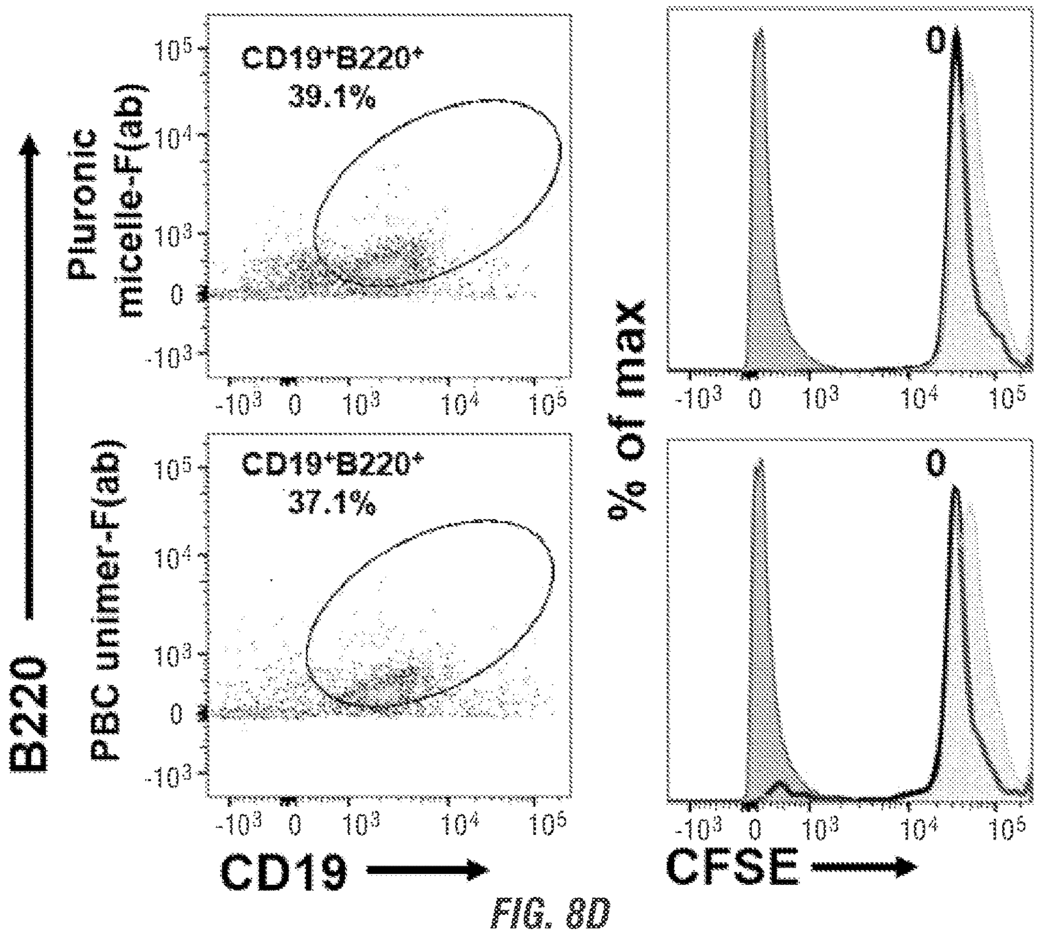

Furthermore, we investigated the BCR crosslinking-induced B cell proliferation for various concentrations of PBC micelle-F(ab) and observed B cell proliferation at concentrations as low as 1 μg/mL of PBC micelles (FIG. 8C). Interestingly, this effect was not observed for PBC unimers (at 0.1 μg/mL concentration—below the CMC for PBC micelles), or for Pluronic® F127micelles at 10 μg/mL (FIG. 8D), indicating that polymer properties such as the PBC chemical structure, specifically the anionic block, and its micellar phase are necessary for this crosslinking.

Ag-Specific B Cell Proliferation Induced by PBC Micelle-Ag Complexes

Figure 4A:
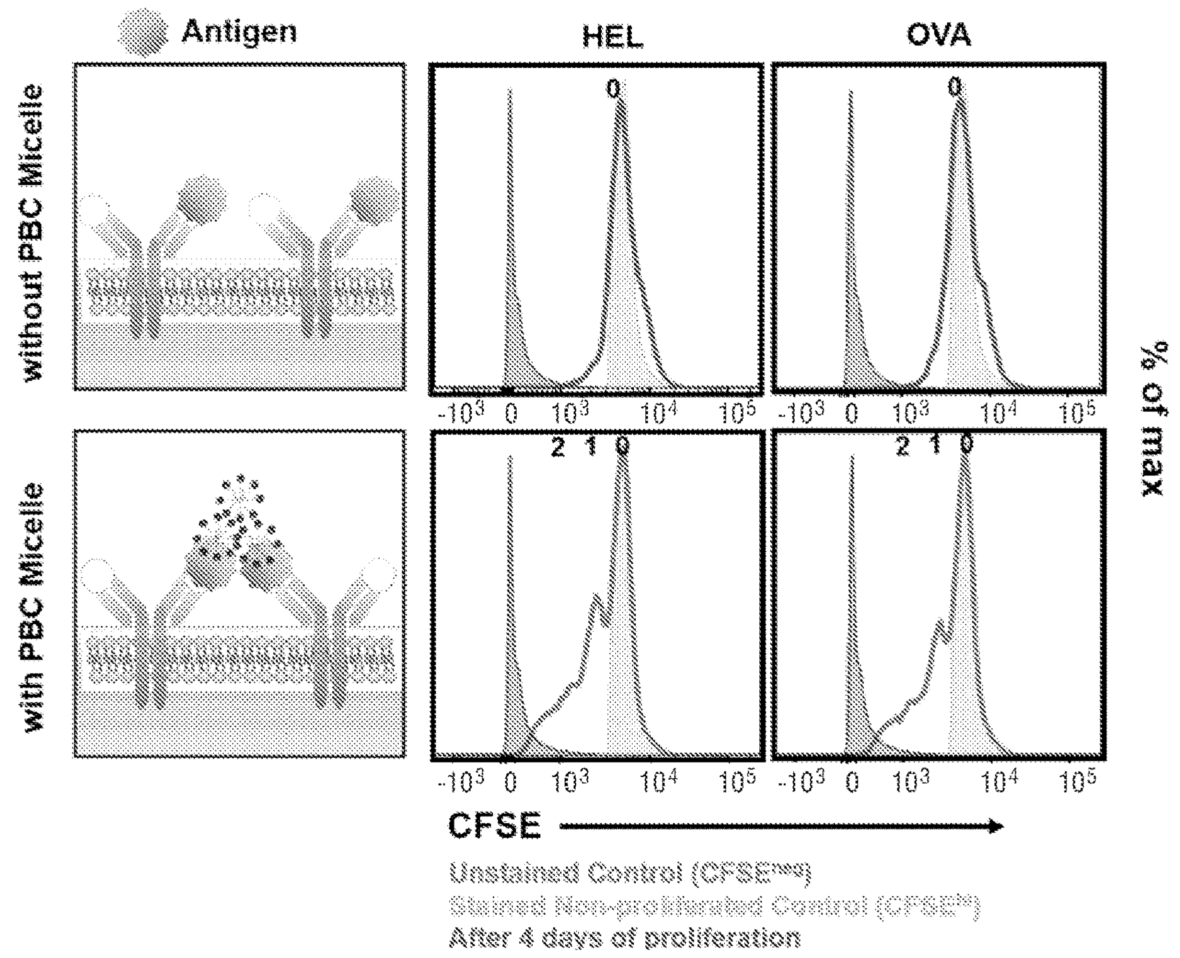
FIG. 4A shows an exemplary schematic of experiment showing stimulation of murine spleen cells stimulated with anti-IgM $F(ab')_2$ (10 μg/mL) as positive control, or antigen (Ag: hen egg white lysozyme (HEL) or ovalbumin (OVA), or PBC micelle (10 g/mL), or PBC micelle-Ag (10 μg/mL each). Anti-CD40 (5 μg/mL) was added to all the treatment groups except unstimulated controls. Corresponding representative histograms for the stimulation groups with CFSE expression (solid lines) for viable B cells (Zombie$^-$CD3$^-$CD19$^+$B220$^+$) generated 4 days after proliferation was initiated. Peaks for CFSE-unstained cells (light grey, filled) are also shown.
Figure 4B:
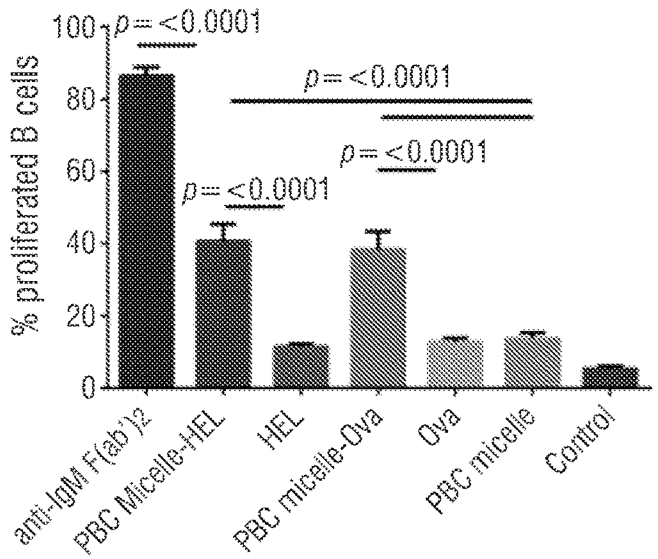
FIG. 4B shows the percent proliferated viable B cells from spleens as determined by CFSEL gating for young WT mice.
Figure 4C:
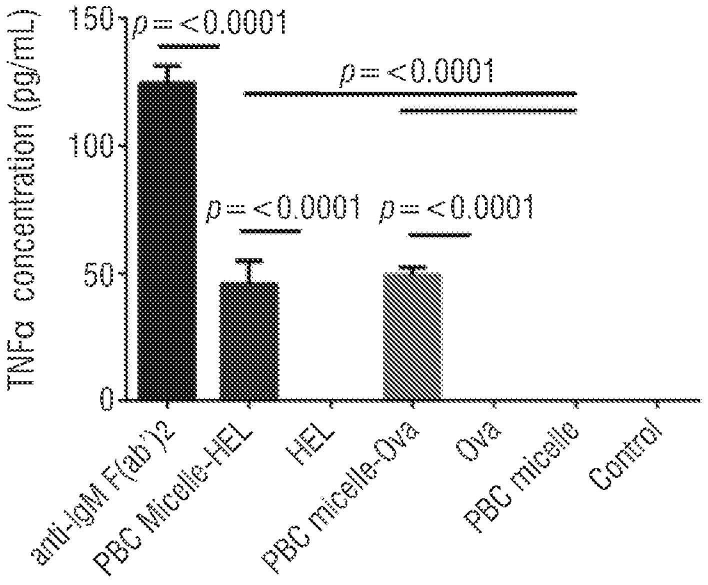
FIG. 4C Concentration of the cytokine, TNFα in supernatants of cells stimulated with different treatment groups for 10 days.
Figure 4D:
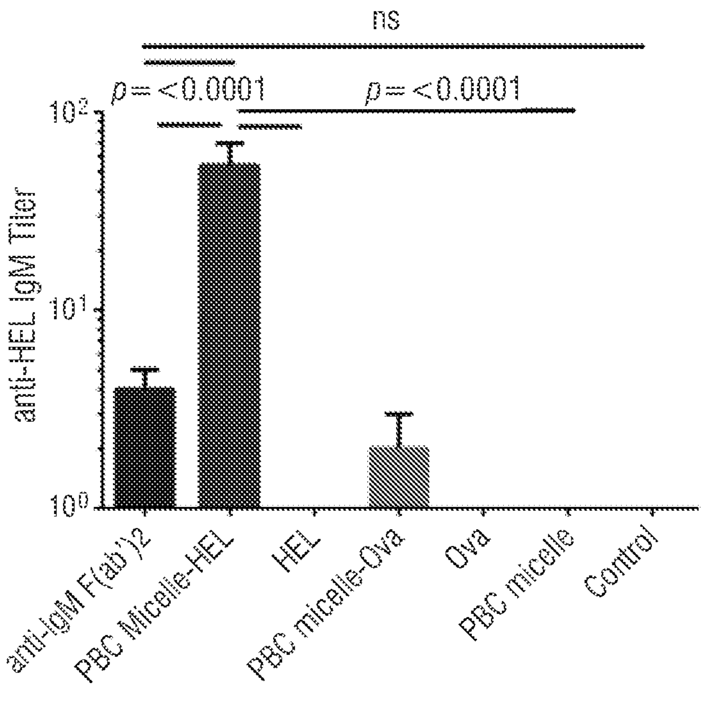
FIG. 4D shows the anti-HEL IgM titers in the supernatants of cells stimulated with different treatment groups.
Figure 4E:
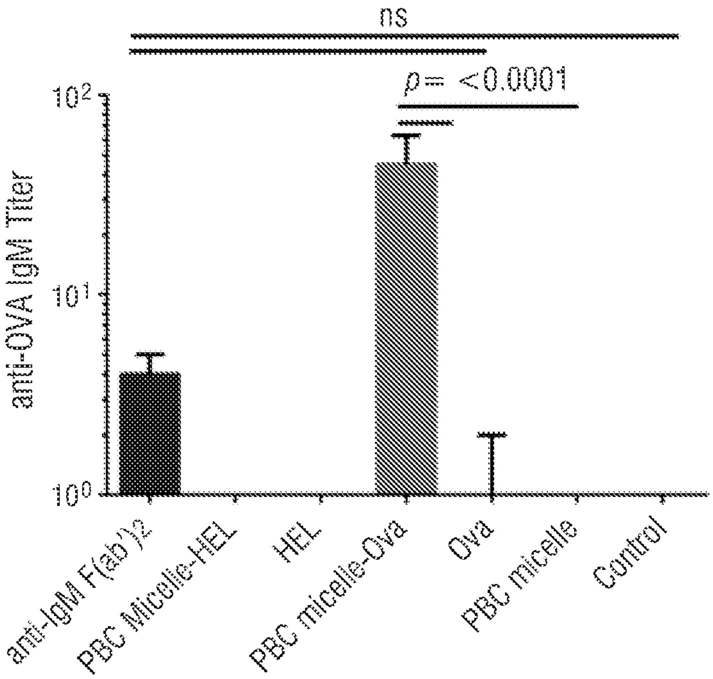
FIG. 4E shows the anti-OVA IgM titers in the supernatants of cells stimulated with different treatment groups. For cell culture, splenic cells (0.5×10$^6$/well) were stimulated in 96 well U-bottom plates. Experiments were performed with cells from both C57BL/6 and BALB/c mice. Data are represented as mean±SEM. Data were analyzed using one-way analysis of variance (ANOVA) followed by Tukey's post hoc test, n=4, ns=not statistically significant. In addition to the significance denoted in the image with the respective p values, mean values for anti-F(ab')$_2$ and PBC micelle-Ag groups in FIGS. 4B and 4C and PBC micelle-Ag groups in FIGS. 4D and 4E are also statistically significant from control with p<0.0001. PBC micelle, HEL, and OVA alone groups are not significant from the medium only control.
Figure 9A:
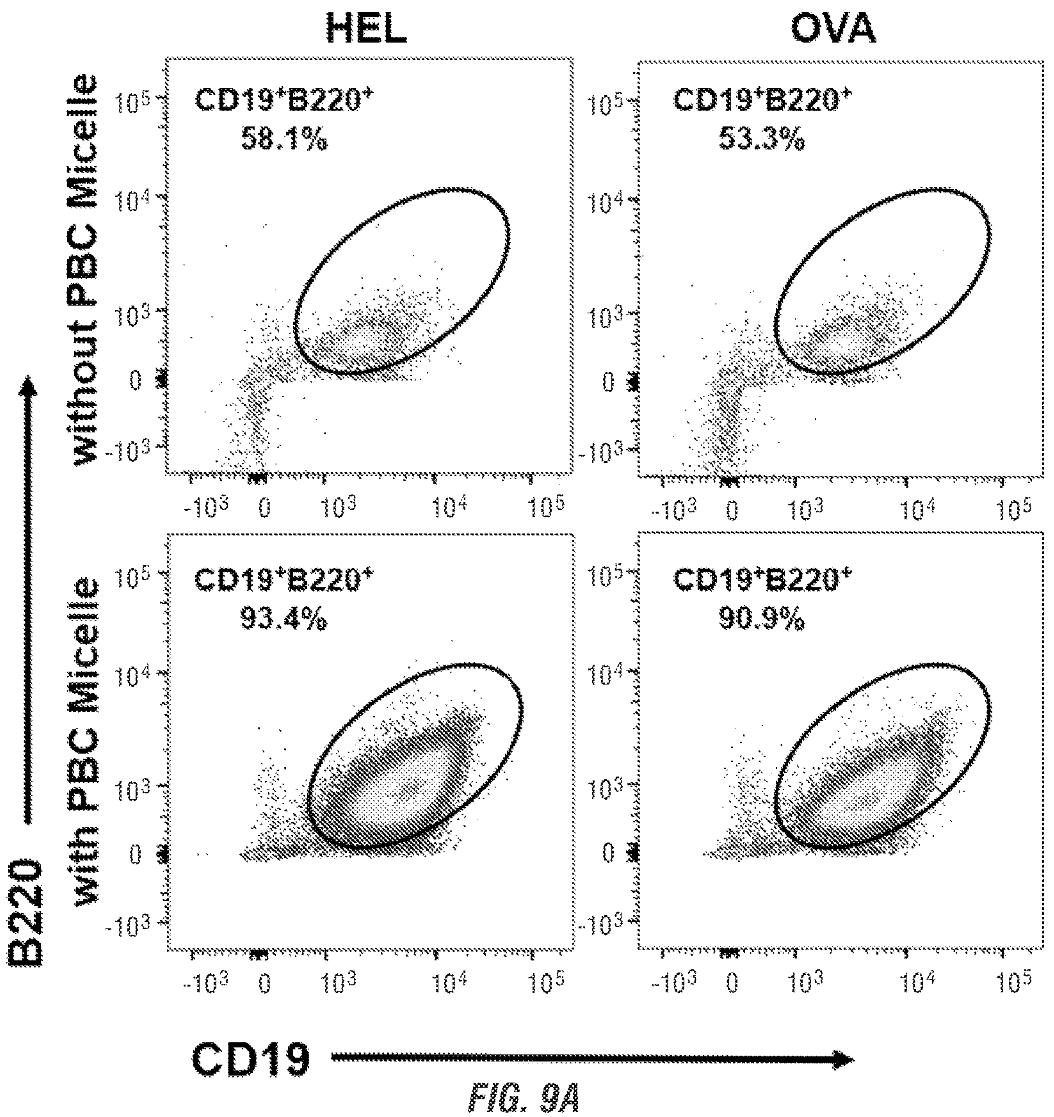
FIG. 9A shows representative B cell gating strategy and percentage of B cell populations for different stimulation groups.
Figure 9B:
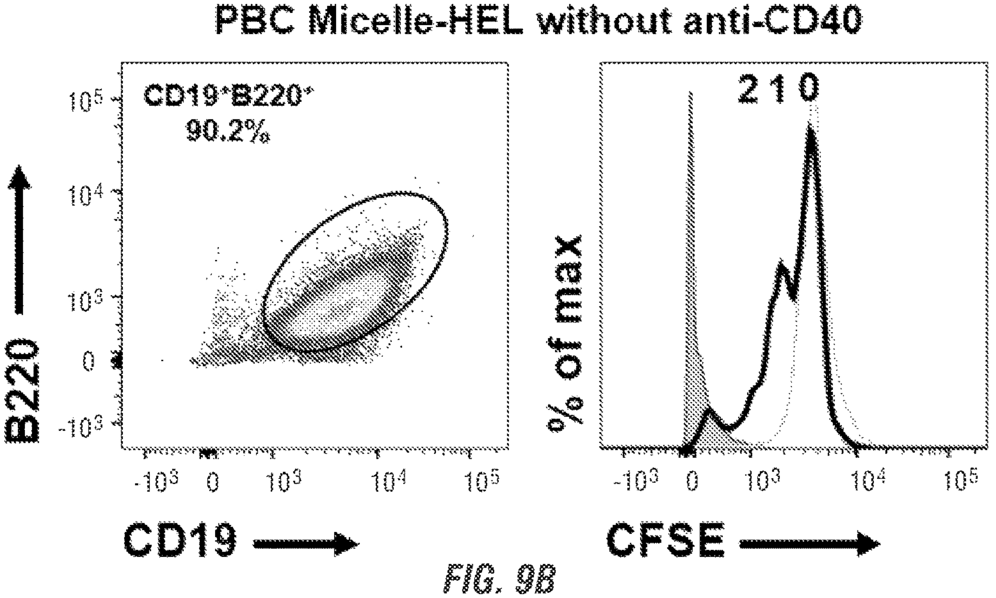
FIG. 9B shows the B cell populations and CFSE expression without anti-CD40 stimulation for the PBC micelle-anti-IgM HEL group.
Figure 9C:
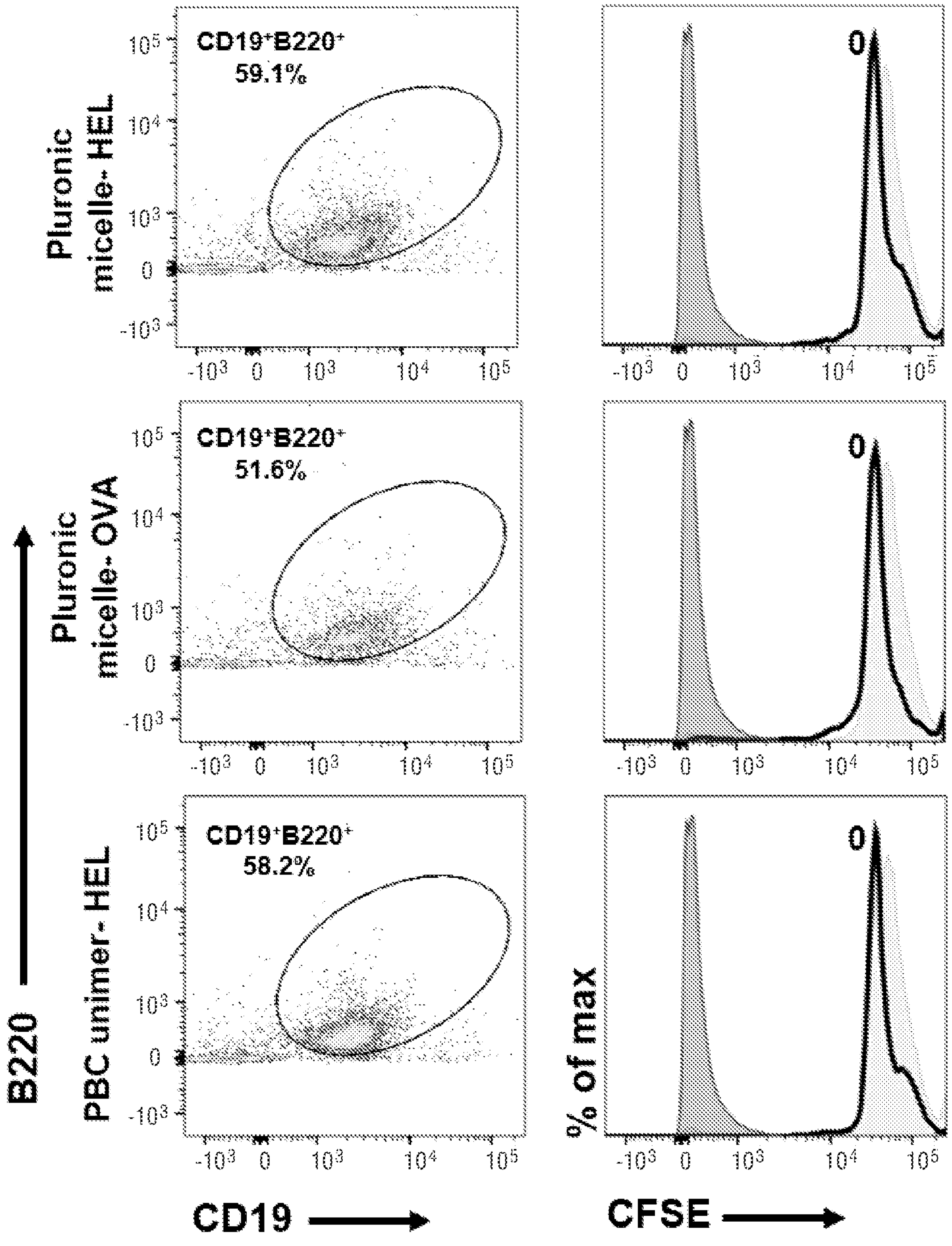
FIG. 9C shows the B cell population and CFSE expression for cells stimulated with Pluronic® F127-HEL, Pluronic® F127-OVA and PBC unimer-HEL. The CFSE histograms denoted by solid black lines with cell generations indicated with numbers, unstained control demoted with dark grey shaded histogram and CFSE stained non-proliferated peak denoted by solid light gray histogram. Data indicates the requirement for the presence of the ionic block and ability to form a micelle in order to induce B cell proliferation.

To investigate if the BCR crosslinking also occurs upon use of PBC micelle-Ag complexes, similar studies were performed where splenic cells from WT mice (both BALB/c and C57BL/6) were stimulated with antigens (10 μg/mL) with or without PBC micelles (10 μg/mL) (FIG. 4A). Both model antigens (HEL and Ova) used for these studies showed similar results. A clear distinction was observed between the total number of viable B cells when stimulated with Ag alone vs with PBC micelle-Ag complexes (FIG. 9A). In terms of B cell proliferation, a significantly higher percentage of proliferation with multiple daughter peaks ($CFSE^{lo}$) was observed after stimulation with PBC micelle-Ag complexes compared to Ag alone (FIGS. 4A-4B, 11, and 12). The concentration of the cytokine TNFα was also significantly higher in supernatants from the cells stimulated with PB micelle-Ag complexes compared to Ag alone (FIG. 4C). Next, we analyzed if these proliferated B cells secreted antigen-specific antibodies. We measured anti-IgM titers in the supernatants of the cells 10 days post-stimulation with different antigens with or without the PBC micelles. We observed significantly higher levels of anti-HEL or anti-OVA titers when the cells were stimulated along with the PBC micelles in contrast to the respective antigen-only stimulation (FIGS. 4D and 4E). The supernatant samples from cells stimulated with all the antigen groups were analyzed for antigen-specific IgM. The titers for non-specific antibodies induced by the PBC micelle-Ag complex were found to be negligible. We used anti-F(ab')$_2$ again as a positive control for stimulation of the cells and observed that this treatment induced significantly higher levels of B cell proliferation than for that induced by the PBC micelle-Ag complexes. However, the antigen-specific antibody response data indicated that these B cells were producing a low level of non-specific antibodies, similar to that of the medium-only control group. Similar to the PBC micelle-F(ab) stimulation, provision of anti-CD40 signal was not required for B cell activation and proliferation with PBC micelle-Ag complexes. However, the anti-CD40 signal was required for Ab production (FIG. 9B). Again, no significant B cell proliferation was observed for cells stimulated with antigens either in combination with PBC unimers or with Pluronic® F127 micelles (FIG. 9C). Together, these studies indicate that the PBC micelle-Ag complexes induced Ag-specific B cell proliferation in contrast to PBC unimers or micelles of other chemistries.

PBC Micelle Scaffolds for Ag Presentation to B Cells

Figure 5A:
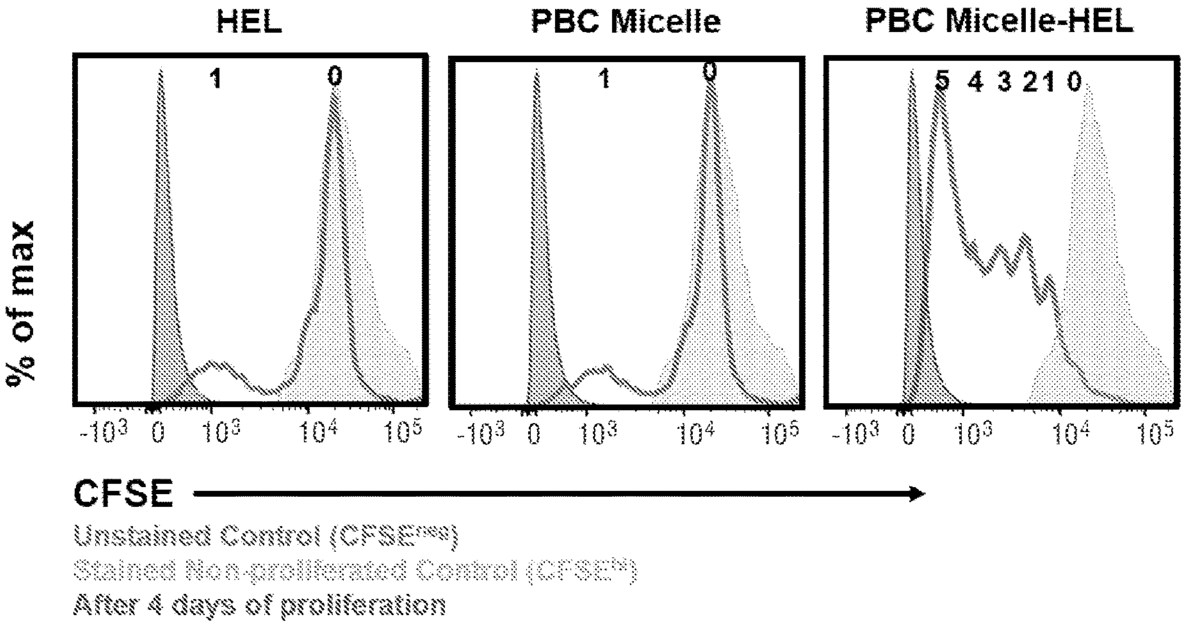
FIG. 5A shows representative histograms for CFSE stained (solid lines) viable B cells (Zombie-CD3-CD19+B220+) 4 days post-stimulation of splenic cells from C57BL/6-Tg(IghelMD4)4Ccg/J mice with various treatment groups (anti-IgM F(ab')$_2$, HEL, OVA, BSA, PBC micelle at 10 μg/mL). Anti-CD40 (5 μg/mL) was added to all the treatment groups except unstimulated controls. Peaks for CFSE-unstained cells (dark grey, filled) and CFSE-stained non-proliferated cells (light grey, filled) are also shown.
Figure 5B:
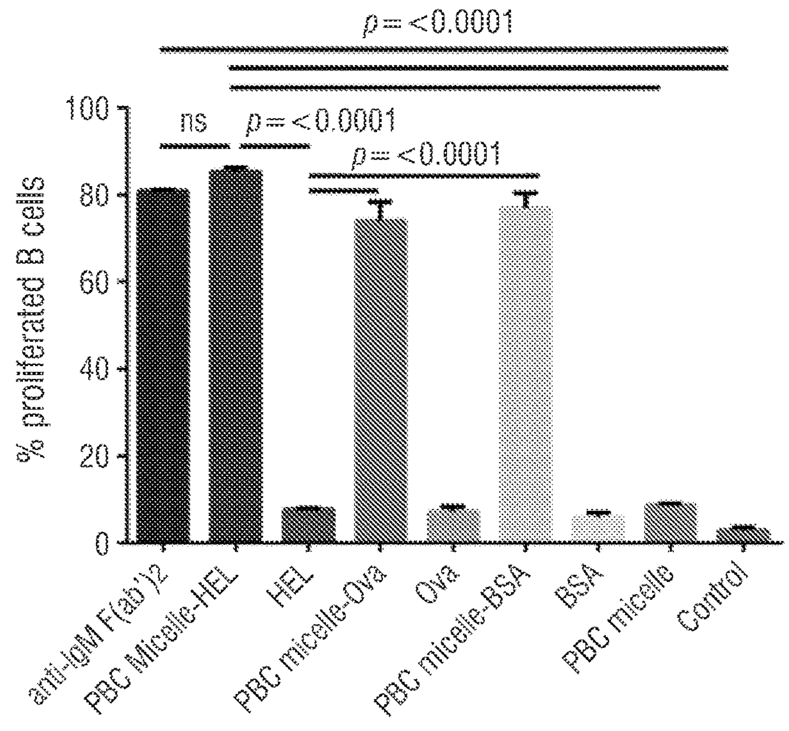
FIG. 5B shows the percent proliferated viable B cells as determined by CFSEL gating.
Figure 5C:
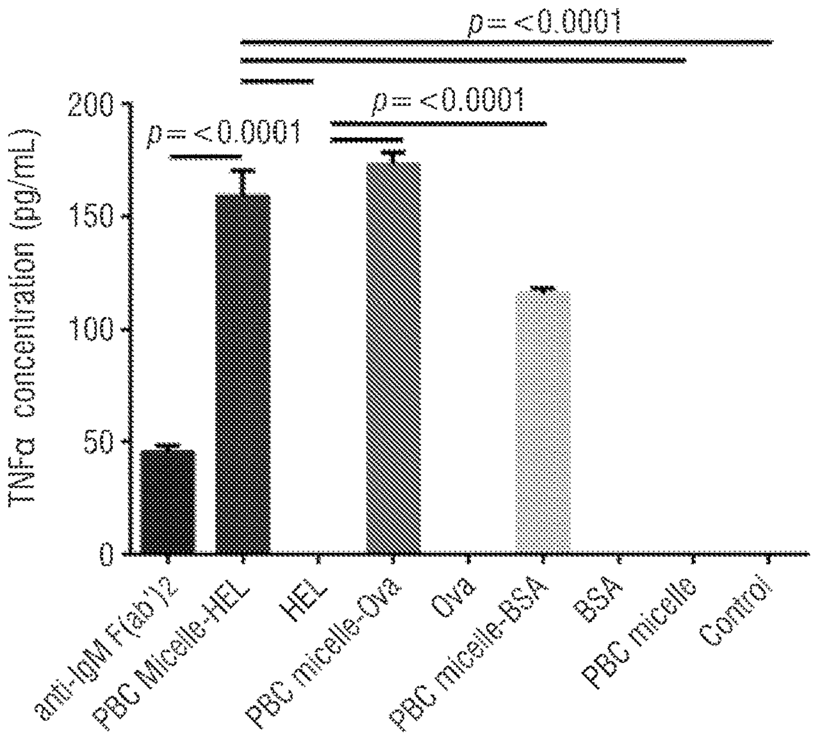
FIG. 5C shows the concentration of the cytokine, TNFα in the supernatants of cells stimulated with different treatment groups for 10 days.
Figure 5D:
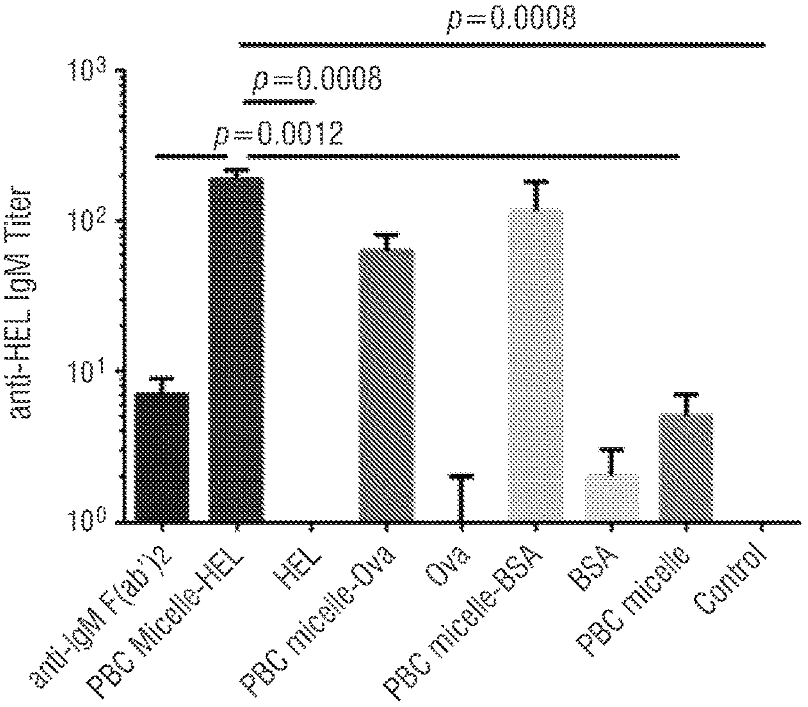
FIG. 5D shows the anti-HEL IgM in the supernatants of cells stimulated with different treatment groups for 10 days. For cell culture, splenic cells (0.5×10$^6$/well) were stimulated in 96 well U-bottom plates. Data are represented as mean SEM. Data were analyzed using one-way analysis of variance (ANOVA) followed by Tukey's post hoc test, n=4, ns=not statistically significant. In addition to the significance denoted in the image with the respective p values, mean values for PBC micelle-Ag groups in FIGS. 5B-5D are also statistically significant from control with p<0.0001. PBC micelle, HEL, OVA, F1-V are not significant from medium only control.
Figure 10A:
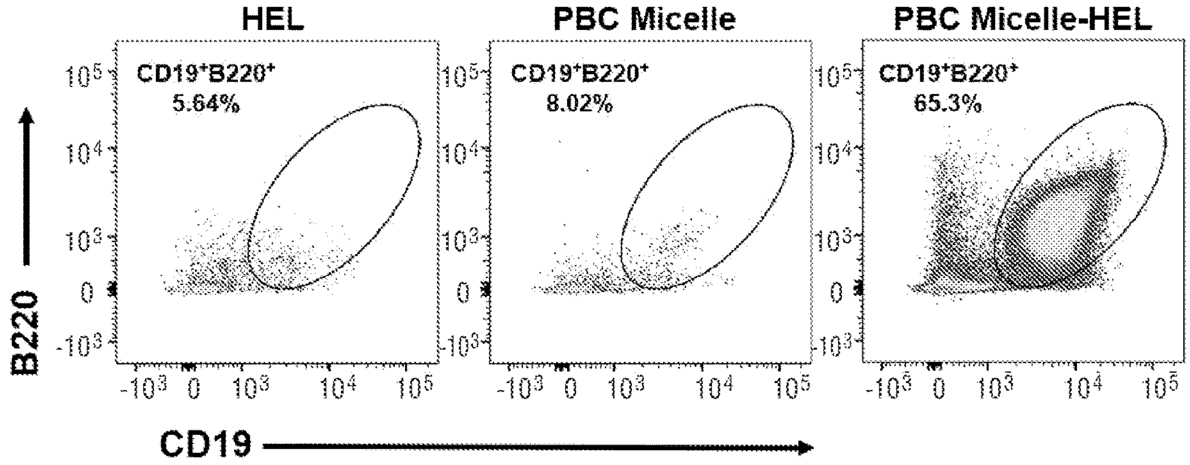
FIG. 10A shows a representative B cell gating strategy and percentage of B cell populations for different stimulation groups of hen egg white lysozyme (HEL) antigen, PBC micelles, and PBC micelles with (HEL) antigen splenic cells from C57BL/6-Tg(IghelMD4)4Ccg/J mice.

Next, we investigated the proliferation of B cells stimulated with PBC micelle-Ag complexes in a transgenic (Ighel Tg) mouse model[33], in which majority of BCRs on splenic B cells are specific to HEL. Our hypothesis was that this increase in Ag-specific BCR repertoire would lead to enhanced PBC micelle-Ag complex-BCR engagement and hence, increased B cell proliferation (compared to WT mice). Splenic cells isolated from Ighel Tg mice were cultured and stained with CFSE on day 0, following which, they were stimulated with HEL alone (10 μg/mL), PBC micelle (10 μg/mL) alone, or with PBC micelle-HEL complex. At least five proliferation peaks (CFSEL$^{lo}$) for the corresponding daughter populations were observed for the B cells stimulated with PBC micelle-HEL complex (FIG. 5A). The viable B cell population four days post-stimulation was also the highest for this group (FIG. 10A). We observed a small peak with some proliferation in cells stimulated with the HEL or PBC micelle-only groups that were similar to that of the unstimulated controls. The percentage of proliferated B cells were at about 80% with the Ighel Tg mouse model (in contrast to about 40% for WT mice) (FIGS. 5B and 4B), supporting our hypothesis. We also measured the concentrations of TNFα and anti-HEL IgM in the supernatants and found significantly higher levels of the antibody and cytokine secretion from cells stimulated with the PBC micelle-HEL complex, compared to HEL alone (FIGS. 5C and 5D). The anti-HEL IgM titers in supernatants of cells stimulated with PBC micelle-HEL complex for the Ighel Tg mice was about 2.5-fold higher than that of cells supernatants from WT mice, correlating with the higher proliferation (FIGS. 4B and 4D, 5B and 5C). A surprising finding was that, even though most B cells from the Ighel Tg mice were HEL-specific, we observed similar levels of B cell proliferation with PBC micelle-OVA complex and PBC micelle-bovine serum albumin (BSA)-complex treatments (FIG. 5B). However, based on anti-HEL IgM measurements in the supernatants, we observed that the levels of anti-HEL IgM from cells stimulated with PBC micelle-OVA complexes or PBC micelle-BSA complexes were similar to that of cells stimulated with the PBC micelle-HEL complexes (FIG. 5C). Our hypothesis to explain this interesting observation is that the PBC micelles must be acting as a scaffold for antigens that are able to stimulate the B cells and lead to the generation of antigen-specific antibodies. In contrast, stimulation with Pluronic® F127 micelle+HEL or PBC unimers+HEL did not lead to B cell proliferation (FIG. 0C), once again confirming the importance of the PBC micelle-Ag complex induced Ag-specific B cell proliferation in contrast to PBC unimers or micelles of other chemistries.

PBC Micelle Platform for In Vitro Antibody Production

Figure 6A:
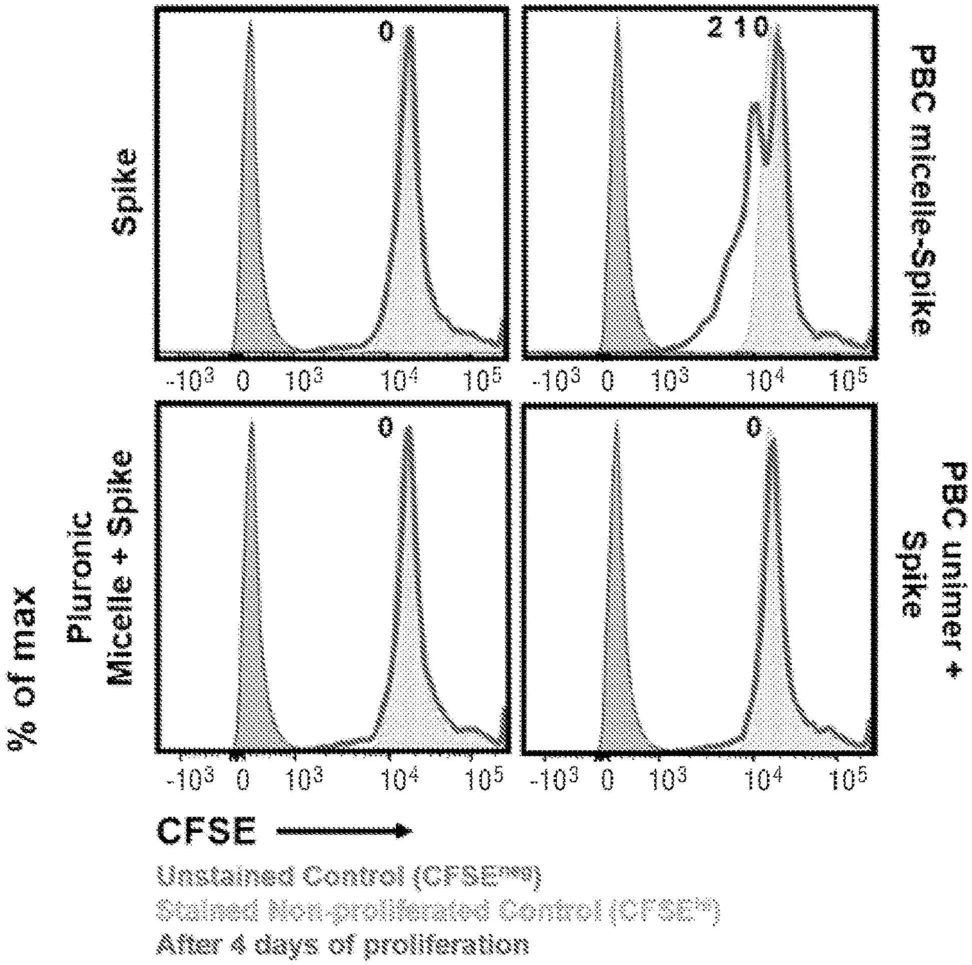
FIG. 6A shows histograms depicting CFSE intensity of B cells stimulated with various treatment groups with or without Spike protein for 4 days from splenic cell population obtained from WT C57BL/6 mice or BALB/c mice were stimulated in 96-well U-bottom plates at a density of 0.5×10$^6$/well. Anti-CD40 (5 μg/mL) was added to all the treatment groups except unstimulated controls. Spike protein from SARS-CoV-2 (10 μg/mL) and F1-V from *Y. pestis* (10 μg/mL) was used with or without PBC micelle (10 μg/mL) or Pluronic® F127 micelle (10 μg/mL) or PBC unimers (10 μg/mL).
Figure 6B:
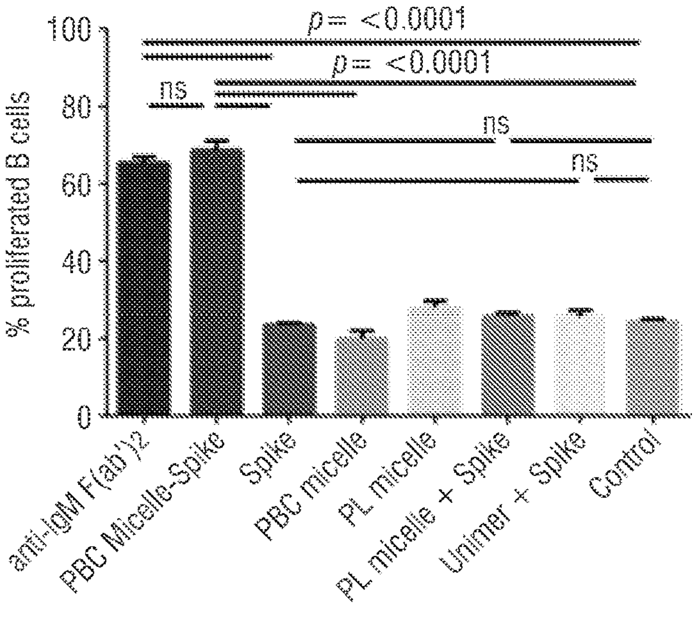
FIG. 6B shows the percent proliferated viable B cells as determined by gating on CFSEL® cells from splenic cell population obtained from WT C57BL/6 mice or BALB/c mice were stimulated in 96-well U-bottom plates at a density of 0.5×10$^6$/well. Anti-CD40 (5 μg/mL) was added to all the treatment groups except unstimulated controls. Spike protein from SARS-CoV-2 (10 μg/mL) and F1-V from *Y. pestis* (10 μg/mL) was used with or without PBC micelle (10 μg/mL) or Pluronic® F127 micelle (10 μg/mL) or PBC unimers (10 μg/mL).
Figure 6C:
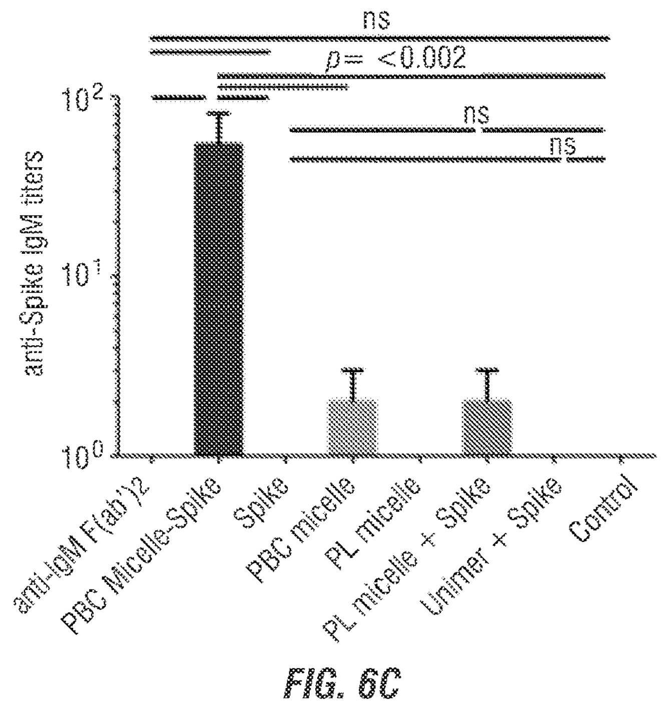
FIG. 6C shows the anti-Spike protein IgM titers measured in the supernatants of the stimulated cells after 10 days from splenic cell population obtained from WT C57BL/6 mice or BALB/c mice were stimulated in 96-well U-bottom plates at a density of 0.5×10$^6$/well. Anti-CD40 (5 μg/mL) was added to all the treatment groups except unstimulated controls. Spike protein from SARS-CoV-2 (10 μg/mL) and F1-V from *Y. pestis* (10 μg/mL) was used with or without PBC micelle (10 μg/mL) or Pluronic® F127 micelle (10 μg/mL) or PBC unimers (10 μg/mL).
Figure 6D:
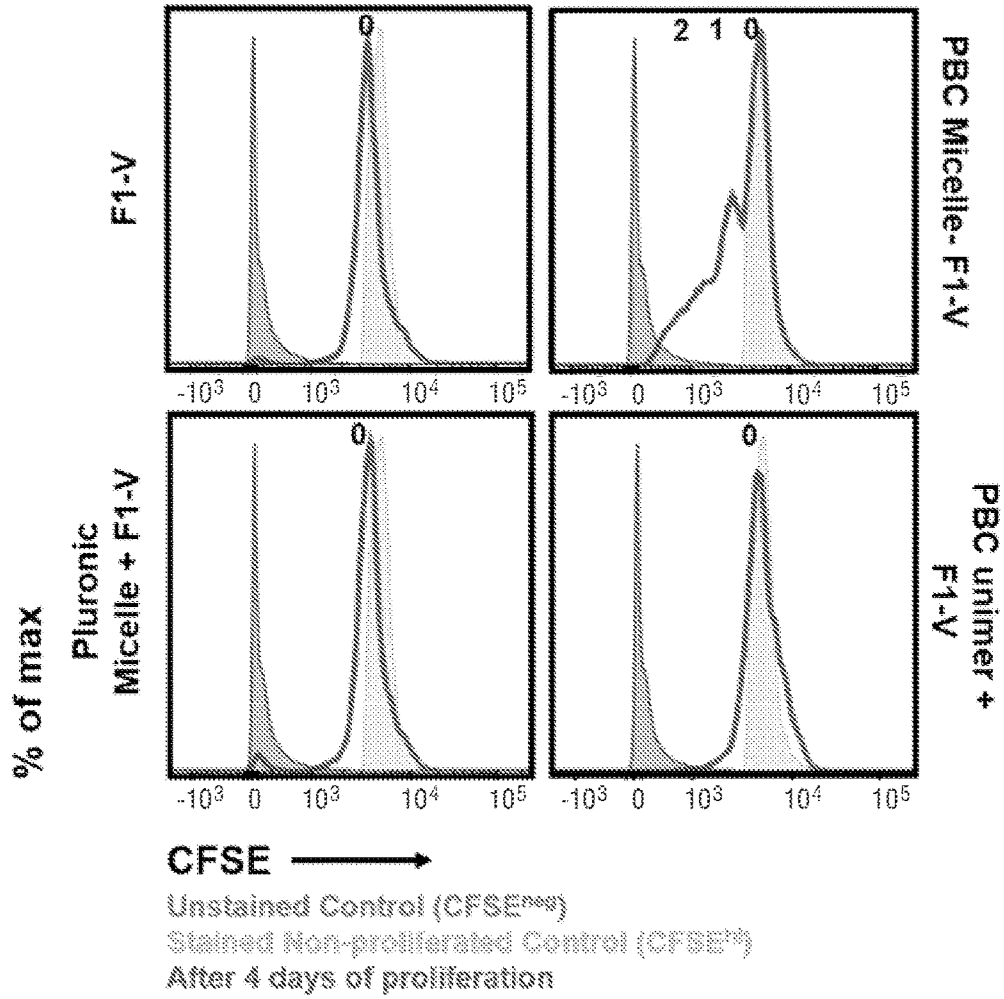
FIG. 6D shows the histograms depicting CFSE intensity of B cells stimulated with various treatment groups with or without F1-V for 4 days from splenic cell population obtained from WT C57BL/6 mice or BALB/c mice were stimulated in 96-well U-bottom plates at a density of 0.5×10$^6$/well. Anti-CD40 (5 μg/mL) was added to all the treatment groups except unstimulated controls. Spike protein from SARS-CoV-2 (10 μg/mL) and F1-V from *Y. pestis* (10 μg/mL) was used with or without PBC micelle (10 μg/mL) or Pluronic® F127 micelle (10 μg/mL) or PBC unimers (10 μg/mL).
Figure 6E:
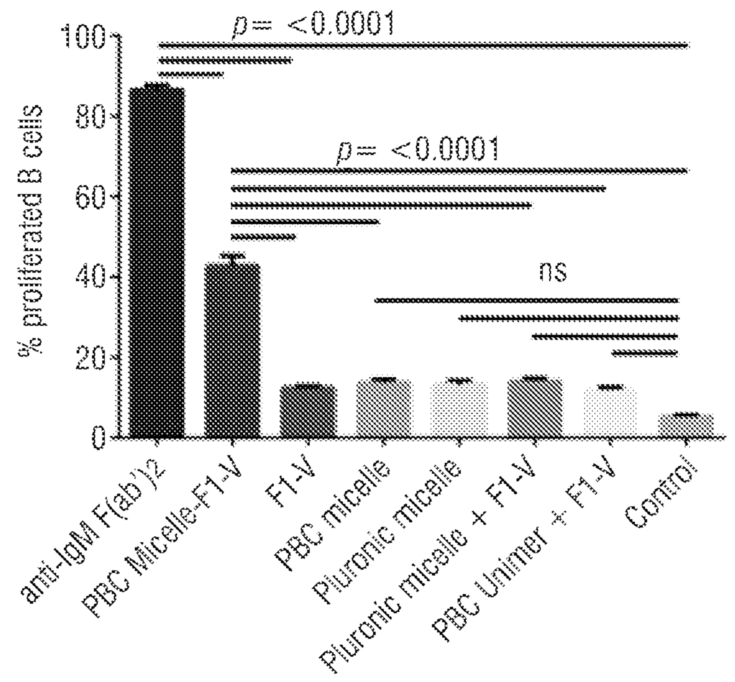
FIG. 6E shows the corresponding percent proliferated viable B cells as determined by gating on CFSEL® cells. Splenic cell population obtained from WT C57BL/6 mice or BALB/c mice were stimulated in 96-well U-bottom plates at a density of 0.5×10$^6$/well. Anti-CD40 (5 μg/mL) was added to all the treatment groups except unstimulated controls. Spike protein from SARS-CoV-2 (10 μg/mL) and F1-V from *Y. pestis* (10 μg/mL) was used with or without PBC micelle (10 μg/mL) or Pluronic® F127 micelle (10 μg/mL) or PBC unimers (10 μg/mL).
Figure 6F:
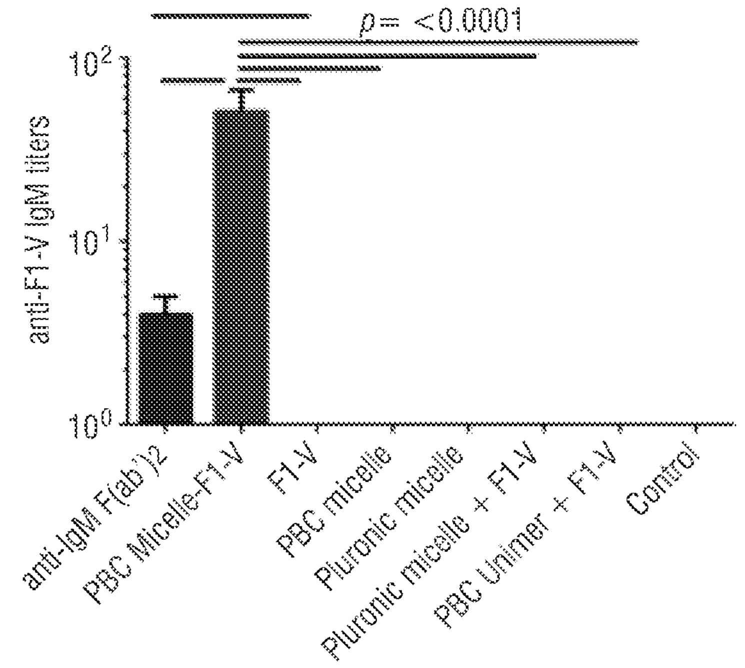
FIG. 6F shows the anti-F1-V IgM titers measured in the supernatants of the stimulated cells after 10 days from splenic cell population obtained from WT C57BL/6 mice or BALB/c mice were stimulated in 96-well U-bottom plates at a density of 0.5×10$^6$/well. Anti-CD40 (5 μg/mL) was added to all the treatment groups except unstimulated controls. Spike protein from SARS-CoV-2 (10 μg/mL) and F1-V from *Y. pestis* (10 μg/mL) was used with or without PBC micelle (10 μg/mL) or Pluronic® F127 micelle (10 μg/mL) or PBC unimers (10 μg/mL). Data are represented as mean±SEM. Data were analyzed using one-way analysis of variance (ANOVA) followed by Tukey's post hoc test, n=2-4, ns=not statistically significant. The responses induced by PBC micelle alone, Spike protein alone, F1-V protein alone, Pluronic® F127 micelle alone, and PBC unimers alone are not significant from medium only control.

Since we observed anti-IgM antibodies in the supernatants of the B cells stimulated with the PBC micelle-Ag complexes for the model antigens, we sought to determine if these observations could be exploited to use these scaffolds as a platform technology for the production of therapeutic antibodies in vitro. To investigate this, we used Spike protein from SARS-CoV-2 and recombinant fusion protein, F1-V from *Y. pestis* with the PBC micelles and evaluated in vitro production of antibodies and B cell proliferation using CFSE as described previously. Our results were consistent with the experiments with the model antigens and indicated that cells stimulated with the PBC micelle-Ag complexes exhibited daughter cell populations, but cells stimulated with Ag only or with Pluronic® F127 micelle+Ag or PBC unimers+Ag did not (FIGS. 6A-6E). As a result, only cell culture supernatants in cells stimulated with the PBC micelle-Ag complexes showed anti-Spike IgM or anti-F1-V IgM (FIGS. 6C and 6F). Even though we observed proliferation in the cells stimulated with anti-IgM F(ab')$_2$ (positive control), we did not observe antigen-specific antibodies in the supernatants of these cells. Hence, the ability of the PBC micelle scaffolds to crosslink BCRs, along with the synergistic effect provided by costimulatory signals induced by anti-CD40 could serve as a novel platform technology for rapid and efficient production of antigen-specific therapeutic antibodies, which may be effective in the treatment of individuals affected by diseases such as COVID-19 or pneumonic plague.

Discussion

Host responses generated towards vaccines are complex and diverse in nature, with the B cell response being an essential contributor towards conferring protective immunity. Hence, the design of vaccine adjuvants has largely been focused on improving the B cell and Ab responses[34]. An in-depth understanding of the mechanisms of B cell activation by adjuvants that drive protective Ab responses has been extensively explored.

However, the mechanism(s) underlying B cell activation by polymeric micelle adjuvants is relatively unknown. In this work, we studied the mechanism of activation of cationic PBC micelle adjuvants. While pursuing this, interestingly, we discovered that the same mechanism(s) may not be operative for all types of micelle adjuvants, calling for the use of appropriate adjuvant chemistries for specific applications instead of a "one-size-fits-all" approach.

The enhancement in the in vivo Ab response induced by the PBC micelles was short-lived, in contrast to that induced by a traditional adjuvant such as MPLA (FIGS. 1A-D). However, immunization with a combination of PBC micelles and MPLA induced a synergistic enhancement in the Ab response, including IgM production due to BCR crosslinking by the PBC micelles and immunoglobulin isotype switching facilitated by MPLA at later time-points. These results provide strong rationale for the use of combination adjuvants that may be beneficial in scenarios where both Ab isotypes and the induction of both rapid and long-lived immunity are important components of protective immunity. Our own work has shown the use of such a combination adjuvant strategy in the design of nanovaccines against pneumonic plague (D. A. Wagner, S. M. Kelly, A. C. Petersen, N. Peroutka-Bigus, R. J. Darling, B. H. Bellaire, M. J. Wannemuehler, B. Narasimhan, Single-dose combination nanovaccine induces both rapid and long-lived protection against pneumonic plague. *Acta Biomater.* 100, 326-337 (2019) and influenza (K. A. Ross, H. Loyd, W. Wu, L. Huntimer, S. Ahmed, A Sambol, et al., Polyanhydride-based H5 hemagglutinin influenza nanovaccines elicit protective virus neutralizing titers and cell-mediated immunity, *Int J Nanomed,* 2015; 10:229-243; K. Ross, J. Adams, H. Loyd, S. Ahmed, A. Sambol, S. Broderick, K. Rajan, M. Kohut, T. Bronich, M. J. Wannemuehler, S. Carpenter, S. Mallapragada, B. Narasimhan, Combination nanovaccine demonstrates synergistic enhancement in efficacy against influenza. *ACS Biomater. Sci. Eng.* 2, 368-374 (2016); K. Ross, S. Senapati, J. Alley, R. Darling, J. Goodman, M. Jefferson, M. Uz, B. Guo, K. J. Yoon, D. Verhoeven, M. Kohut, S. Mallapragada, M. Wannemuehler, B. Narasimhan, Single dose combination nanovaccine provides protection against influenza A virus in young and aged mice. *Biomater. Sci.* 7, 809-821 (2019)).

It is well known that, unlike T cells, B cells can recognize antigen in its native form and that their activation can be mediated in a T cell-independent manner[35]. This process involves the crosslinking of the BCRs by repetitive antigen epitopes. Our studies in this work demonstrate that the PBC micelles that have been shown previously to associate with antigens[8] can crosslink BCRs leading to B cell activation. We first investigated the interaction of the PBC micelle-Ag complexes with the BCRs by analyzing Nur77 expression. Nur77/NR4A1 belongs to a subfamily of orphan nuclear receptors (NR) known as NR4A (encoded in the Nr4a1-3 gene)[29], which plays an important role in cell survival and inflammatory signaling events. Nur77 expression has also been shown to be rapidly induced due to Ag receptor signaling in B lymphocytes[36]. The engagement of BCRs with PBC micelle-Ag complexes led to the induction of a strong BCR signal that was similar to that induced by anti-IgM $F(ab')_2$ (FIGS. 2A-B). In stark contrast, other micelle chemistries such as the non-ionic Pluronic® F127 or non-micellar PBC unimers did not exhibit Nur77 expression. These results provide further support to our hypothesis that the biomaterial adjuvant chemistry and the ability to form micelles both play a crucial role in interactions with antigens and the BCRs.

Figure 3E:
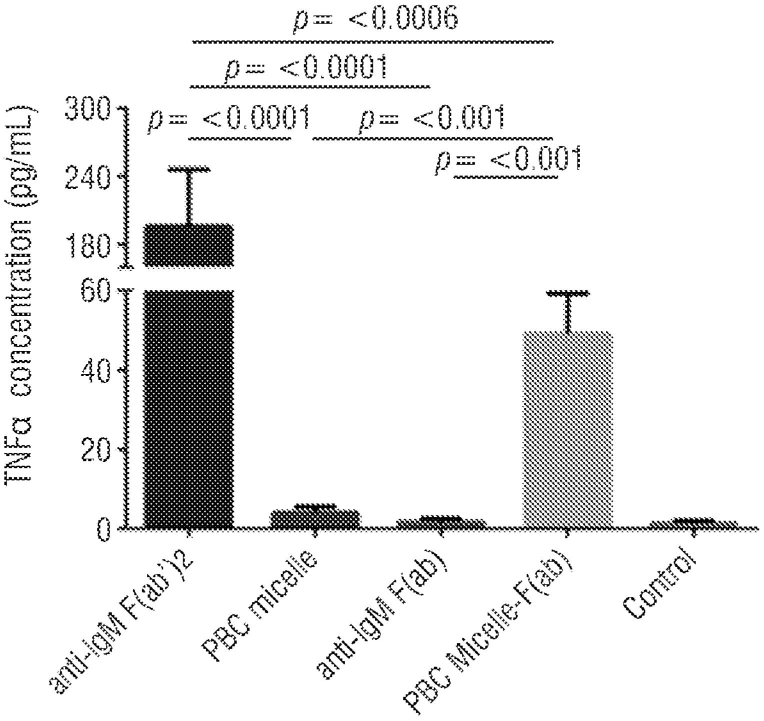
FIG. 3E shows the concentration of the cytokine, TNFα in supernatants of cells stimulated with different treatment groups for 10 days. For cell culture, splenic cells (0.5×106/well) were stimulated in 96 well U-bottom plates. Data are represented as mean SEM. Data were analyzed using one-way analysis of variance (ANOVA) followed by Tukey's post hoc test, n=5, ns=not statistically significant. In addition to the significance denoted in the image with the respective p values, mean values for anti-F(ab')2 and PBC micelle-anti-IgM F(ab) are also statistically significant from control for FIGS. 3C-3E with p<0.0001 and PBC micelle, anti-IgM F(ab) groups are not significant from control.

As a proof-of-concept to demonstrating BCR crosslinking by the PBC micelles, we utilized anti-IgM $F(ab')_2$ and anti-IgM F(ab) fragments. The earliest report of the crosslinking model of B cell activation also utilized these molecules and showed that the monomeric F(ab) fragments do not activate B cells, while the dimeric $F(ab')_2$ did[37]. Our results (FIGS. 3A-E) were consistent with these observations and in addition, showed that when the monomeric F(ab) fragments when used together with the PBC micelles for stimulation of splenic cells, B cell survival and proliferation were induced (FIGS. 3C-E).

We also demonstrated that PBC micelle-Ag complexes led to a higher degree of B cell activation and proliferation, compared to soluble Ag alone or Ag associated with PCB unimers or micelles of other chemistries, owing to BCR crosslinking by the PBC micelle-Ag complexes (FIG. 4). The epitope density of antigens has been previously linked with antigen recognition and the efficiency of B cell responses[38,39]. There have also been reports of engineered synthetic particles that can exhibit repetitive orientation of antigens[40]. The PBC micelles by virtue of their association with antigens may be orienting them to create repetitive, high epitope Ag density complexes to crosslink BCRs. Furthermore, the use of vaccine adjuvants that create similar multivalent display of antigens has been shown to lead to a balanced Th1/Th2 response[41]. This may be especially beneficial for rational design of vaccine adjuvants for older adults against respiratory pathogens that induce Th2 response-mediated inflammatory lung pathology[42,43]

Figure 10B:
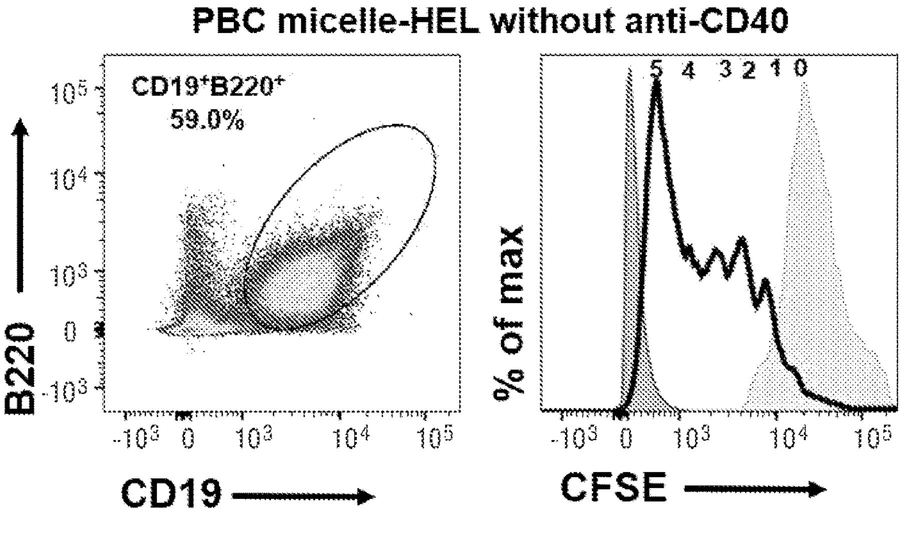
FIG. 10B shows a representative B cell populations and CFSE expression without stimulation with anti-CD40 for the PBC micelle-anti-IgM HEL treatment.
Figure 10C:
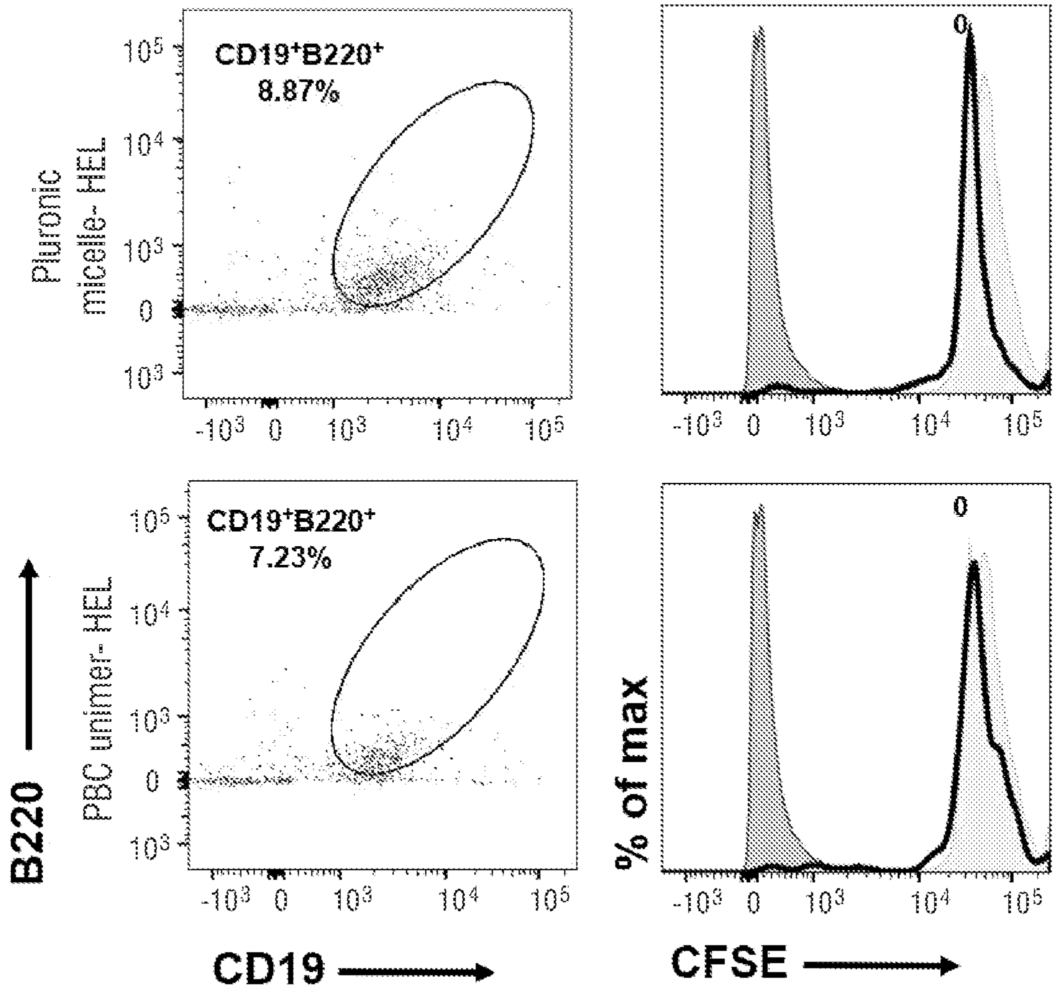
FIG. 10C shows a representative B cell population and CFSE expression for cells stimulated with Pluronic® F127-HEL and PBC unimer-HEL. The CFSE histograms are denoted by solid black lines with cell generations indicated with numbers, the unstained control is denoted by the dark grey shaded histogram, and the CFSE stained non-proliferated peak is denoted by the solid light gray histogram.
Figure 11:
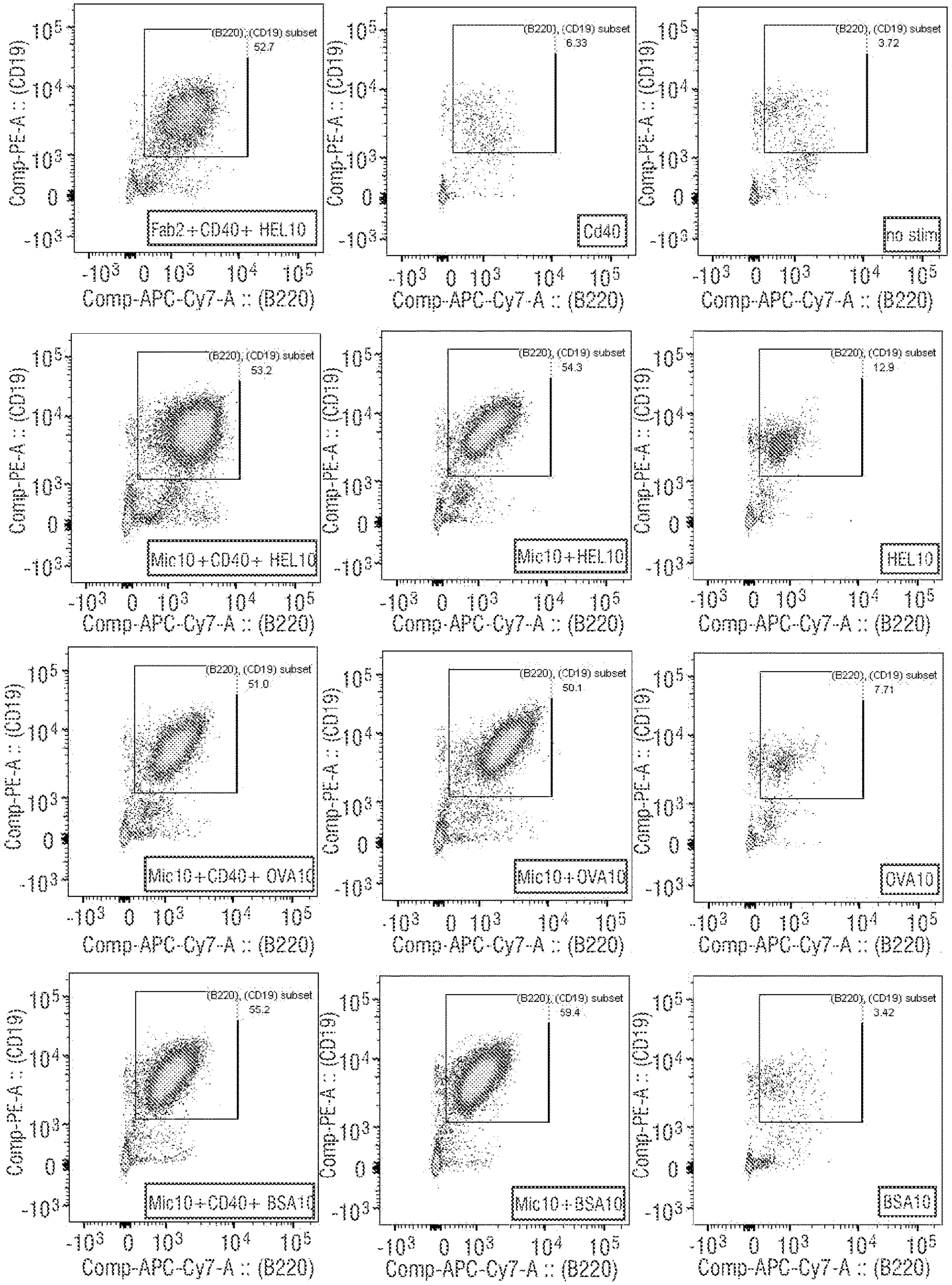
FIG. 11 shows the flow cytometric data of splenocytes from mice transgenic for BCRs recognizing HEL antigen being activated and proliferating (i.e, $CFSE^{LO}$) when stimulated with PBC scaffolds with or without various antigens as shown by the increasing percentage of CD19 and B220 positive cells in the indicated gate (i.e., rectangle).
Figure 12:
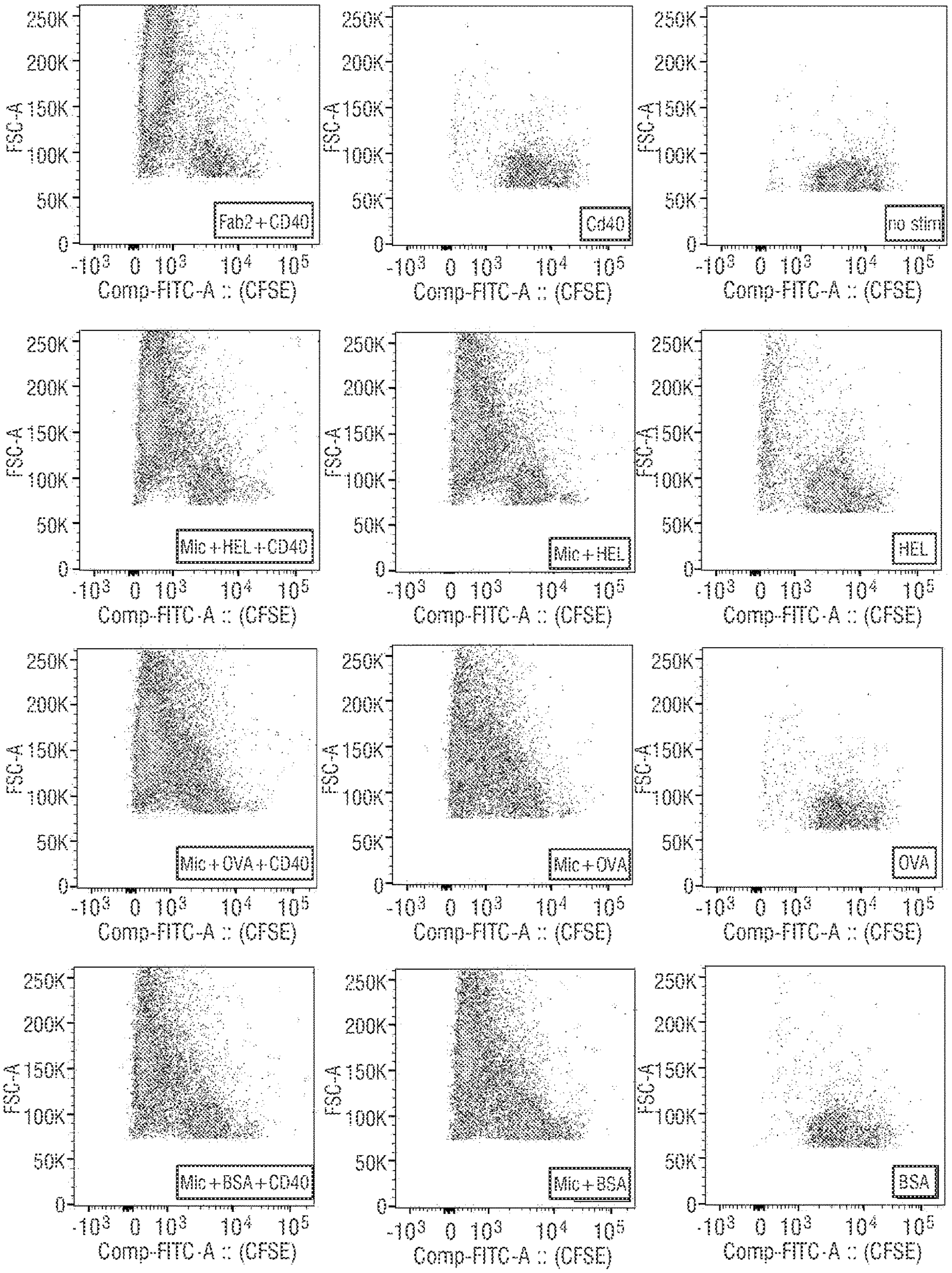
FIG. 12 shows flow cytometric dot plots indicating induced proliferation of B cells stimulated with HEL, OVA, or BSA plus micelle scaffolds. $CFSE^{low}$ cells (i.e., far left population) indicates B cell daughter populations that have proliferated after treatment with PBC scaffolds plus antigen.

It is noteworthy that the presence of anti-CD40 was not required for inducing B cell proliferation. However, we observed a higher degree of proliferation with anti-CD40 and its addition was a requirement for the production of Abs (FIGS. 8B, 9B, and 10B). This is consistent with reports in the literature showing that the engagement of both the BCR and CD40 leads to a synergistic activation of B cells through distinct cellular pathways and that the costimulatory signal is required for forming an efficient synapse[47,48]. According to another report, while maximal B cell proliferation can be achieved without anti-CD40 signal (T cell help), the B cells failed to differentiate into antibody-producing cells (plasma cells)[49].

In addition to increasing the valency of antigens by using PBC micelles, we showed that the recognition of PBC micelle-Ag complexes by BCRs is also proportional to the number of antigen-specific BCRs, using a transgenic mouse model with splenic cells consisting of HEL-specific BCRs. Greater B cell proliferation was accompanied by higher antibody secretions from B cells of the Ighel Tg mice compared to WT mice (FIGS. 5A-D). Interestingly, these TEL-specific B cells stimulated with either OVA or BSA with the PBC micelles induced cell proliferation and anti-HEL IgM production. Since, these different antigens do not share any known B cell epitopes, we hypothesize that the PBC micelle must be acting as a framework/scaffold to present the epitopes to the BCRs in a way that is recognized and that results in generating signals for activation. A similar idea of utilizing self-assembled materials to act as scaffolds in applications for vaccines and drug delivery has been reported before[44], but our PBC micelles and the experiments herein provide credence to this concept.

Importantly, our studies showed that BCR crosslinking is not induced by using only polymeric strands that have not formed micelles (i.e., PBC unimers below the CMC) or by other self-assembled micelle-based formulations (such as non-ionic Pluronic® F127). Even though Pluronic® F127 triblock copolymer is a part of the PBC and forms micelles of the same size, it appears that the outer cationic blocks of PDEAEM in the PBC are playing a major role towards enabling the observed crosslinking effect.

We also demonstrated that this type of B cell activation by PBC micelles can prove to be beneficial in the context of providing an efficient and fast method for production of therapeutic antibodies in vitro. Antibodies are being used extensively as therapeutics for the treatment of several diseases and can prove to be effective therapies for new and emerging diseases[45,46]. This has been exemplified in a big way during the COVID-19 pandemic with emergency use approval from the FDA of multiple antibody therapies to treat individuals with SARS-CoV-2 infections, which has reduced hospitalizations and deaths (M. Tuccori, S. Ferraro, I. Convertino, E. Cappello, G. Valdiserra, C. Blandizzi, F. Maggi, D. Focosi, Anti-SARS-CoV-2 neutralizing monoclonal antibodies: clinical pipeline. *MAbs.* 12, 1-8 (2020)). We exploited the B cell activation mechanisms of PBC micelles to demonstrate production of Ag-specific antibodies that bind to multiple pathogenic antigens (i.e., Spike protein from SARS-CoV-2 and F1-V from *Y. pestis*) in the supernatants of the cells stimulated with PBC micelle-Ag complexes, indicating the versatility and further added value of this approach as a platform technology (FIG. 6).

In summary, the PBC micelles provide a promising platform not only for rational design of vaccine adjuvants but also for the production of therapeutic antibodies. For many vaccine formulations, a combination of vaccine adjuvants is required for generating an optimal immune response which calls for a better understanding of the mechanism of action of these adjuvants. This work, which is focused on understanding the mechanism of action of PBC micelle adjuvants is a step closer towards that goal. Our studies implicate the BCR crosslinking-induced B cell activation as a potential mechanism of action for PBC micelle adjuvants. It would be interesting to evaluate other cationic micelle-based adjuvants for their potential to generate BCR crosslinking and enhanced B cell activation. Finally, the production of therapeutic antibodies in vitro with this platform has the potential to be a disruptive technology for rapid availability of sch countermeasures, especially in the face of a global pandemic. All of these attributes position the PBC micelle platform as a highly versatile tool in the development of multiple countermeasures against emerging and re-emerging infectious diseases.

REFERENCES AND NOTES

1. Zhang, Y. et al. Protective humoral immunity in SARS-CoV-2 infected pediatric patients. *Cell. Mol. Immunol.* 1-3 (2020). doi:10.1038/s41423-020-0438-3
2. Maglione, P. J. & Chan, J. How B cells shape the immune response against *Mycobacterium tuberculosis. Eur. J. Immunol.* 39, 676-86 (2009).
3. Yager, E., Bitsaktsis, C., Nandi, B., McBride, J. W. & Winslow, G. Essential role for humoral immunity during *Ehrlichia* infection in immunocompetent mice. *Infect. Immun.* 73, 8009-16 (2005).
4. Lam, J. H. & Baumgarth, N. The Multifaceted B Cell Response to Influenza Virus. *J. Immunol.* 202, 351-359 (2019).
5. Trimaille, T. & Verrier, B. Micelle-Based Adjuvants for Subunit Vaccine Delivery. 3, 803-813 (2015).
6. Batrakova, E. V. & Kabanov, A. V. Pluronic block copolymers: Evolution of drug delivery concept from inert nanocarriers to biological response modifiers. *J. Control. Release* 130, 98-106 (2008).
7. Determan, M. D., Cox, J. P., Seifert, S., Thiyagarajan, P. & Mallapragada, S. K. Synthesis and characterization of temperature and pH-responsive pentablock copolymers. 46, 6933-6946 (2005).
8. Senapati, S. et al. Pentablock copolymer micelle nanoadjuvants enhance cytosolic delivery of antigen and improve vaccine efficacy while inducing low inflammation. *ACS Biomater. Sci. Eng.* (2019). doi:10.1021/acsbiomaterials.8b01591
9. Darling, R. J. et al. STING pathway stimulation results in a differentially activated innate immune phenotype associated with low nitric oxide and enhanced antibody titers in young and aged mice. *Vaccine* (2019). doi:10.1016/J.VACCINE.2019.04.004
10. Chougnet, C. A. et al. Loss of Phagocytic and Antigen Cross-Presenting Capacity in Aging Dendritic Cells Is Associated with Mitochondrial Dysfunction. *J. Immunol.* 195, 2624-2632 (2015).
11. Kool, M. et al. Alum adjuvant boosts adaptive immunity by inducing uric acid and activating inflammatory dendritic cells. *J. Exp. Med.* 205, 869-882 (2008).
12. Marrack, P., McKee, A. S. & Munks, M. W. Towards an understanding of the adjuvant action of aluminium. *Nat. Rev. Immunol.* 9, 287-293 (2009).
13. McDonald, J. U., Zhong, Z., Groves, H. T. & Tregoning, J. S. Inflammatory responses to influenza vaccination at the extremes of age. *Immunology* 151, 451-463 (2017).
14. Abdul-Cader, M. S., Amarasinghe, A. & Abdul-Careem, M. F. Activation of toll-like receptor signaling pathways leading to nitric oxide-mediated antiviral responses. *Arch. Virol.* 161, 2075-2086 (2016).
15. Luo, Z. et al. A Powerful $CD8^+$ T-Cell Stimulating D-Tetra-Peptide Hydrogel as a Very Promising Vaccine Adjuvant. *Adv. Mater.* 29, 1601776 (2017).
16. Wilson, J. T. et al. PH-responsive nanoparticle vaccines for dual-delivery of antigens and immunostimulatory oligonucleotides. *ACS Nano* 7, 3912-3925 (2013).
17. Keller, S. et al. Neutral polymer micelle carriers with pH-responsive, endosome-releasing activity modulate antigen trafficking to enhance CD8(+) T cell responses. *J. Control. Release* 191, 24-33 (2014).
18. Eby, J. K. et al. Polymer micelles with pyridyl disulfide-coupled antigen travel through lymphatics and show enhanced cellular responses following immunization. *Acta Biomater.* 8, 3210-7 (2012).
19. Boudier, A. et al. The control of dendritic cell maturation by pH-sensitive polyion complex micelles. *Biomaterials* 30, 233-41 (2009).
20. Zhao, M., Li, M., Zhang, Z., Gong, T. & Sun, X. Induction of HIV-1 gag specific immune responses by cationic micelles mediated delivery of gag mRNA. *Drug Deliv.* 23, 2596-2607 (2016).
21. Julie Westerink, M. A. et al. ProJuvant™ (Pluronic F127®/chitosan) enhances the immune response to intranasally administered tetanus toxoid. *Vaccine* 20, 711-723 (2001).
22. Li, C. et al. Synthetic Polymeric Mixed Micelles Targeting Lymph Nodes Trigger Enhanced Cellular and Humoral Immune Responses. *ACS Appl. Mater. Interfaces* 10, 2874-2889 (2018).
23. Jain, A. K. et al. Synthesis, characterization and evaluation of novel triblock copolymer based nanoparticles for vaccine delivery against hepatitis B. *J. Control. Release* 136, 161-169 (2009).

24. Ross, K. et al. Single dose combination nanovaccine provides protection against influenza A virus in young and aged mice. *Biomater. Sci.* 7, 809-821 (2019).
25. Ashouri, J. F. & Weiss, A. Endogenous Nur77 Is a Specific Indicator of Antigen Receptor Signaling in Human T and B Cells. *J. Immunol.* 198, 657-668 (2017).
26. Adams, J. R. & Mallapragada, S. K. Novel Atom Transfer Radical Polymerization Method to Yield Copper-Free Block Copolymeric Biomaterials. *Macromol. Chem. Phys.* 214, 1321-1325 (2013).
27. Aw, M. S., Gulati, K. & Losic, D. Controlling Drug Release from Titania Nanotube Arrays Using Polymer Nanocarriers and Biopolymer Coating. *J. Biomater. Nanobiotechnol.* 02, 477-484 (2011).
28. Cacaccio, J. et al. Pluronic F-127: An Efficient Delivery Vehicle for 3-(1'-hexyloxy)ethyl-3-devinylpyropheophorbide-a (HPPH or Photochlor). *Photochem. Photobiol.* php.13183 (2019). doi:10.1111/php.13183
29. Tan, C. et al. Nur77 Links Chronic Antigen Stimulation to B Cell Tolerance by Restricting the Survival of Self-Reactive B Cells in the Periphery. *J. Immunol.* 202, 2907-2923 (2019).
30. Ashouri, J. F. & Weiss, A. Endogenous Nur77 Is a Specific Indicator of Antigen Receptor Signaling in Human T and B Cells. *J. Immunol.* 198, 657-668 (2017).
31. Hale, B. G., Albrecht, R. A. & Garcia-Sastre, A. Innate immune evasion strategies of influenza viruses. *Future Microbiol.* 5, 23-41 (2010).
32. Tafalla, C. & Granja, A. G. Novel Insights on the Regulation of B Cell Functionality by Members of the Tumor Necrosis Factor Superfamily in Jawed Fish. *Front. Immunol.* 9, 1285 (2018).
33. DY, M., M, J. & CC, G. Development and Follicular Localization of Tolerant B Lymphocytes in Lysozyme/Anti-Lysozyme IgM/IgD Transgenic Mice. *Int. Immunol.* 4, (1992).
34. Loré, K. & Karlsson Hedestam, G. B. Novel adjuvants for B cell immune responses. *Curr. Opin. HIV AIDS* 4, 441-6 (2009).
35. Liao, W. et al. Characterization of T-Dependent and T-Independent B Cell Responses to a Virus-like Particle. *J. Immunol.* 198, 3846-3856 (2017).
36. Mittelstadt, P. R. & DeFranco, A. L. Induction of early response genes by cross-linking membrane Ig on B lymphocytes. *J. Immunol.* 150, 4822-32 (1993).
37. Woodruff, M. F. A., Reid, B. & James, K. Effect of Antilymphocytic Antibody and Antibody Fragments on Human Lymphocytes in vitro. *Nature* 215, 591-594 (1967).
38. Liu, W. & Chen, Y.-H. High epitope density in a single protein molecule significantly enhances antigenicity as well as immunogenicity: a novel strategy for modern vaccine development and a preliminary investigation about B cell discrimination of monomeric proteins. *Eur. J. Immunol.* 35, 505-14 (2005).
39. Bachmann, M. F. et al. The influence of antigen organization on B cell responsiveness. *Science* 262, 1448-51 (1993).
40. Moon, J. J. et al. Enhancing humoral responses to a malaria antigen with nanoparticle vaccines that expand Tfh cells and promote germinal center induction. *Proc. Natl. Acad. Sci. U.S.A* 109, 1080-5 (2012).
41. Little, S. R. Reorienting our view of particle-based adjuvants for subunit vaccines. *Proc. Natl. Acad. Sci. U.S.A* 109, 999-1000 (2012).
42. Bolles, M. et al. A double-inactivated severe acute respiratory syndrome coronavirus vaccine provides incomplete protection in mice and induces increased eosinophilic proinflammatory pulmonary response upon challenge. *J. Virol.* 85, 12201-15 (2011).
43. Iwasaki, A. & Yang, Y. The potential danger of suboptimal antibody responses in COVID-19. *Nat. Rev. Immunol.* 20, 339-341 (2020).
44. Zhang, H., Park, J., Jiang, Y. & Woodrow, K. A. Rational design of charged peptides that self-assemble into robust nanofibers as immune-functional scaffolds. *Acta Biomater.* 55, 183-193 (2017).
45. Buss, N. A., Henderson, S. J., McFarlane, M., Shenton, J. M. & de Haan, L. Monoclonal antibody therapeutics: history and future. *Curr. Opin. Pharmacol.* 12, 615-622 (2012).
46. Marovich, M., Mascola, J. R. & Cohen, M. S. Monoclonal Antibodies for Prevention and Treatment of COVID-19. *JAMA* 324, 131-132 (2020).
47. Wortis, H. H., Teutsch, M., Higer, M., Zheng, J. & Parker, D. C. B-cell activation by crosslinking of surface IgM or ligation of CD40 involves alternative signal pathways and results in different B-cell phenotypes. *Proc. Natl. Acad. Sci. U.S.A* 92, 3348-52 (1995).
48. Haxhinasto, S. A. & Bishop, G. A. Synergistic B cell activation by CD40 and the B cell antigen receptor: role of B lymphocyte antigen receptor-mediated kinase activation and tumor necrosis factor receptor-associated factor regulation. *J. Biol. Chem.* 279, 2575-82 (2004).
49. Rush, J. S. & Hodgkin, P. D. B cells activated via CD40 and IL-4 undergo a division burst but require continued stimulation to maintain division, survival and differentiation. *Eur. J. Immunol.* 31, 1150-1159 (2001).

What is claimed:

1. A nanoscale scaffold composition for in vitro antibody production comprising:

a multiblock copolymer comprising an amphiphilic block and an ionic block which forms micelles in aqueous solutions; an antigen or fragment thereof, wherein said antigen is SARS-CoV-2 virus; and a population of B cells.

2. The nanoscale scaffold composition of claim 1, wherein the multiblock copolymer and antigen crosslink B cell receptors on the B cell surface membrane.

3. The nanoscale scaffold composition of claim 1, wherein the amphiphilic blocks are nonionic.

4. The nanoscale scaffold composition of claim 1, wherein the multiblock copolymer is a pentablock copolymer, nonablock copolymer, or a tridecablock copolymer.

5. The nanoscale scaffold composition of claim 4, wherein the multiblock copolymer is a pentablock copolymer.

6. The nanoscale scaffold composition of claim 5, wherein the pentablock copolymer comprises a core block covalently bonded to two linker blocks and each of the two linker blocks are covalently bonded to ionic blocks.

7. The nanoscale scaffold composition of claim 6, wherein the core block is hydrophobic.

8. The nanoscale scaffold composition of claim 6, wherein the core block is a non-ionic or amphiphilic polymer.

9. The nanoscale scaffold composition of claim 8, wherein the core block comprises repeating units of propylene oxide (PO), butylene oxide (BO), dimethylsiloxane (DMS), ε-caprolactone (CL), L-lactide, lactide-co-glycolic acid (LGA), L-aspartic acid (Asp), L-histidine (His), β-amino ester (bAE), and/or disteroyl phosphatidyl ethanolamine (DSPE).

10. The nanoscale scaffold composition of claim 6, wherein the core block comprises from about 1 to about 20,000 units.

11. The nanoscale scaffold composition of claim 6, wherein at least one of the linker blocks is non-ionic or amphiphilic.

12. The nanoscale scaffold composition of claim 11, wherein at least one of the linker blocks is made of repeating units of ethylene oxide (EO), N-vinyl pyrrolidone (VP), and/or N-isopropyl acrylamide (NIPAAm).

13. The nanoscale scaffold composition of claim 6, wherein at least one of the linker blocks comprise from about 10 to about 20,000 units.

14. The nanoscale scaffold composition of claim 6, wherein the core block and the two linker blocks make a poloxamer represented by the following formula:

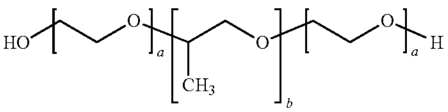

where a is from about 10 to about 20,000 and b is from about 1 to about 20,000.

15. The nanoscale scaffold composition of claim 6, wherein the core block and the two linker blocks comprise poloxamer 407, where a is 101 and b is 56.

16. The nanoscale scaffold composition of claim 6, wherein at least one of the ionic blocks is a substituted aminomethacrylate.

17. The nanoscale scaffold composition of claim 6, wherein the units of at least one of the ionic blocks is represented by the formula:

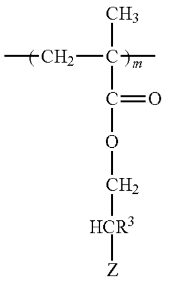

where $R^3$ is either a hydrogen or a $C_{1-6}$ alkyl group;

where Z are selected from the group of $NR^6R^7$, $P(OR^8)_3$, $SR^9$, SH,

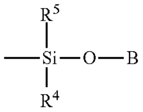 and 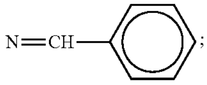;

in which $R^4$, $R^5$, $R^6$, $R^7$, and $R^8$, are either the same or different hydrogen or a $C_{1-6}$ alkyl group and $R^9$ is a tri($C_{1-6}$ alkyl) silyl group, and B is a $C_{1-6}$ alkyl group.

18. The nanoscale scaffold composition of claim 6, wherein at least one of the ionic blocks comprise from about 1 to about 20,000 units.

19. The nanoscale scaffold composition of claim 6, wherein at least one of the ionic blocks is made of units of 2-(N,N-diethylaminoethyl methacrylate).

20. The nanoscale scaffold composition of claim 6, wherein the pentablock copolymer is represented by the formula:

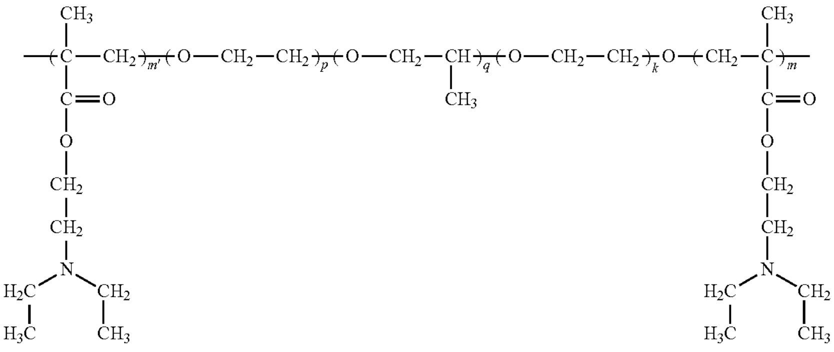

where m and m' is a number in the range of about 1 to about 5,000;

p is a number in the range of about 10 to about 20,000; and k is a number in the range of 0 to about 20,000 and q is a number in the range of about 1 to about 20,000 and m is a number in the range of about 0 to about 50;

m' is a number in the range of about 1 to about 50.

21. The nanoscale scaffold composition of claim 6, wherein said pentablock copolymer is in the amount from about 0.5 to about 10 wt. % of the scaffold.

22. The nanoscale scaffold composition of claim 1, wherein said multiblock copolymer has a central hydrophobic block of polypropylene oxide and two hydrophilic blocks of polyethylene oxide in the amount from about 0.5 to about 10 wt. % of the nanoscale scaffolds.

23. The nanoscale scaffold composition of claim 1, wherein said antigen or fragment thereof is labeled.

24. The nanoscale scaffold composition of claim 1, wherein the antigen is integrated into the scaffold through electrostatic interactions.

25. The nanoscale scaffold composition of claim 1, wherein the multiblock copolymer:antigen ratio is from about 1:5 to about 10:1.

* * * * *